(12) United States Patent
Higashiura et al.

(10) Patent No.: US 8,377,967 B2
(45) Date of Patent: Feb. 19, 2013

(54) PIPERIDINE DERIVATIVE

(75) Inventors: Kunihiko Higashiura, Kato (JP);
Takashi Ogino, Kato (JP); Taizo Ito, Kato (JP); Hiroyuki Iwatsuki, Kato (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 78 days.

(21) Appl. No.: 12/864,878

(22) PCT Filed: Nov. 20, 2008

(86) PCT No.: PCT/JP2008/071097
§ 371 (c)(1),
(2), (4) Date: Jul. 28, 2010

(87) PCT Pub. No.: WO2009/096080
PCT Pub. Date: Aug. 6, 2009

(65) Prior Publication Data
US 2010/0331365 A1   Dec. 30, 2010

(30) Foreign Application Priority Data

Jan. 30, 2008 (JP) ................... 2008-019121

(51) Int. Cl.
*A61K 31/4535* (2006.01)
*C07D 409/02* (2006.01)
*A61P 37/08* (2006.01)

(52) U.S. Cl. ........................ 514/324; 546/202

(58) Field of Classification Search ........................ None
See application file for complete search history.

(56) References Cited

U.S. PATENT DOCUMENTS

| | | | |
|---|---|---|---|
| 3,464,983 A | 9/1969 | Jucker et al. | |
| 3,491,103 A | 1/1970 | Ettingen et al. | |
| 3,682,930 A | 8/1972 | Bourquin et al. | |
| 3,749,786 A | 7/1973 | Bourquin et al. | |
| 3,770,728 A | 11/1973 | Bourquin et al. | |
| 3,853,915 A | 12/1974 | Bourquin et al. | |
| 3,862,156 A | 1/1975 | Bourquin et al. | |
| 3,960,894 A * | 6/1976 | Bourquin et al. | 549/44 |
| 4,024,266 A | 5/1977 | Bastian | |
| 4,609,664 A | 9/1986 | Hasspacher | |
| 4,891,376 A | 1/1990 | Manoury et al. | |
| 4,929,621 A | 5/1990 | Manoury et al. | |
| 5,358,953 A | 10/1994 | Alker et al. | |
| 6,207,683 B1 | 3/2001 | Aberg et al. | |

FOREIGN PATENT DOCUMENTS

| | | |
|---|---|---|
| EP | 0 451 772 A1 | 10/1991 |
| FR | 1 437 412 | 3/1966 |
| FR | 1 502 857 | 11/1967 |
| GB | 1 445 127 * | 8/1976 |
| GB | 1 554 427 A | 10/1979 |
| JP | A-48-81869 | 11/1973 |
| JP | A-49-69677 | 7/1974 |
| JP | A-51-110572 | 9/1976 |
| JP | A-52-3075 | 1/1977 |
| JP | B2-52-17030 | 5/1977 |
| JP | B2-55-8984 | 3/1980 |
| JP | A-57-77673 | 5/1982 |
| JP | A-57-60351 | 12/1982 |
| JP | A-1-104069 | 4/1989 |
| JP | A-3-504855 | 10/1991 |
| JP | A-3-294277 | 12/1991 |
| JP | A-6-504992 | 6/1994 |
| JP | A-2001-519789 | 10/2001 |
| WO | WO 89/10363 A1 | 11/1989 |
| WO | WO 2005/003131 A1 | 1/2005 |

OTHER PUBLICATIONS

Polivka et al. in Collect. Czech. Chem. Comm. vol. 54, No. 9, pp. 2443-2469.*
Patani et al. In Chemical Reviews 1996, 96, 3147-3176.*
International Search Report issued in Patent Application No. PCT/JP2008/071097, dated Jan. 20, 2009.
Polivka, Z. et al., "4*H*-Benzo [4,5]cyclohepta [1,2-*b*] Thiophenes and 9,10-Dihydro Derivatives—Sulfonium Analogues of Pizotifen and Ketotifen; Chirality of Ketotifen; Sythesis of the 2-Bromo Derivative of Ketotifen," *Collect. Czech. Chem. Commun.*, 1989, vol. 54, No. 9, pp. 2443-2469.
Written Opinion issued in Patent Application No. PCT/JP2008/071097, dated Aug. 31, 2010.
Bastian et al., "4*H*-Benzo[4,5]cyclohepta[1,2-b]thiophene," *Helvetica Chimica Acta*, Fasc. Emile Cherbuliez, 1966, vol. 49, No. 26, pp. 214-233.
Bastian et al., "Beitrage zur Chemie des 4,5-Dihydro-10*H*-benzo [5,6]cyclohepta[1,2-*b*]thiophens," *Helvetica Chimica Acta*, 54, Fasc. 1, 1971, pp. 277-282.
Waldvogel et al., "Untersuchungen uber synthetische Arzneimittel 9- und 10-Oxo-Derivate von 9,10-Dihydro-4*H*-benzo[4,5]cyclohepta-[1,2-*b*]thiophenen," *Helvetica Chimica Acta*, vol. 59, Fasc. 3, 1976, pp. 866-877.

* cited by examiner

*Primary Examiner* — Dennis Heyer
(74) *Attorney, Agent, or Firm* — Oliff & Berridge, PLC

(57) ABSTRACT

The present invention provides a compound a piperidine derivative having excellent histamine receptor antagonistic action, which is useful as active ingredients of a pharmaceutical composition, especially an antihistamine. The piperidine derivative of the present invention has a potent histamine receptor antagonistic action. Further, the compound of the present invention shows low brain transfer even in a cerebral receptor binding test where a mouse is orally administered with the compound, so that the compound has preferred properties of alleviating side effects in the central nervous system, such as drowsiness. The piperidine derivative of the present invention is very useful as a novel antihistamine having smaller side effects in the central nervous system, such as drowsiness.

18 Claims, No Drawings

PIPERIDINE DERIVATIVE

TECHNICAL FIELD

The present invention relates to a piperidine derivative and salt and hydrate thereof that are pharmaceutically acceptable, which are useful as pharmaceutical compositions, particularly active ingredients such as antihistamines.

BACKGROUND ART

Histamines are representative chemical mediators that induce allergic reactions, and the histamines are released from cells such as mast cells and basophils when substances that are causative of allergy are entered into the body. The released histamines are bound to a histamine type 1 receptor (H1 receptor) protein to exhibit pharmacological actions such as hypotension, vascular hyperpermeability, constriction of smooth muscles, vasodilatation, or glandular hypersecretion, and involved in the manifestation of allergic reactions and inflammations. As described above, histamines are related to various diseases of human, and the allergic diseases and inflammations can be prevented or cured by controlling their actions. Agents for controlling histamine release and agents for inhibiting the binding of histamines with receptors (antihistamines) are numerously commercially available, and the agents are used in diseases such as bronchial asthma, allergic rhinitis, pollinosis, urticaria, and atopic dermatitis.

However, antihistamines that are conventionally known exhibit some undesired side effects such as sedative action, drowsiness, dizziness, and malaise, based on the actions on the central nervous system; and dry mouth, mucosal dryness, and visual impairment, based on the anti-cholinergic actions; therefore, there are some limitations of use such as prohibition of taking antihistamines before driving automobiles, which in turn cause inconvenience in use. For these reasons, antihistamines which are free from such problems and have excellent effects are in demand from the patients and the medical sites. The present inventors have found a piperidine derivative of the present invention having smaller side effects of the central nervous system and potent antihistamine action.

Piperidine derivatives having a thiabenzo azulene backbone are disclosed in Patent Publications 1 to 13, among which those that are disclosed in Patent Publications 1 to 7 are compounds that are different from the compound of the present invention, in that both of $R_1$ and $R_2$ in the following general formula (I) are a hydrogen. In addition, Patent Publication 8 discloses a compound where $R_1$ in the following general formula (I) is an alkyl which may be substituted by an acyl or a hydroxy, and $R_2$ is a hydrogen or a chlorine. Patent Publications 9 to 13 disclose compounds where $R_1$ is a hydrogen, and $R_2$ is a halogen, an alkyl, or an alkoxy in the following general formula (I). However, Patent Publication 8 discloses that the compound has sedative action, and Patent Publication 9 discloses that a compound has antagonistic actions for ptosis and catalepsy, and suppressive actions for abnormal drop in body temperature and tremors, respectively. In addition, the compounds disclosed in Patent Publications 10 to 13 are described to possess antihistamine action, but do not disclose on the amelioration on the side effects on the central nervous system, such as drowsiness, which is a side reaction of conventional antihistamines, as in the compounds of the present invention. For example, ketotifen fumarate disclosed in Patent Publication 10 is widely used as a second generation antihistamine, it is a matter to be remarked upon use on the side reactions that induced drowsiness. As described above, no reports have been so far made on piperidine derivatives having a thiabenzo azulene backbone having smaller side effects on the central nervous system and potent antihistamine actions as in the compounds of the present invention.

Patent Publication 1: Japanese Patent Laid-Open No. Hei-3-294277
Patent Publication 2: Japanese Unexamined Patent Publication No. 2001-519789
Patent Publication 3: Japanese Unexamined Patent Publication No. Hei-6-504992
Patent Publication 4: Japanese Patent Laid-Open No. Hei-1-104069
Patent Publication 5: Japanese Patent Laid-Open No. Sho-57-77673
Patent Publication 6: Japanese Examined Patent Publication No. Sho-57-60351
Patent Publication 7: Japanese Unexamined Patent Publication No. Hei-3-504855
Patent Publication 8: Japanese Patent Laid-Open No. Sho-49-69677
Patent Publication 9: Japanese Patent Laid-Open No. Sho-51-110572
Patent Publication 10: Japanese Examined Patent Publication No. Sho-52-17030
Patent Publication 11: Japanese Examined Patent Publication No. Sho-55-8984
Patent Publication 12: Japanese Patent Laid-Open No. Sho-48-81869
Patent Publication 13: French Patent No. 1,437,412

DISCLOSURE OF THE INVENTION

Problems to be Solved by the Invention

An object of the present invention is to provide a pharmaceutical composition that has smaller side effects in the central nervous system, such as drowsiness, and excellent action, particularly a useful compound as an active ingredient such as an antihistamine.

Means to Solve the Problems

As a result of intensive studies on antihistamine compounds having the characteristics mentioned above, the present inventors have found that a piperidine derivative represented by the structural formula (I) given below is a compound useful as a medicament that has excellent antihistamine action and alleviates side effects in the central nervous system, such as drowsiness. The present invention has been perfected thereby.

Effects of the Invention

The piperidine derivative of the present invention has an excellent antagonistic action for histamine receptors and shows low brain transfer even in a cerebral receptor binding test where a mouse is orally administered with the compound, and consequently exhibits an effect of alleviating side effects in the central nervous system, such as drowsiness. Therefore, the piperidine derivative has properties desired for active ingredients of pharmaceutical compositions such as antihistamines, and is highly useful.

BEST MODE FOR CARRYING OUT THE INVENTION

The present invention relates to a piperidine derivative, and salt and hydrate thereof that are pharmaceutically acceptable, wherein the piperidine derivative is represented by the following general formula (I):

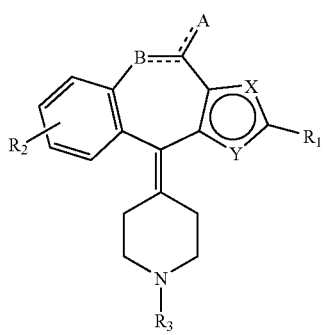

(I)

wherein $R_1$ stands for a hydrogen or a substituent selected from the following (a) to (j):
(a) a halogen,
(b) a cyano,
(c) acrylic acid (including an alkyl ester and a hydroxyalkylamide),
(d) a ureido,
(e) an alkenyl,
(f) an aminoalkyl which may be substituted with an alkylcarbonyl or an aminocarbonyl,
(g) a carbonylalkyl substituted with a hydroxy, an alkoxy or a hydroxyalkylamino,
(h) a carbonyl substituted with a hydroxy, a morpholino, an alkoxy, a hydroxyalkylaminoalkoxy or cyclohexyloxycarbonyloxyalkoxy,
(i) a carbonylamino substituted with an alkyl or an alkoxy,
(j) an aminocarbonyl which may be substituted with one or two substituents selected from an amino, a hydroxy, an alkoxy, an alkenyl, and an alkyl (which may be substituted with a halogen, a thiol, a piperidino, an amino, an alkoxy, an alkoxycarbonyl, an aminocarbonyl, or one or two hydroxys);
$R_2$ stands for a hydrogen or a substituent selected from the following (k) to (s):
(k) a cyano,
(l) acrylic acid (including an alkyl ester and a hydroxyalkylamide),
(m) an alkyl which may be substituted with a hydroxy or a piperidino,
(n) a carbonylalkyl substituted with a hydroxy, an alkoxy (which may be substituted with a cyclohexyloxycarbonyloxy), a piperidino, or a hydroxyalkylamino,
(o) a carbonyl substituted with a hydroxy, an alkoxy, or a hydroxyalkylamino,
(p) a carbonylalkoxy substituted with a hydroxy or an alkoxy,
(q) a carbonylalkylsulfanyl substituted with a hydroxy or an alkoxy,
(r) an alkoxy,
(s) a halogen; and
$R_3$ stands for a hydrogen or a substituent selected from the following (t) to (x):
(t) an alkyl which may be substituted with a carboxy, a cyano, a pyrrolidyl, a piperidino, an alkoxy, an alkylsulfanyl, or one or two hydroxys,
(u) a carbonyl substituted with an alkyl or alkoxy,
(v) a carbonylalkoxyalkyl substituted with a hydroxy or an alkoxy,
(w) a carbonylalkyl substituted with an alkyl, an alkoxy, or an alkylphenyl,
(x) an aminoalkyl substituted with an aminocarbonyl or an alkanesulfonyl, wherein one of the above $R_1$ and $R_2$ stands for a substituent other than a hydrogen, A stands for unsubstituted or an oxo, B stands for a carbon or an oxygen, one of X and Y stands for a carbon and the other stands for a sulfur, a broken line part stands for a single bond or a double bond, with proviso that when $R_2$ stands for a halogen or an alkoxy, A is unsubstituted, $R_1$ stands for a substituent other than a hydrogen, and B stands for an oxygen.

In the above-mentioned general formula (I), the term "alkyl" (including the "alkyl" in an alkyl ester, an alkylphenyl, a hydroxyalkylamide, a hydroxyalkylamino, an alkylcarbonyl, an aminoalkyl, a carbonylalkyl, a hydroxyalkylaminoalkoxy, a hydroxyalkylamino, a carbonylalkoxyalkyl, an alkylsulfanyl, and a carbonylalkylsulfanyl) stands for a linear or branched alkyl group having 1 to 6 carbon atoms, and the alkyl group is preferably, for example, a methyl, an ethyl, a propyl, an isopropyl, a butyl, an isobutyl, a sec-butyl, a t-butyl, a pentyl, an isopentyl, a neopentyl, a t-pentyl, a hexyl, an isohexyl or the like. Also, the alkane moiety of the alkanesulfonyl is a saturated hydrocarbon corresponding to the above alkyl.

The term "alkoxy" (including the "alkoxy" in a hydroxyalkylaminoalkoxy, an alkoxycarbonyl, a carbonylalkoxy, a carbonylalkoxyalkyl, and a cyclohexyloxycarbonyloxyalkoxy) stands for a linear or branched alkoxy group having 1 to 6 carbon atoms, and the alkoxy group is preferably, for example, a methoxy, an ethoxy, an n-propoxy, an isopropoxy, an n-butoxy, an isobutoxy, a sec-butoxy, a t-butoxy, an n-pentyloxy, an n-hexyloxy, or the like.

The term "alkenyl" stands for a linear or branched alkenyl group having 2 to 4 carbon atoms, and the alkenyl group is preferably, for example, a vinyl, an allyl, a propenyl, an isopropenyl, a 1-butenyl, a 2-butenyl, or the like. The term "halogen" stands for a fluorine, a chlorine, a bromine, an iodine, or the like.

The aminoalkyl (f) of $R_1$ may be substituted with an alkylcarbonyl or an aminocarbonyl, or the aminoalkyl (x) of $R_3$ is substituted with an aminocarbonyl or an alkanesulfonyl, and each substituent thereof is substituted at an amino group moiety of the aminoalkyl.

Among the compounds of the present invention, preferred compounds are as follows.

2-Cyano-4-(1-methylpiperidin-4-ylidene)-9,10-dihydro-4H-1-thiabenzo[f]azulene hydrochloride [Compound 1]

2-Bromo-4-(1-methylpiperidin-4-ylidene)-9,10-dihydro-4H-3-thiabenzo[f]azulene hydrobromide [Compound 2]

Ethyl[4-(1-methylpiperidin-4-ylidene)-9,10-dihydro-4H-1-thiabenzo[f]azulen-2-yl]carboxylate [Compound 3]

[4-(1-Methylpiperidin-4-ylidene)-9,10-dihydro-4H-1-thiabenzo[f]azulen-2-yl]carboxylic acid hydrochloride [Compound 4]

[4-(1-Methylpiperidin-4-ylidene)-9,10-dihydro-4H-3-thiabenzo[f]azulen-2-yl]carboxylic acid hydrochloride [Compound 5]

Ethyl 3-[4-(1-methylpiperidin-4-ylidene)-9,10-dihydro-4H-1-thiabenzo[f]azulen-2-yl]acrylate hydrochloride [Compound 6]

3-[4-(1-Methylpiperidin-4-ylidene)-9,10-dihydro-4H-1-thiabenzo[f]azulen-2-yl]acrylic acid hydrochloride [Compound 7]

2-Bromo-4-(1-methylpiperidin-4-ylidene)-4H-1-thiabenzo[f]azulene [Compound 8]

2-Cyano-4-(1-methylpiperidin-4-ylidene)-9,10-dihydro-4H-3-thiabenzo[f]azulene [Compound 9]

2-t-Butoxycarbonylamino-4-(1-methylpiperidin-4-ylidene)-9,10-dihydro-4H-3-thiabenzo[f]azulene [Compound 10]

2-Acetylamino-4-(1-methylpiperidin-4-ylidene)-9,10-dihydro-4H-3-thiabenzo[f]azulene [Compound 11]

2-Aminomethyl-4-(1-methylpiperidin-4-ylidene)-9,10-dihydro-4H-3-thiabenzo[f]azulene dihydrochloride [Compound 12]

2-Acetylaminomethyl-4-(1-methylpiperidin-4-ylidene)-9,10-dihydro-4H-3-thiabenzo[f]azulene hydrochloride [Compound 13]

2-Ureido-4-(1-methylpiperidin-4-ylidene)-9,10-dihydro-4H-3-thiabenzo[f]azulene [Compound 14]

3-[4-(1-Methylpiperidin-4-ylidene)-9,10-dihydro-4H-3-thiabenzo[f]azulen-2-yl]acrylic acid [Compound 15]

2-t-Butoxycarbonylamino-4-(1-methylpiperidin-4-ylidene)-9,10-dihydro-4H-1-thiabenzo[f]azulene [Compound 16]

2-Acetylamino-4-(1-methylpiperidin-4-ylidene)-9,10-dihydro-4H-1-thiabenzo[f]azulene [Compound 17]

2-Ureido-4-(1-methylpiperidin-4-ylidene)-9,10-dihydro-4H-1-thiabenzo[f]azulene [Compound 18]

2-Aminomethyl-4-(1-methylpiperidin-4-ylidene)-9,10-dihydro-4H-1-thiabenzo[f]azulene dihydrochloride [Compound 19]

2-Acetylaminomethyl-4-(1-methylpiperidin-4-ylidene)-9,10-dihydro-4H-1-thiabenzo[f]azulene hydrochloride [Compound 20]

Ethyl[4-(1-methylpiperidin-4-ylidene)-9,10-dihydro-4H-3-thiabenzo[f]azulen-2-yl]carboxylate [Compound 21]

Ethyl 3-[4-(1-methylpiperidin-4-ylidene)-9,10-dihydro-4H-3-thiabenzo[f]azulen-2-yl]acrylate [Compound 22]

Ethyl[4-(1-methylpiperidin-4-ylidene)-9,10-dihydro-4H-3-thiabenzo[f]azulen-2-yl]acetate hydrochloride [Compound 23]

[4-(1-Methylpiperidin-4-ylidene)-9,10-dihydro-4H-3-thiabenzo[f]azulen-2-yl]acetic acid [Compound 24]

6-Cyano-4-(1-methylpiperidin-4-ylidene)-4,10-dihydro-9-oxa-3-thiabenzo[f]azulene [Compound 25]

[4-(1-Methylpiperidin-4-ylidene)-4,10-dihydro-9-oxa-3-thiabenzo[f]azulen-6-yl]carboxylic acid [Compound 26]

[4-(1-Methylpiperidin-4-ylidene)-9,10-dihydro-4H-1-thiabenzo[f]azulen 2-yl]carboxylic acid-N-(2-hydroxyethyl)amide (IUPAC: N-(2-Hydroxyethyl) [4-(1-methylpiperidin-4-ylidene)-9,10-dihydro-4H-1-thiabenzo[f]azulen-2-yl]carboxamide) [Compound 27]

[4-(1-Methylpiperidin-4-ylidene)-9,10-dihydro-4H-1-thiabenzo[f]azulen-2-yl]carboxylic acid-N,N-bis(2-hydroxyethyl)amide hydrochloride (IUPAC: N,N-Bis(2-hydroxyethyl) [4-(1-methylpiperidin-4-ylidene)-9,10-dihydro-4H-1-thiabenzo[f]azulen-2-yl]carboxamide hydrochloride) [Compound 28]

2-(2-Hydroxyethylamino)ethyl[4-(1-methylpiperidin-4-ylidene)-9,10-dihydro-4H-1-thiabenzo[f]azulen-2-yl]carboxylate dihydrochloride [Compound 29]

[4-(1-Methylpiperidin-4-ylidene)-9,10-dihydro-4H-1-thiabenzo[f]azulen-2-yl]carboxylic acid-N-(3-hydroxypropyl)amide (IUPAC: N-(3-Hydroxypropyl) [4-(1-methylpiperidin-4-ylidene)-9,10-dihydro-4H-1-thiabenzo[f]azulen-2-yl]carboxamide) [Compound 30]

[4-(1-Methylpiperidin-4-ylidene)-9,10-dihydro-4H-1-thiabenzo[f]azulen-2-yl]carboxylic acid amide (IUPAC: [4-(1-Methylpiperidin-4-ylidene)-9,10-dihydro-4H-1-thiabenzo[f]azulen-2-yl]carboxamide) [Compound 31]

[4-(1-Methylpiperidin-4-ylidene)-9,10-dihydro-4H-1-thiabenzo[f]azulen-2-yl]acetic acid [Compound 32]

[4-(1-Methylpiperidin-4-ylidene)-9,10-dihydro-4H-1-thiabenzo[f]azulen-2-yl]carboxylic acid-N-[2-(piperidin-1-yl)ethyl]amide dihydrochloride (IUPAC: N-(2-Piperidin-1-yl-ethyl) [4-(1-methylpiperidin-4-ylidene)-9,10-dihydro-4H-1-thiabenzo[1]azulen-2-yl]carboxamide dihydrochloride) [Compound 33]

Ethyl 3-[4-(1-methylpiperidin-4-ylidene)-4,10-dihydro-9-oxa-3-thiabenzo[f]azulen-6-yl]acrylate hydrochloride [Compound 34]

3-[4-(1-Methylpiperidin-4-ylidene)-4,10-dihydro-9-oxa-3-thiabenzo[f]azulen-6-yl]acrylic acid [Compound 35]

Ethyl 3-[4-(1-methylpiperidin-4-ylidene)-4,10-dihydro-9-oxa-3-thiabenzo[f]azulen-2-yl]acrylate hydrochloride [Compound 36]

3-[4-(1-Methylpiperidin-4-ylidene)-4,10-dihydro-9-oxa-3-thiabenzo[f]azulen-2-yl]acrylic acid [Compound 37]

[4-(1-Methylpiperidin-4-ylidene)-9,10-dihydro-4H-1-thiabenzo[f]azulen-2-yl]carboxylic acid-N-(2-methoxyethyl)amide hydrochloride (IUPAC: N-(2-Methoxyethyl)-[4-(1-methylpiperidin-4-ylidene)-9,10-dihydro-4H-1-thiabenzo[f]azulen-2-yl]carboxamide hydrochloride) [Compound 38]

[4-(1-Methylpiperidin-4-ylidene)-9,10-dihydro-4H-1-thiabenzo[f]azulen-2-yl]carboxylic acid-N-(2-aminoethyl)amide dihydrochloride (IUPAC: N-(2-Aminoethyl) [4-(1-methylpiperidin-4-ylidene)-9,10-dihydro-4H-1-thiabenzo[f]azulen-2-yl]carboxamide dihydrochloride) [Compound 39]

[4-(1-Methylpiperidin-4-ylidene)-9,10-dihydro-4H-1-thiabenzo[f]azulen-2-yl]carboxylic acid-N-methoxyamide hydrochloride (IUPAC: N-Methoxy [4-(1-methylpiperidin-4-ylidene)-9,10-dihydro-4H-1-thiabenzo[f]azulen-2-yl]carboxamide hydrochloride) [Compound 40]

[4-(1-Methylpiperidin-4-ylidene)-9,10-dihydro-4H-1-thiabenzo[f]azulen-2-yl]-carboxylic acid-N-(carbamoyl)methylamide (IUPAC: N-{[4-(1-Methylpiperidin-4-ylidene)-9,10-dihydro-4H-1-thiabenzo[f]azulen-2-yl]}carbonyl}aminoacetamide) [Compound 41]

[4-(1-Methylpiperidin-4-ylidene)-9,10-dihydro-4H-1-thiabenzo[f]azulen-2-yl]carboxylic acid-N-acetic acid methyl ester amide hydrochloride (IUPAC: Methyl N-{[4-(1-methylpiperidin-4-ylidene)-9,10-dihydro-4H-1-thiabenzo[f]azulen-2-yl]carbonyl}aminoacetate hydrochloride) [Compound 42]

[4-(1-Methylpiperidin-4-ylidene)-9,10-dihydro-4H-1-thiabenzo[f]azulen-2-yl]carboxylic acid morpholine amide hydrochloride (IUPAC: 4-{[4-(1-Methylpiperidin-4-ylidene)-9,10-dihydro-4H-1-thiabenzo[f]azulen-2-yl]carbonyl}morpholine hydrochloride) [Compound 43]

Ethyl[4-(1-methylpiperidin-4-ylidene)-4,10-dihydro-9-oxa-3-thiabenzo[f]azulen-2-yl]carboxylate hydrochloride [Compound 44]

[4-(1-Methylpiperidin-4-ylidene)-4,10-dihydro-9-oxa-3-thiabenzo[f]azulen-2-yl]carboxylic acid [Compound 45]

3-[4-(1-Methylpiperidin-4-ylidene)-4H-3-thiabenzo[f]azulen-2-yl]acrylic acid [Compound 46]

Ethyl 3-[4-(1-methylpiperidin-4-ylidene)-10-oxo-9,10-dihydro-4H-1-thiabenzo[f]azulen-2-yl]acrylate [Compound 47]

3-[4-(1-Methylpiperidin-4-ylidene)-10-oxo-9,10-dihydro-4H-1-thiabenzo[f]azulen-2-yl]acrylic acid [Compound 48]

2-Ureidomethyl-4-(1-methylpiperidin-4-ylidene)-9,10-dihydro-4H-1-thiabenzo[f]azulene [Compound 49]

Ethyl[4-(1-methylpiperidin-4-ylidene)-10-oxo-9,10-dihydro-4H-1-thiabenzo[f]azulen-2-yl]carboxylate [Compound 50]

[4-(1-Methylpiperidin-4-ylidene)-10-oxo-9,10-dihydro-4H-1-thiabenzo[f]azulen-2-yl]carboxylic acid [Compound 51]

3-[4-(1-Methylpiperidin-4-ylidene)-9,10-dihydro-4H-3-thiabenzo[f]azulen-2-yl]acrylic acid-N-(2-hydroxyethyl)amide (IUPAC: N-(2-Hydroxyethyl)-3-[4-(1-methylpiperidin-4-ylidene)-9,10-dihydro-4H-3-thiabenzo[f]azulen-2-yl]acrylamide) [Compound 52]

[4-(1-Methylpiperidin-4-ylidene)-4,10-dihydro-9-oxa-3-thiabenzo[f]azulen-2-yl]carboxylic acid-N-(2-hydroxyethyl)amide (IUPAC: N-(2-Hydroxyethyl)-[4-(1-methylpiperidin-4-ylidene)-4,10-dihydro-9-oxa-3-thiabenzo[f]azulen-2-yl]carboxamide) [Compound 53]

[4-(1-Methylpiperidin-4-ylidene)-4,10-dihydro-9-oxa-3-thiabenzo[f]azulen-6-yl]acetic acid hydrochloride [Compound 54]

[4-(1-Methylpiperidin-4-ylidene)-4,10-dihydro-9-oxa-3-thiabenzo[f]azulen-2-yl]carboxylic acid-N-(2-hydroxyethyl)amide (IUPAC: N-(2-Hydroxyethyl)-{[4-(1-methylpiperidin-4-ylidene)-4,10-dihydro-9-oxa-3-thiabenzo[f]azulen-2-yl]}carboxamide) [Compound 55]

2-[4-(1-Methylpiperidin-4-ylidene)-9,10-dihydro-4H-1-thiabenzo[f]azulen-2-yl]propionic acid hydrochloride [Compound 56]

2-[4-(1-Methylpiperidin-4-ylidene)-4,10-dihydro-9-oxa-3-thiabenzo[f]azulen-6-yl]propionic acid hydrochloride [Compound 57]

[4-(1-Methylpiperidin-4-ylidene)-4,10-dihydro-9-oxa-3-thiabenzo[f]azulen-2-yl]acetic acid hydrochloride [Compound 58]

[4-(1-Methylpiperidin-4-ylidene)-4H-1-thiabenzo[f]azulen-2-yl]acetic acid hydrochloride [Compound 59]

2-[4-(1-Methylpiperidin-4-ylidene)-9,10-dihydro-4H-3-thiabenzo[f]azulen-2-yl]propionic acid hydrochloride [Compound 60]

Ethyl[4-(1-ethoxycarbonylpiperidin-4-ylidene)-9,10-dihydro-4H-1-thiabenzo[f]azulen-2-yl]carboxylate [Compound 61]

Ethyl[4-(piperidin-4-ylidene)-9,10-dihydro-4H-1-thiabenzo[f]azulen-2-yl]carboxylate [Compound 62]

[4-(1-Methylpiperidin-4-ylidene)-9,10-dihydro-4H-1-thiabenzo[f]azulen-2-yl]acetic acid-N-(2-hydroxyethyl)amide (IUPAC: N-(2-Hydroxyethyl)-{[4-(1-methylpiperidin-4-ylidene)-9,10-dihydro-4H-1-thiabenzo[f]azulen-2-yl]}acetamide) [Compound 63]

2-[4-(1-Methylpiperidin-4-ylidene)-4,10-dihydro-9-oxa-3-thiabenzo[f]azulen-6-yl]propionic acid-N-(2-hydroxyethyl) amide (IUPAC: N-(2-Hydroxyethyl)-{2-[4-(1-methylpiperidin-4-ylidene)-4,10-dihydro-9-oxa-3-thiabenzo[f]azulen-6-yl]}propionamide) [Compound 64]

2-Methyl-2-[4-(1-methylpiperidin-4-ylidene)-9,10-dihydro-4H-1-thiabenzo[f]azulen-2-yl]propionic acid [Compound 65]

3-[4-(1-Methylpiperidin-4-ylidene)-4,10-dihydro-9-oxa-3-thiabenzo[f]azulen-6-yl]acrylic acid-N-(2-hydroxyethyl)amide (IUPAC: N-(2-Hydroxyethyl)-{3-[4-(1-methylpiperidin-4-ylidene)-4,10-dihydro-9-oxa-3-thiabenzo[f]azulen-6-yl]}acrylamide) [Compound 66]

[4-(1-Methylpiperidin-4-ylidene)-9,10-dihydro-4H-3-thiabenzo[f]azulen-2-yl]carboxylic acid-N-(2-hydroxyethyl)amide (IUPAC: N-(2-Hydroxyethyl)-{[4-(1-methylpiperidin-4-ylidene)-9,10-dihydro-4H-3-thiabenzo[f]azulen-2-yl]}carboxamide) [Compound 67]

2-Methyl-2-[4-(1-Methylpiperidin-4-ylidene)-4,10-dihydro-9-oxa-3-thiabenzo[f]azulen-6-yl]propionic acid [Compound 68]

[4-(1-Methylpiperidin-4-ylidene)-9,10-dihydro-4H-1-thiabenzo[f]azulen-2-yl]carboxylic acid-N-(2-hydroxyethyl)-N-methylamide hydrochloride (IUPAC: N-(2-Hydroxyethyl)-N-methyl-{[4-(1-methylpiperidin-4-ylidene)-9,10-dihydro-4H-1-thiabenzo[f]azulen-2-yl]}carboxamide hydrochloride) [Compound 69]

[4-(1-Methylpiperidin-4-ylidene)-9,10-dihydro-4H-1-thiabenzo[f]azulen-2-yl]carboxylic acid-N-(2-hydroxypropyl) amide (IUPAC: N-(2-Hydroxypropyl)-{[4-(1-methylpiperidin-4-ylidene)-9,10-dihydro-4H-1-thiabenzo[f]azulen-2-yl]}carboxamide) [Compound 70]

[4-(1-Methylpiperidin-4-ylidene)-9,10-dihydro-4H-1-thiabenzo[f]azulen-2-yl]carboxylic acid-N-(1-hydroxyprop-2-yl)amide (IUPAC: N-(1-Hydroxyprop-2-yl)-{[4-(1-methylpiperidin-4-ylidene)-9,10-dihydro-4H-1-thiabenzo[f]azulen-2-yl]}carboxamide) [Compound 71]

[4-(1-Methylpiperidin-4-ylidene)-9,10-dihydro-4H-1-thiabenzo[f]azulen-2-yl]carboxylic acid-N-(1,2-dihydroxypropyl)amide (IUPAC: N-(1,2-Dihydroxypropyl)-{[4-(1-methylpiperidin-4-ylidene)-9,10-dihydro-4H-1-thiabenzo[f]azulen-2-yl]}carboxamide) [Compound 72]

[4-(1-Methylpiperidin-4-ylidene)-9,10-dihydro-4H-1-thiabenzo[f]azulen-2-yl]carboxylic acid-N-(1,3-dihydroxyprop-2-yl)amide (IUPAC: N-(1,3-Dihydroxyprop-2-yl)-{[4-(1-methylpiperidin-4-ylidene)-9,10-dihydro-4H-1-thiabenzo[f]azulen-2-yl]}carboxamide) [Compound 73]

[4-(1-Methylpiperidin-4-ylidene)-9,10-dihydro-4H-1-thiabenzo[f]azulen-2-yl]carboxylic acid-N-hydroxy-N-methylamide (IUPAC: N-Hydroxy-N-methyl-{[4-(1-methylpiperidin-4-ylidene)-9,10-dihydro-4H-1-thiabenzo[f]azulen-2-yl]}carboxamide) [Compound 74]

2-Ethoxycarbonylamino-4-(1-methylpiperidin-4-ylidene)-9,10-dihydro-4H-1-thiabenzo[f]azulene [Compound 75]

2-Isopropoxycarbonylamino-4-(1-methylpiperidin-4-ylidene)-9,10-dihydro-4H-1-thiabenzo[f]azulene [Compound 76]

[4-(1-Methylpiperidin-4-ylidene)-9,10-dihydro-4H-1-thiabenzo[f]azulen-2-yl]carboxylic acid-N-(2-fluoroethyl) amide (IUPAC: N-(2-Fluoroethyl)-{[4-(1-methylpiperidin-4-ylidene)-9,10-dihydro-4H-1-thiabenzo[f]azulen-2-yl]}carboxamide) [Compound 77]

[4-(1-Methylpiperidin-4-ylidene)-9,10-dihydro-4H-1-thiabenzo[f]azulen-2-yl]carboxylic acid-N-hydroxyamide (IUPAC: N-Hydroxy-{[4-(1-methylpiperidin-4-ylidene)-9,10-dihydro-4H-1-thiabenzo[f]azulen-2-yl]}carboxamide) [Compound 78]

[4-(1-Methylpiperidin-4-ylidene)-9,10-dihydro-4H-1-thiabenzo[f]azulen-2-yl]carboxylic acid-N-(2,2,2-trifluoroethyl)amide (IUPAC: N-(2,2,2-Trifluoroethyl)-{[4-(1-methylpiperidin-4-ylidene)-9,10-dihydro-4H-1-thiabenzo[f]azulen-2-yl]}carboxamide) [Compound 79]

[4-(1-Methylpiperidin-4-ylidene)-9,10-dihydro-4H-1-thiabenzo[f]azulen-2-yl]carboxylic acid-N-(2-methyl-1-hydroxyprop-2-yl)amide (IUPAC: N-(2-Methyl-1-hydroxyprop-2-yl)-{[4-(1-methylpiperidin-4-ylidene)-9,10-dihydro-4H-1-thiabenzo[f]azulen-2-yl]}carboxamide) [Compound 80]

[4-(1-Methylpiperidin-4-ylidene)-9,10-dihydro-4H-1-thiabenzo[f]azulen-2-yl]carboxylic acid-N-(3,3,3,2,2-pentafluoropropyl)amide (IUPAC: N-(3,3,3,2,2-Pentafluoropropyl)-{[4-(1-methylpiperidin-4-ylidene)-9,10-dihydro-4H-1-thiabenzo[f]azulen-2-yl]}carboxamide) [Compound 81]

[4-(1-Methylpiperidin-4-ylidene)-9,10-dihydro-4H-1-thiabenzo[f]azulen-2-yl]carboxylic acid-N-(2-mercaptoethyl) amide (IUPAC: N-(2-Mercaptoethyl)-{[4-(1-methylpiperidin-4-ylidene)-9,10-dihydro-4H-1-thiabenzo[f]azulen-2-yl]}carboxamide) [Compound 82]

[4-(1-Methylpiperidin-4-ylidene)-9,10-dihydro-4H-1-thiabenzo[f]azulen-2-yl]carboxylic acid-N-amino-N-(2-hydroxyethyl)amide (IUPAC: N-Amino-N-(2-hydroxyethyl)-{[4-(1-methylpiperidin-4-ylidene)-9,10-dihydro-4H-1-thiabenzo[f]azulen-2-yl]}carboxamide) [Compound 83]

[4-(1-Methylpiperidin-4-ylidene)-9,10-dihydro-4H-1-thiabenzo[f]azulen-2-yl]carboxylic acid-N-methyl-N-methoxyamide (IUPAC: N-Methyl-N-methoxy-{[4-(1-methylpiperidin-4-ylidene)-9,10-dihydro-4H-1-thiabenzo[f]azulen-2-yl]}carboxamide) [Compound 84]

[4-(1-Methylpiperidin-4-ylidene)-9,10-dihydro-4H-1-thiabenzo[f]azulen-2-yl]carboxylic acid-N-propylamide (IUPAC: N-Propyl-{[4-(1-methylpiperidin-4-ylidene)-9,10-dihydro-4H-1-thiabenzo[f]azulen-2-yl]}carboxamide) [Compound 85]

[4-(1-Methylpiperidin-4-ylidene)-9,10-dihydro-4H-1-thiabenzo[f]azulen-2-yl]carboxylic acid-N-allyl amide (IUPAC: N-Allyl-{[4-(1-methylpiperidin-4-ylidene)-9,10-dihydro-4H-1-thiabenzo[f]azulen-2-yl]}carboxamide) [Compound 86]

[4-(1-Methylpiperidin-4-ylidene)-10-oxo-9,10-dihydro-4H-1-thiabenzo[f]azulen-2-yl]acetic acid [Compound 87]

[4-(1-Ethoxycarbonylpiperidin-4-ylidene)-9,10-dihydro-4H-1-thiabenzo[f]azulen-2-yl]carboxylic acid [Compound 88]

[4-(1-Methylpiperidin-4-ylidene)-4H-3-thiabenzo[1]azulen-2-yl]carboxylic acid [Compound 89]

Ethyl[4-(1-acetylpiperidin-4-ylidene)-9,10-dihydro-4H-1-thiabenzo[f]azulen-2-yl]carboxylate [Compound 90]

[4-(1-Acetylpiperidin-4-ylidene)-9,10-dihydro-4H-1-thiabenzo[f]azulen-2-yl]carboxylic acid [Compound 91]

Ethyl {4-[1-(2-carboxyethyl)piperidin-4-ylidene]-9,10-dihydro-4H-1-thiabenzo[f]azulen-2-yl}carboxylate [Compound 92]

3-[4-(1-Methylpiperidin-4-ylidene)-9,10-dihydro-4H-3-thiabenzo[f]azulen-2-yl]propionic acid [Compound 93]

{4-[1-(2-Cyanoethyl)piperidin-4-ylidene]-9,10-dihydro-4H-1-thiabenzo[f]azulen-2-yl}carboxylic acid [Compound 94]

Ethyl[4-(1-methylpiperidin-4-ylidene)-9,10-dihydro-4H-1-thiabenzo[f]azulen-6-yl]carboxylate [Compound 95]

[4-(1-Methylpiperidin-4-ylidene)-9,10-dihydro-4H-1-thiabenzo[f]azulen-6-yl]carboxylic acid [Compound 96]

Ethyl 3-[4-(1-methylpiperidin-4-ylidene)-9,10-dihydro-4H-1-thiabenzo[f]azulen-2-yl]propionate [Compound 97]

3-[4-(1-Methylpiperidin-4-ylidene)-9,10-dihydro-4H-1-thiabenzo[f]azulen-2-yl]propionic acid [Compound 98]

3-[4-(1-Methylpiperidin-4-ylidene)-4,10-dihydro-9-oxa-3-thiabenzo[f]azulen-6-yl]propionic acid piperidinamide hydrochloride (IUPAC: 1-{3-[4-(1-Methylpiperidin-4-ylidene)-4,10-dihydro-9-oxa-3-thiabenzo[f]azulen-6-yl]propionyl}piperidine hydrochloride) [Compound 99]

3-[4-(1-Methylpiperidin-4-ylidene)-4,10-dihydro-9-oxa-3-thiabenzo[f]azulen-6-yl]propionic acid [Compound 100]

Ethyl {4-[1-(3-pyrrolidylpropyl)piperidin-4-ylidene]-9,10-dihydro-4H-1-thiabenzo[f]azulen-2-yl}carboxylate dihydrochloride [Compound 101]

{4-[1-(3-pyrrolidylpropyl)piperidin-4-ylidene]-9,10-dihydro-4H-1-thiabenzo[f]azulen-2-yl}carboxylic acid [Compound 102]

Ethyl[4-(1-ethylpiperidin-4-ylidene)-9,10-dihydro-4H-1-thiabenzo[f]azulen-2-yl]carboxylate hydrochloride [Compound 103]

6-(2-Hydroxymethyl)-4-(1-methylpiperidin-4-ylidene)-9,10-dihydro-4H-1-thiabenzo[f]azulene [Compound 104]

Ethyl {4-[1-(2-hydroxyethyl)piperidin-4-ylidene]-9,10-dihydro-4H-1-thiabenzo[f]azulen-2-yl}carboxylate [Compound 105]

Ethyl[4-(1-methylpiperidin-4-ylidene)-9,10-dihydro-4H-1-thiabenzo[f]azulen-6-yl]acetate hydrochloride [Compound 106]

{4-[1-(2-Hydroxyethyl)piperidin-4-ylidene]-9,10-dihydro-4H-1-thiabenzo[f]azulen-2-yl}carboxylic acid hydrochloride [Compound 107]

[4-(1-Ethylpiperidin-4-ylidene)-9,10-dihydro-4H-1-thiabenzo[f]azulen-2-yl]carboxylic acid hydrochloride [Compound 108]

Ethyl {4-{1-[4-(4-t-butylphenyl)-4-oxobutyl]piperidin-4-ylidene}-9,10-dihydro-4H-1-thiabenzo[f]azulen-2-yl}carboxylate [Compound 109]

Ethyl {4-[1-(2-ethoxycarbonylmethoxyethyl)piperidin-4-ylidene]-9,10-dihydro-4H-1-thiabenzo[f]azulen-2-yl}carboxylate hydrochloride [Compound 110]

Ethyl {4-[1-(2-carboxymethoxyethyl)piperidin-4-ylidene]-9,10-dihydro-4H-1-thiabenzo[f]azulen-2-yl}carboxylate [Compound 111]

2-Vinyl-4-(1-methylpiperidin-4-ylidene)-9,10-dihydro-4H-1-thiabenzo[f]azulene [Compound 112]

Ethyl (4-piperidin-4-ylidene-4,10-dihydro-9-oxa-3-thiabenzo[f]azulen-6-yl)acetate hydrochloride [Compound 113]

(4-Piperidin-4-ylidene-4,10-dihydro-9-oxa-3-thiabenzo[f]azulen-6-yl)acetic acid [Compound 114]

Ethyl 4-(1-methylpiperidin-4-ylidene)-9,10-dihydro-4H-3-thiabenzo[f]azulene-6-carboxylate [Compound 115]

Methyl[4-(1-methylpiperidin-4-ylidene)-4,10-dihydro-9-oxa-1-thiabenzo[f]azulen-6-yl]acetate hydrochloride [Compound 116]

[4-(1-Methylpiperidin-4-ylidene)-4,10-dihydro-9-oxa-1-thiabenzo[f]azulen-6-yl]acetic acid [Compound 117]

Methyl {4-[1-(2-hydroxyethyl)piperidin-4-ylidene]-4,10-dihydro-9-oxa-3-thiabenzo[f]azulen-6-yl}acetate hydrochloride [Compound 118]

{4-[1-(2-Hydroxyethyl)piperidin-4-ylidene]-4,10-dihydro-9-oxa-3-thiabenzo[f]azulen-6-yl}acetic acid [Compound 119]

4-[1-(4-Hydroxybutyl)piperidin-4-ylidene]-9,10-dihydro-4H-1-thiabenzo[f]azulene-2-carboxylic acid [Compound 120]

4-(1-Methylpiperidin-4-ylidene)-9,10-dihydro-4H-3-thiabenzo[f]azulene-6-carboxylic acid [Compound 121]

2-{4-[1-(2-Hydroxyethyl)piperidin-4-ylidene]-4,10-dihydro-9-oxa-3-thiabenzo[f]azulen-6-yl}ethanol [Compound 122]

Methyl 4-[4-(1-methylpiperidin-4-ylidene)-4,10-dihydro-9-oxa-3-thiabenzo[f]azulen-6-yl]butyrate hydrochloride [Compound 123]

4-[4-(1-Methylpiperidin-4-ylidene)-4,10-dihydro-9-oxa-3-thiabenzo[f]azulen-6-yl]butyric acid [Compound 124]

3-[4-(6-Carboxymethyl-10H-9-oxa-3-thiabenzo[f]azulen-4-ylidene)piperidin-1-yl]propionic acid [Compound 125]

Methyl (4-piperidin-4-ylidene-4,10-dihydro-9-oxa-3-thiabenzo[f]azulen-6-yl)acetate hydrochloride [Compound 126]

Methyl[4-(1-ethylpiperidin-4-ylidene)-4,10-dihydro-9-oxa-3-thiabenzo[f]azulen-6-yl]acetate hydrochloride [Compound 127]

[4-(1-Ethylpiperidin-4-ylidene)-4,10-dihydro-9-oxa-3-thiabenzo[f]azulen-6-yl]acetic acid [Compound 128]

Methyl[4-(1-propylpiperidin-4-ylidene)-4,10-dihydro-9-oxa-3-thiabenzo[f]azulen-6-yl]acetate hydrochloride [Compound 129]

[4-(1-Propylpiperidin-4-ylidene)-4,10-dihydro-9-oxa-3-thiabenzo[f]azulen-6-yl]acetic acid [Compound 130]

Methyl[4-(1-isopropylpiperidin-4-ylidene)-4,10-dihydro-9-oxa-3-thiabenzo[f]azulen-6-yl]acetate hydrochloride [Compound 131]

[4-(1-Isopropylpiperidin-4-ylidene)-4,10-dihydro-9-oxa-3-thiabenzo[f]azulen-6-yl]acetic acid [Compound 132]

Ethyl 4-(1-propylpiperidin-4-ylidene)-9,10-dihydro-4H-1-thiabenzo[f]azulene-2-carboxylate hydrochloride [Compound 133]

4-(1-Propylpiperidin-4-ylidene)-9,10-dihydro-4H-1-thiabenzo[f]azulene-2-carboxylic acid hydrochloride [Compound 134]

Methyl 4-(4-piperidin-4-ylidene-4,10-dihydro-9-oxa-3-thiabenzo[f]azulen-6-yl)butyrate hydrochloride [Compound 135]

4-(4-piperidin-4-ylidene-4,10-dihydro-9-oxa-3-thiabenzo[f]azulen-6-yl)butyric acid hydrochloride [Compound 136]

Propyl (4-piperidin-4-ylidene-4,10-dihydro-9-oxa-3-thiabenzo[f]azulen-6-yl)acetate hydrochloride [Compound 137]

Methyl {4-[1-(3-hydroxypropyl)piperidin-4-ylidene]-4,10-dihydro-9-oxa-3-thiabenzo[f]azulen-6-yl}acetate hydrochloride [Compound 138]

{4-[1-(3-Hydroxypropyl)piperidin-4-ylidene]-4,10-dihydro-9-oxa-3-thiabenzo[f]azulen-6-yl}acetic acid [Compound 139]

Ethyl[4-(1-methylpiperidin-4-ylidene)-4,10-dihydro-9-oxa-3-thiabenzo[f]azulen-6-yl]acetate hydrochloride [Compound 140]

Methyl 4-[4-(1-ethylpiperidin-4-ylidene)-4,10-dihydro-9-oxa-3-thiabenzo[f]azulen-6-yl]butyrate hydrochloride [Compound 141]

4-[4-(1-Ethylpiperidin-4-ylidene)-4,10-dihydro-9-oxa-3-thiabenzo[f]azulen-6-yl]butyric acid [Compound 142]

Ethyl 3-(4-piperidin-4-ylidene-4,10-dihydro-9-oxa-3-thiabenzo[f]azulen-6-yl)acrylate hydrochloride [Compound 143]

3-(4-Piperidin-4-ylidene-4,10-dihydro-9-oxa-3-thiabenzo[f]azulen-6-yl)acrylic acid [Compound 144]

Ethyl 3-(4-piperidin-4-ylidene-9,10-dihydro-4H-1-thiabenzo[f]azulen-2-yl)acrylate hydrochloride [Compound 145]

3-(4-Piperidin-4-ylidene-9,10-dihydro-4H-1-thiabenzo[f]azulen-2-yl)acrylic acid [Compound 146]

Ethyl[4-(1-methylpiperidin-4-ylidene)-9,10-dihydro-4H-3-thiabenzo[f]azulen-6-yl]acetate hydrochloride [Compound 147]

[4-(1-Methylpiperidin-4-ylidene)-9,10-dihydro-4H-3-thiabenzo[f]azulen-6-yl]acetic acid hydrochloride [Compound 148]

Ethyl 4-(1-isopropylpiperidin-4-ylidene)-9,10-dihydro-4H-1-thiabenzo[f]azulene-2-carboxylate hydrochloride [Compound 149]

4-(1-Isopropylpiperidin-4-ylidene)-9,10-dihydro-4H-1-thiabenzo[f]azulene-2-carboxylic acid [Compound 150]

[4-(1-Methylpiperidin-4-ylidene)-9,10-dihydro-4H-1-thiabenzo[f]azulen-6-yl]acetic acid [Compound 151]

Ethyl 2-methyl-2-(4-piperidin-4-ylidene-9,10-dihydro-4H-1-thiabenzo[f]azulen-2-yl)propionate hydrochloride [Compound 152]

2-Methyl-2-(4-piperidin-4-ylidene-9,10-dihydro-4H-1-thiabenzo[f]azulen-2-yl)propionic acid hydrochloride [Compound 153]

Ethyl 2-[4-(1-ethylpiperidin-4-ylidene)-9,10-dihydro-4H-1-thiabenzo[f]azulen-2-yl]-2-methylpropionate hydrochloride [Compound 154]

2-[4-(1-Ethylpiperidin-4-ylidene)-9,10-dihydro-4H-1-thiabenzo[f]azulen-2-yl]-2-methylpropionic acid [Compound 155]

Methyl 5-[4-(1-methylpiperidin-4-ylidene)-4,10-dihydro-9-oxa-3-thiabenzo[f]azulen-6-yl]valerate hydrochloride [Compound 156]

5-[4-(1-Methylpiperidin-4-ylidene)-4,10-dihydro-9-oxa-3-thiabenzo[f]azulen-6-yl]valeric acid [Compound 157]

Ethyl 3-[4-(1-ethylpiperidin-4-ylidene)-9,10-dihydro-4H-1-thiabenzo[f]azulen-2-yl]acrylate [Compound 158]

3-[4-(1-Ethylpiperidin-4-ylidene)-9,10-dihydro-4H-1-thiabenzo[f]azulen-2-yl]acrylic acid hydrochloride [Compound 159]

Ethyl 4-(1-ethylpiperidin-4-ylidene)-9,10-dihydro-4H-3-thiabenzo[f]azulene-6-carboxylate [Compound 160]

4-(1-Ethylpiperidin-4-ylidene)-9,10-dihydro-4H-3-thiabenzo[f]azulene-6-carboxylic acid [Compound 161]

5-(4-Piperidin-4-ylidene-4,10-dihydro-9-oxa-3-thiabenzo[f]azulen-6-yl)valeric acid [Compound 162]

Methyl {4-[1-(3-piperidin-1-yl-propyl)piperidin-4-ylidene]-4,10-dihydro-9-oxa-3-thiabenzo[f]azulen-6-yl}acetate dihydrochloride [Compound 163]

{4-[1-(3-Piperidin-1-ylpropyl)piperidin-4-ylidene]-4,10-dihydro-9-oxa-3-thiabenzo[f]azulen-6-yl}acetic acid [Compound 164]

Methyl[4-(1-methylpiperidin-4-ylidene)-4,10-dihydro-9-oxa-3-thiabenzo[f]azulen-6-yloxy]acetate hydrochloride [Compound 165]

[4-(1-Methylpiperidin-4-ylidene)-4,10-dihydro-9-oxa-3-thiabenzo[f]azulen-6-yloxy]acetic acid [Compound 166]

Methyl {4-[1-(2-oxopropyl)piperidin-4-ylidene]-4,10-dihydro-9-oxa-3-thiabenzo[f]azulen-6-yl}acetate hydrochloride [Compound 167]

{4-[1-(2-Oxopropyl)piperidin-4-ylidene]-4,10-dihydro-9-oxa-3-thiabenzo[f]azulen-6-yl}acetic acid [Compound 168]

Methyl {4-[1-(4-oxopentyl)piperidin-4-ylidene]-4,10-dihydro-9-oxa-3-thiabenzo[f]azulen-6-yl}acetate hydrochloride [Compound 169]

{4-[1-(4-Oxopentyl)piperidin-4-ylidene]-4,10-dihydro-9-oxa-3-thiabenzo[f]azulen-6-yl}acetic acid [Compound 170]

Methyl[4-(1-methylpiperidin-4-ylidene)-4,10-dihydro-9-oxa-3-thiabenzo[f]azulen-6-ylsulfanyl]acetate hydrochloride [Compound 171]

[4-(1-Methylpiperidin-4-ylidene)-4,10-dihydro-9-oxa-3-thiabenzo[f]azulen-6-ylsulfanyl]acetic acid [Compound 172]

Ethyl 3-[4-(6-methoxycarbonylmethyl-10H-9-oxa-3-thiabenzo[f]azulen-4-ylidene)piperidin-1-yl]propionate hydrochloride [Compound 173]

Methyl {4-[1-(2-ureidoethyl)piperidin-4-ylidene]-4,10-dihydro-9-oxa-3-thiabenzo[f]azulen-6-yl}acetate [Compound 174]

{4-[1-(2-Ureidoethyl)piperidin-4-ylidene]-4,10-dihydro-9-oxa-3-thiabenzo[f]azulen-6-yl}acetic acid [Compound 175]

1-Cyclohexyloxycarbonyloxyethyl 4-(1-methylpiperidin-4-ylidene)-9,10-dihydro-4H-1-thiabenzo[f]azulene-2-carboxylate hydrochloride [Compound 176]

Methyl {4-[1-(2-methanesulfonylaminoethyl)piperidin-4-ylidene]-4,10-dihydro-9-oxa-3-thiabenzo[f]azulen-6-yl}acetate hydrochloride [Compound 177]

{4-[1-(2-Methanesulfonylaminoethyl)piperidin-4-ylidene]-4,10-dihydro-9-oxa-3-thiabenzo[f]azulen-6-yl}acetic acid [Compound 178]

t-Butyl 4-(6-carboxymethyl-10H-9-oxa-3-thiabenzo[f]azulen-4-ylidene)piperidine-1-carboxylate [Compound 179]
1-Cyclohexyloxycarbonyloxyethyl (4-piperidin-4-ylidene-4,10-dihydro-9-oxa-3-thiabenzo[f]azulen-6-yl)acetate hydrochloride [Compound 180]
Ethyl 4-[1-(2-ethoxyethyl)piperidin-4-ylidene]-9,10-dihydro-4H-1-thiabenzo[f]azulene-2-carboxylate hydrochloride [Compound 181]
4-[1-(2-Ethoxyethyl)piperidin-4-ylidene]-9,10-dihydro-4H-1-thiabenzo[f]azulene-2-carboxylic acid [Compound 182]
1-Methyl-4-[6-(2-piperidin-1-ylethyl)-10H-9-oxa-3-thiabenzo[f]azulen-4-ylidene]piperidine dihydrochloride [Compound 183]
Methyl 4-{1-[1-(2,3-dihydroxypropyl)piperidin-4-ylidene]-4,10-dihydro-9-oxa-3-thiabenzo[f]azulen-6-yl}butyrate hydrochloride [Compound 184]
4-{4-[1-(2,3-Dihydroxypropyl)piperidin-4-ylidene]-4,10-dihydro-9-oxa-3-thiabenzo[f]azulen-6-yl}butyric acid [Compound 185]
3-{-4-[6-(2-Piperidin-1-ylethyl)-10H-9-oxa-3-thiabenzo[f]azulen-4-ylidene]piperidin-1-yl}propionic acid [Compound 186]
Methyl 4-{4-[1-(4-oxopentyl)piperidin-4-ylidene]-4,10-dihydro-9-oxa-3-thiabenzo[f]azulen-6-yl}butyrate hydrochloride [Compound 187]
4-{4-[1-(4-Oxopentyl)piperidin-4-ylidene]-4,10-dihydro-9-oxa-3-thiabenzo[f]azulen-6-yl}butyric acid [Compound 188]
Methyl 2-methyl-2-[4-(1-methylpiperidin-4-ylidene)-4,10-dihydro-9-oxa-3-thiabenzo[f]azulen-6-ylsulfanyl]propionate hydrochloride [Compound 189]
2-Methyl-2-[4-(1-methylpiperidin-4-ylidene)-4,10-dihydro-9-oxa-3-thiabenzo[f]azulen-6-ylsulfanyl]propionic acid hydrochloride [Compound 190]
Methyl {4-[1-(3-oxobutyl)piperidin-4-ylidene]-4,10-dihydro-9-oxa-3-thiabenzo[f]azulen-6-yl}acetate hydrochloride [Compound 191]
{4-[1-(3-Oxobutyl)piperidin-4-ylidene]-4,10-dihydro-9-oxa-3-thiabenzo[f]azulen-6-yl}acetic acid [Compound 192]
Methyl {4-[1-(3-methanesulfonylaminopropyl)piperidin-4-ylidene]-4,10-dihydro-9-oxa-3-thiabenzo[f]azulen-6-yl}acetate hydrochloride [Compound 193]
{4-[1-(3-Methanesulfonylaminopropyl)piperidin-4-ylidene]-4,10-dihydro-9-oxa-3-thiabenzo[f]azulen-6-yl}acetic acid [Compound 194]
Methyl 3-{4-[1-(2-methanesulfonylaminoethyl)piperidin-4-ylidene]-4,10-dihydro-9-oxa-3-thiabenzo[f]azulen-6-yl}propionate hydrochloride [Compound 195]
3-{4-[1-(2-Methanesulfonylaminoethyl)piperidin-4-ylidene]-4,10-dihydro-9-oxa-3-thiabenzo[f]azulen-6-yl}propionic acid [Compound 196]
Methyl (4-piperidin-4-ylidene-4,10-dihydro-9-oxa-3-thiabenzo[f]azulen-6-ylsulfanyl)acetate hydrochloride [Compound 197]
Methyl {4-[1-(3-methylsulfanylpropyl)piperidin-4-ylidene]-4,10-dihydro-9-oxa-3-thiabenzo[f]azulen-6-yl}acetate hydrochloride [Compound 198]
{4-[1-(3-Methylsulfanylpropyl)piperidin-4-ylidene]-4,10-dihydro-9-oxa-3-thiabenzo[f]azulen-6-yl}acetic acid [Compound 199]
Methyl {4-[1-(2-methylsulfanylethyl)piperidin-4-ylidene]-4,10-dihydro-9-oxa-3-thiabenzo[f]azulen-6-yl}acetate hydrochloride [Compound 200]
{4-[1-(2-Methylsulfanylethyl)piperidin-4-ylidene]-4,10-dihydro-9-oxa-3-thiabenzo[f]azulen-6-yl}acetic acid [Compound 201]
2-Methyl-2-[4-(1-propylpiperidin-4-ylidene)-4,10-dihydro-9-oxa-3-thiabenzo[f]azulen-6-ylsulfanyl]propionic acid hydrochloride [Compound 202]
3-(4-Piperidin-4-ylidene-9,10-dihydro-4H-3-thiabenzo[f]azulen-2-yl)acrylic acid [Compound 203]
[6-Fluoro-4-(1-methylpiperidin-4-ylidene)-4,10-dihydro-9-oxa-3-thiabenzo[f]azulen-2-yl]acetic acid [Compound 204]
[6-Chloro-4-(1-methylpiperidin-4-ylidene)-4,10-dihydro-9-oxa-3-thiabenzo[f]azulen-2-yl]acetic acid [Compound 205]
2-[6-Chloro-4-(1-methylpiperidin-4-ylidene)-4,10-dihydro-9-oxa-3-thiabenzo[f]azulen-2-yl]-2-methylpropionic acid [Compound 206]
[6-Methoxy-4-(1-methylpiperidin-4-ylidene)-4,10-dihydro-9-oxa-3-thiabenzo[f]azulen-2-yl]acetic acid [Compound 207]
[6-Methyl-4-(1-methylpiperidin-4-ylidene)-4,10-dihydro-9-oxa-3-thiabenzo[f]azulen-2-yl]acetic acid [Compound 208]
3-(4-Piperidin-4-ylidene-4H-1-thiabenzo[f]azulen-2-yl)propionic acid [Compound 209]
3-(4-Piperidin-4-ylidene-4H-3-thiabenzo[f]azulen-2-yl)propionic acid [Compound 210]
4-Piperidin-4-ylidene-9,10-dihydro-4H-3-thiabenzo[f]azulene-6-carboxylic acid [Compound 211]
4-(2-Bromo-9,10-dihydro-1-thiabenzo[f]azulen-4-ylidene)-1-methylpiperidine [Compound 212]

Among the compounds of the present invention, in the above-mentioned general formula (I), a compound in which one of $R_1$ and $R_2$ stands for a hydrogen is preferred, and more preferred compounds include the compounds listed in Tables 18 and 19 set forth later. Further, compounds listed in Table 21 having excellent anti-histamine actions and low brain transfer are especially preferred.

A general method for producing the compound of the present invention will be given hereinbelow. The compound of the present invention represented by the above-mentioned general formula (I) can be produced according to the method described below. Here, it is obvious for one of ordinary skill in the art that the exact methods usable in the production of specified compounds can vary depending upon their chemical structures.

Of the above-mentioned compounds of the present invention represented by the above-mentioned general formula (I), a 4-(piperidin-4-ylidene)-9,10-dihydro-4H-1-thiabenzo[f] azulene compound can be produced in accordance with a method described in Japanese Patent Laid-Open No. Sho-49-69677; a 4-(piperidin-4-ylidene)-4H-1-thiabenzo[f]azulene compound can be produced in accordance with methods described in Japanese Patent Laid-Open No. Sho-49-69677 and *Helvetica Chimica Acta,* 49, Fasc. Emile Cherbuliez (1966) No. 26, 214-234; a 4-(piperidin-4-ylidene)-9,10-dihydro-4H-3-thiabenzo[f]azulene compound can be produced in accordance with a method described in *Helvetica Chimica Acta,* 54, Fasc. 1 (1971), 277-282; a 4-(piperidin-4-ylidene)-4H-3-thiabenzo[f]azulene compound can be produced in accordance with methods described in Japanese Patent Laid-Open No. Sho-49-69677, *Helvetica Chimica Acta,* 49, Fasc. Emile Cherbuliez (1966) No. 26, 214-234, and *Helvetica Chimica Acta,* 54, Fasc. 1 (1971), 277-282; a 4-(piperidin-4-ylidene)-10-oxo-9,10-dihydro-4H-1-thiabenzo[f]azulene compound can be produced in accordance a method described in *Helvetica Chimica Acta,* 59, Fasc. 3 (1976), 866-877; and a 4-(piperidin-4-ylidene)-4,10-dihydro-9-oxa-1-thiabenzo[f]azulene compound and a 4-(piperidin-4- ylidene)-4,10-dihydro-9-oxa-3-thiabenzo[f]azulene compound can be produced in accordance methods described in WO 2005/003131.

The formation of the functional groups on the aromatic ring can be accomplished by bromination with bromine or NBS (N-bromosuccimide), lithio-formation reaction with an alkyllithium reagent, a Friedel-Crafts acylation reaction, a Vilsmeier formylation reaction, or the like. Further, the brominated compound can be subjected to a carbonylation reaction, a Fleck reaction, a cyanation reaction, a formylation reaction, an Ullmann reaction, a Suzuki coupling reaction, or the like, with properly using a transition metal catalyst such as palladium to introduce a desired functional group. Alternatively, compounds can be synthesized by selecting a starting raw material previously having any substituent at a position corresponding thereto.

(1) Case where A is Unsubstituted

General methods for producing a 4-(piperidin-4-ylidene)-9,10-dihydro-4H-1-thiabenzo[f]azulene compound, a 4-(piperidin-4-ylidene)-4H-1-thiabenzo[f]azulene compound, a 4-(piperidin-4-ylidene)-9,10-dihydro-4H-3-thiabenzo[f]azulene compound, a 4-(piperidin-4-ylidene)-4H-3-thiabenzo[f]azulene compound, a 4-(piperidin-4-ylidene)-4,10-dihydro-9-oxa-1-thiabenzo[f]azulene compound, and a 4-(piperidin-4-ylidene)-4,10-dihydro-9-oxa-3-thiabenzo[f]azulene compound, each of the general formula (II) will be given hereinbelow. The compounds represented by the general formula (II) are obtained by an alkylation reaction, an Ullmann reaction, or a Michael reaction of a compound represented by the general formula (III). For example, an alkylation reaction is carried out with an alkyl halide or the like in a solvent such as acetone, benzene, or DMF (dimethylformamide) at a suitable temperature between room temperature and a boiling point of the solvent, in the presence of a base such as potassium carbonate, sodium hydride, or potassium butoxide.

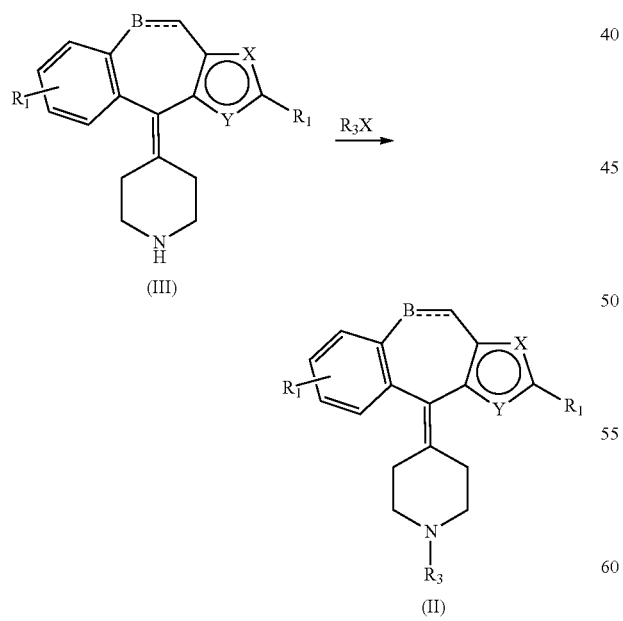

The compound represented by the general formula (III) is obtained by an alkali hydrolysis, hydrobromic acid decomposition, or reducing reaction of a compound represented by the general formula (IV). For example, the alkali hydrolysis reaction is carried out by refluxing while heating in a solvent such as butanol or isopropanol, in the presence of a strong base such as sodium hydroxide or potassium hydroxide.

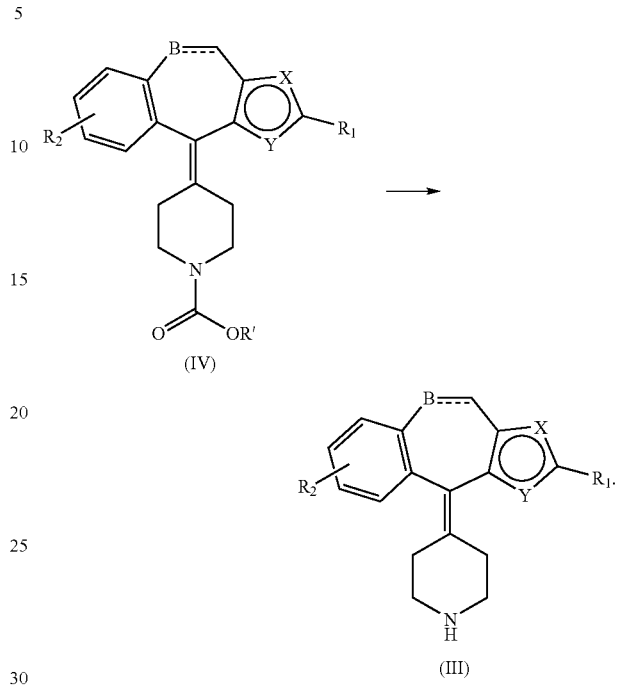

The compound represented by the general formula (IV) can be synthesized by a carbonylation reaction of a compound represented by the general formula (V). For example, the reaction is carried out by refluxing while heating in a solvent such as benzene or dichloroethane, in the presence of ethyl chloroformate or 2,2,2-trichloroethyl chloroformate.

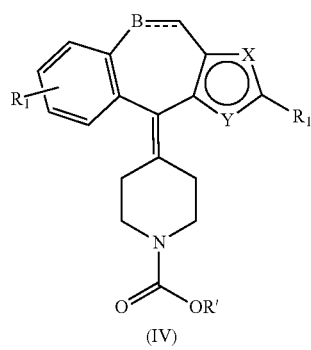

The compound represented by the general formula (V) can be obtained by subjecting a compound represented by the general formula (VI) to a cyanation reaction, a carbonylation reaction, a Heck reaction, an alkylation reaction, or a formylation reaction with properly using a palladium catalyst, or alternatively converting a compound represented by the general formula (VI) to a boric acid compound and subjecting the compound to a Suzuki coupling reaction. For example, a cyanation reaction can be carried out with a ligand such as DPPF (1,1'-bis(diphenylphosphino)ferrocene), PPh$_3$ (triphenylphosphine), P (o-tol)$_3$(tris(2-methylphenyl)phosphine), P(t-Bu)$_3$ (tri-tert-butylphosphine), or N,N'-(2,6-diisopropylphenyl)dihydroimidazolium chloride, using copper cyanide, zinc cyanide, iron ferrocyanide, or sodium cyanide, in the presence of Pd(dba)$_2$ (palladium(0) bis(dibenzylidene acetone)), Pd$_2$(dba)$_3$ (dipalladium(0) tris(dibenzylidene acetone)), Pd(OAc)$_2$ (palladium(II) acetate), or Pd(PPh$_3$)$_4$ (palladium(0) tetrakis(triphenylphosphine)). The reaction can be carried out in a compatible solvent, such as DMF, water, acetone, acetonitrile, toluene, THF (tetrahydrofuran), or a mixture thereof, at a suitable temperature, preferably at a temperature between room temperature and a boiling point of the solvent.

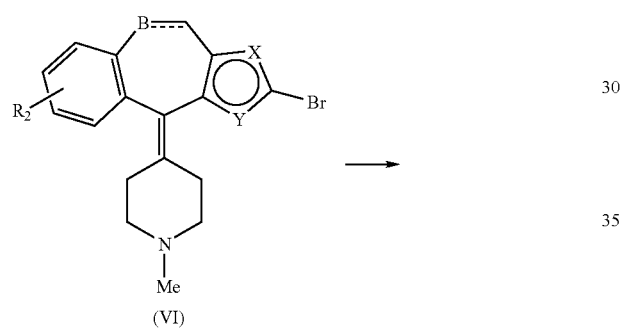

(VI)

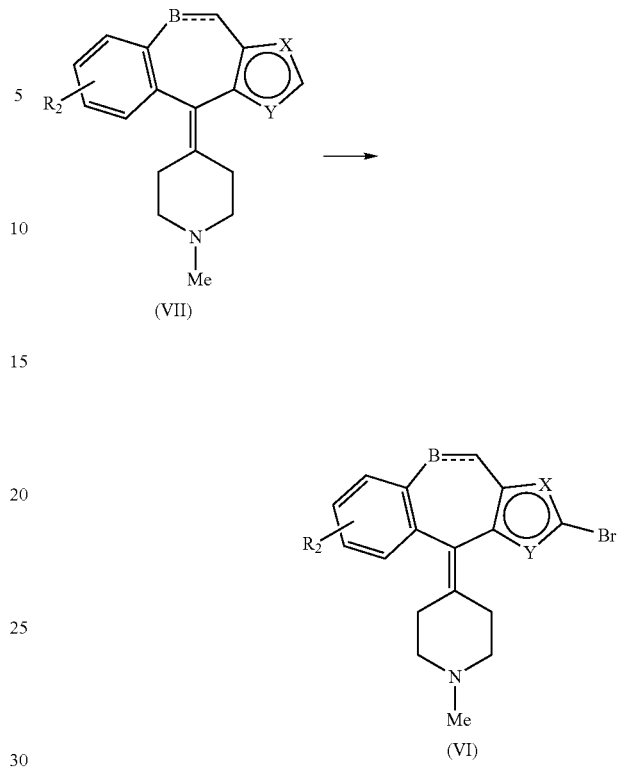

(VII)

(VI)

The compound represented by the general formula (VII) is obtained by subjecting a product after a Grignard reaction of a compound represented by the general formula (VIII) to a dehydration reaction or a McMurry reaction. For example, a Grignard reaction is carried out by treating a compound represented by the general formula (VIII) with a Grignard reagent prepared from magnesium and 4-chloro-N-methylpiperidine, in a non-aqueous solvent such as THF or toluene at a suitable temperature from a melting point to a boiling point of the solvent. The subsequent dehydration reaction can be carried out with hydrochloric acid, trifluoroacetic acid, thionyl chloride or the like, in the absence of a solvent or in a suitable solvent such as water, ethanol, or dichloromethane, at an optimal reaction temperature from a melting point to a boiling point of the solvent. The compound represented by the general formula (VIII) can be synthesized in accordance with methods described in Japanese Patent Laid-Open No. Sho-49-69677, *Helvetica Chimica Acta*, 54, Fasc. 1 (1971), 277-282, and WO 2005/003131.

(V)

The compound represented by the general formula (VI) is obtained by bromination of a compound represented by the general formula (VII). As a bromination agent, bromine, NBS or the like can be used. The reaction can be carried out in a compatible solvent such as acetic acid, chloroform, carbon tetrachloride, ethyl acetate, methanol, or a mixture thereof at a suitable temperature, preferably a temperature between 0° C. and a boiling point of the solvent.

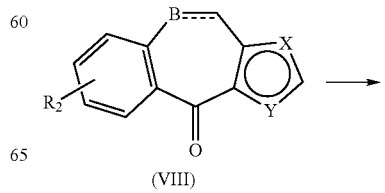

(VIII)

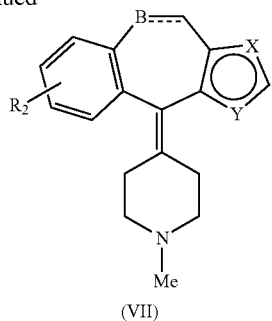

(VII)

(2) Case where A is Oxo

A 4-(piperidin-4-ylidene)-10-oxo-9,10-dihydro-4H-1-thiazobenzo[f]azulene compound represented by the general formula (IX) is obtained by concurrently subjecting a compound represented by the formula (X) to a hydrolysis reaction of methyl enol ether and a dehydration reaction of an alcohol. This reaction can be carried out with an inorganic acid such as hydrochloric acid, or an organic acid in a water-containing solvent such as water or ethanol, at a temperature between room temperature and a boiling point.

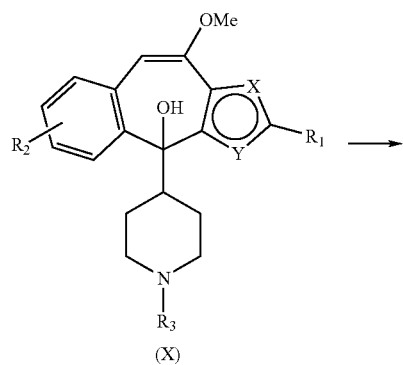

(X)

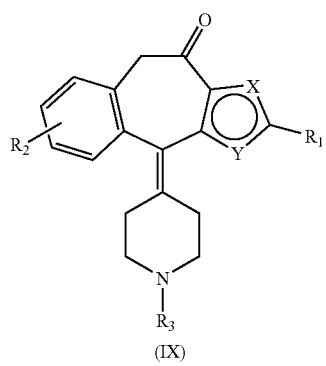

(IX)

The compound represented by the general formula (X) can be obtained by subjecting a compound represented by the general formula (XI) to a cyanation reaction, a carbonylation reaction, a Heck reaction, an alkylation reaction, or a formylation reaction with properly using a palladium catalyst, or converting a compound represented by the general formula (XI) to a boric acid compound and subjecting the compound to a Suzuki coupling reaction. For example, a cyanation reaction can be carried out with a ligand such as DPPF, PPh$_3$, P(o-tol)$_3$, P(t-Bu)$_3$, or N,N'-(2,6-diisopropylphenyl)dihydroimidazolium chloride, using copper cyanide, zinc cyanide, iron ferrocyanide, or sodium cyanide, in the presence of Pd(dba)$_2$, Pd$_2$(dba)$_3$, Pd(OAc)$_2$, or Pd(PPh$_3$)$_4$. The reaction can be carried out in a compatible solvent, such as DMF, water, acetone, acetonitrile, toluene, THF, or a mixture thereof, at a suitable temperature, preferably at a temperature between room temperature and a boiling point of the solvent.

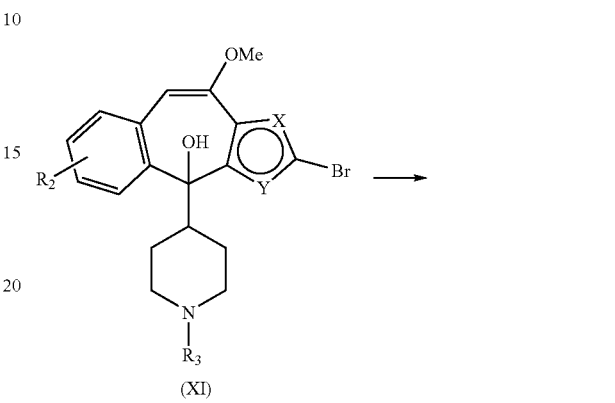

(XI)

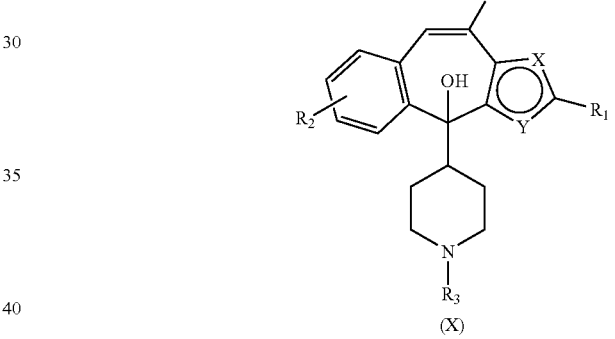

(X)

The compound represented by the general formula (XI) is obtained by subjecting a compound represented by the general formula (XII) to a Grignard reaction or the like. For example, a Grignard reaction can be carried out by treating a compound represented by the general formula (XII) with a Grignard reagent prepared from magnesium and 4-chloro-N-methylpiperidine, in a non-aqueous solvent such as THF or toluene at a suitable temperature from a melting point to a boiling point of the solvent.

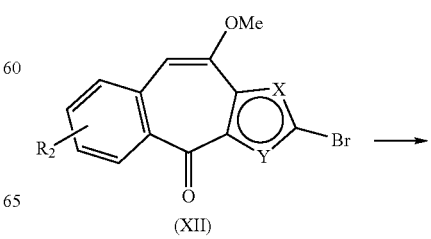

(XII)

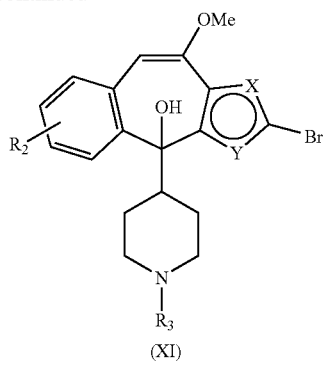

(XI)

The compound represented by the general formula (XII) can be obtained by a β-elimination reaction or the like, which is carried out subsequent to subjecting a compound represented by the general formula (XIII) to a methanol decomposition reaction, For example, the methanol decomposition is carried out by refluxing while heating in methanol. The β-elimination reaction can be carried out with a base such as DSU (1,8-diazabicyclo[5,4,0]und-7-ene), triethylamine, or potassium butoxide, in a solvent such as THF, benzene, toluene, or methanol at a suitable temperature from room temperature to a boiling point of the solvent.

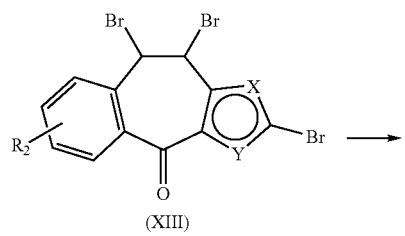

(XIII)

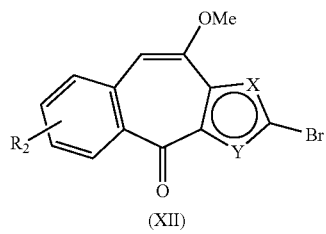

(XII)

The compound represented by the general formula (XIII) is synthesized by subjecting a compound represented by the general formula (XIV) to a bromination reaction or the like with NBS or the like. For example, the bromination reaction is carried out by refluxing while heating using benzoyl peroxide or the like as an initiator in a small amount in an appropriate solvent such as chloroform, carbon tetrachloride, dichloroethane, or toluene.

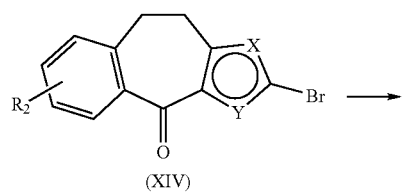

(XIV)

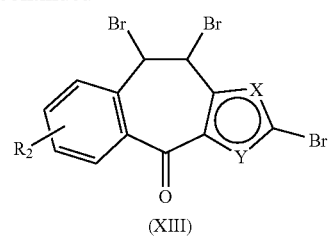

(XIII)

The compound represented by the general formula (XIV) is synthesized by subjecting a compound represented by the general formula (XV) to bromination or the like with bromine. The bromination is carried out in a solvent such as chloroform, acetic acid, or methanol at a suitable temperature from a melting point to a boiling point of the solvent.

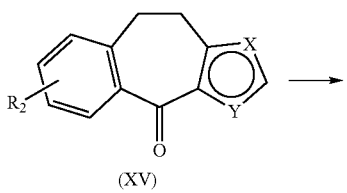

(XV)

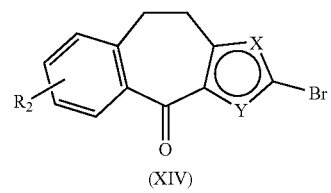

(XIV)

The compound represented by the general formula (XV) is synthesized by subjecting a compound represented by the general formula (XVI) to an intramolecular Friedel-Crafts reaction or the like. For example, the intramolecular Friedel-Crafts reaction can be carried by subjecting a carboxylic acid itself, or a product after converting the acid to an acid chloride or a mixed acid anhydride, to a reaction in the presence of, if necessary, a Lewis acid such as polyphosphoric acid, aluminum chloride, titanium chloride, tin chloride, or $BF_3 \cdot OEt_2$ (boron trifluoride.diethyl ether complex), appropriately using a solvent such as THF, dichloromethane, chloroform, dichloroethane, carbon disulfide, or nitrobenzene, at an optimal temperature between a melting point of the solvent to 300° C.

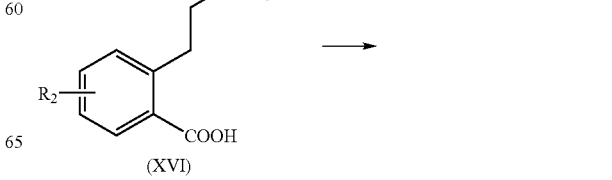

(XVI)

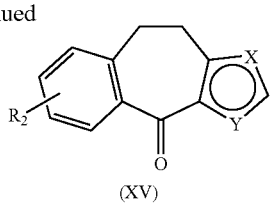

The compound represented by the general formula (XVI) can be synthesized by subjecting a compound represented by the general formula (XVII) to an Aldol reaction, a Wittig reaction, a Wittig-Horner reaction, a Peterson reaction, or the like. For example, in a case where a Wittig reaction is used, a compound represented by the general formula (XVII) is treated with NBS to brominate a methyl group, and then treated with triphenylphosphine to form a phosphonium salt. At this time, a bromination reaction is carried out by refluxing while heating using benzoyl peroxide or the like as a reaction initiator in a small amount, in a solvent such as carbon tetrachloride or dichloroethane. The reaction of benzyl bromide obtained by the bromination reaction with triphenylphosphine is carried out by heating in a solvent such as benzene, toluene, or dichloroethane. The resulting phosphonium salt can be converted to a compound represented by the formula (XVI) by treating the phosphonium salt with a base such as butoxypossium or sodium hydride to form an ylide, condensing the ylide with thiophene aldehyde, and finally reducing a double bond of the condensate. At this time, the treatment of the phosphonium salt with thiophene aldehyde is carried out in a solvent such as THF, acetonitrile, benzene, or toluene, at a suitable temperature from a melting point to a boiling point of the solvent. The reduction of a double bond of a product from a Wittig reaction is carried out by contact reduction, catalytic hydrogen migration reaction, or hydrazine reduction using a palladium catalyst or a Wilkinson complex.

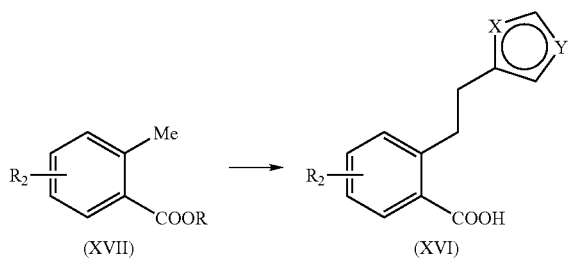

The compounds represented by the general formula (I) mentioned above embrace, in a case where a pharmaceutically acceptable salt thereof is present, various kinds of salts thereof, and include, for example, addition salts with an acid such as hydrochloric acid, oxalic acid, fumaric acid, p-toluenesulfonic acid, maleic acid, succinic acid, acetic acid, citric acid, tartaric acid, carbonic acid, or nitric acid. In addition, the salts of carboxyl group of the compounds include suitable alkali metal salt of sodium, potassium, calcium and the like. These salts can be produced from each compound in a free form, or converted reversibly, in accordance with a known method. In addition, in a case where the compounds are present in the state of a steric isomer such as a cis-trans isomer, an optical isomer or a coordination isomer, or a hydrate or a metal complex compound, the present invention embraces any of steric isomers, hydrates, and complex compounds.

The compound of the present invention can be combined with a suitable pharmaceutical carrier or diluent to form a medicament. Also, the compound can be produced into preparations by any ordinary methods, and the compounds can be produced into formulations as an orally administered agent such as a tablet, a capsule, a fine powder, or a liquid, or as a parenterally administered agent for subcutaneous administration, intramuscular administration, intrarectal administration, or intranasal administration. In the prescription, the compound of the present invention may be used in the form of a pharmaceutically acceptable salt thereof, and the compounds can be used alone or in a proper combination, and further, a blending agent with another pharmaceutically active ingredient.

The orally administered preparation can be used directly, or in a proper combination with a suitable additive, for example, a conventional excipient such as lactose, mannitol, corn starch, or potato starch, together with a binder such as a crystalline cellulose, a cellulose derivative, gum arabic, corn starch, or gelatin, a disintegrant such as corn starch, potato starch, carboxymethyl cellulose potassium, a lubricant such as talc or magnesium stearate, and other additive such as a filler, a wetting agent, a buffer, a preservative, or perfume, and the like to produce a tablet, a powder, a granule, or a capsule.

In addition, the compound can be produced into preparations in a dosage form other than above that is optimal for the treatment depending upon the kinds of the disease and the patients, including, for example, externally administered agents, such as injections, suppositories, inhalants, aerosols, syrups, instillations, and ointments, and the like.

The desired dose for the compound of the present invention may vary depending upon the subject to be administered, the dose form, the administration method, the administration time period, and the like. In order to obtain a desired effect, the compound of the present invention can be generally orally administered in an amount of from 0.5 to 1000 mg, and preferably from 1 to 500, for adult, at once or in several divided administrations per day. In the case of the parenteral administration (for example, an injection), the daily dose is preferably from one-third to one-tenth the dose level for each of the doses mentioned above.

EXAMPLES

Next, the present invention will be specifically described hereinbelow by the Examples, without intending to limit the scope of the present invention thereto.

A melting point was determined by placing a sample in a glass capillary tube, and using Yamato Scientific, Model MP-21, a melting point measuring instrument (No compensation of the thermometer was made). The MS spectrum was measured with POLARIS Q (Thermo Quest). $^1$H-NMR was measured with Bruker, Model ARX500, a nuclear magnetic resonance analyzer, in which chemical shift was expressed in ppm, using TMS added as an internal standard (b=0 ppm) as a standard. Silica gel column chromatography was performed using silica gel BW-127ZH for chromatography (FUJI SILYSIA CHEMICAL LTD.). Thin-layer chromatography was performed using silica gel F254 (Merck, No. 5715), in which detection was made using a UV lamp and a 5% phosphomolybdic acid-ethanol color development reagent.

Example 1

Production of 4-(2-Bromo-9,10-dihydro-1-thiabenzo[f]azulen-4-ylidene)-1-methylpiperidine [Compound 212]

Bromine (1.0 mL, 19.5 mmol) was added dropwise to a chloroform (50 mL) solution of 4-(9,10-dihydro-1-thiabenzo

[f]azulen-4-ylidene)-1-methylpiperidine (5.76 g, 19.5 mmol) at 0° C., and the mixture was stirred at room temperature for 2 hours. Thereafter, a saturated aqueous sodium bicarbonate solution was added to the mixture, and an organic layer was separated. The organic layer was washed with a saturated sodium chloride solution, and dried over anhydrous sodium sulfate. The solvents were distilled off under a reduced pressure, and the residue was purified by column chromatography (chloroform-methanol=9:1), to give 5.6 g (91%) of the captioned compound in the form of white crystals.

Mp. 141°-142° C. MS (EI): m/z 375 [M$^+$+2], 373 [M$^+$]. $^1$H-NMR (DMSO-d$_5$) δ: 1.90-2.79 (m, 13H), 3.18-3.22 (m, 2H), 6.85 (s, 1H), 6.98-7.30 (m, 4H).

Example 2

Production of 4-(2-Cyano-9,10-dihydro-1-thiabenzo [f]azulen-4-ylidene)-1-methylpiperidine hydrochloride [Compound 1]

Zn(CN)$_2$ (0.94 g, 8.8 mmol), Pd$_2$(dba)$_3$ (0.61 g, 0.74 mmol), and DPPF (0.89 g, 1.8 mmol) were added to a DMF (25 mL) solution of the compound obtained in Example 1 (5.0 g, 14.7 mmol) in an argon atmosphere, and the mixture was stirred overnight at 80° C. Insoluble matters were filtered off, a saturated sodium chloride solution (50 mL) was then added to the filtrate, and the product was extracted with ethyl acetate. The solvents were distilled off under a reduced pressure, the residue was then purified by silica gel column chromatography (chloroform-methanol=9:1), and the resulting oily product was treated with 4 mol/L hydrogen chloride-dioxane, to give 1.9 g (40%) of the captioned compound in the form of crystals.

Example 3

Production of 4-(1-Methylpiperidin-4-ylidene)-9,10-dihydro-4H-1-thiabenzo[f]azulene-2-carboxylic acid hydrochloride [Compound 4]

A 2 mol/L aqueous sodium hydroxide solution (20 mL) was added to an ethanol (10 mL) solution of Compound 1 (1.5 g, 4.2 mmol), and the mixture was stirred overnight while refluxing and heating. Ethanol was distilled off under a reduced pressure, and 6 mol/L hydrochloric acid was added to the resulting residue. The precipitated crystals were collected by filtration, and sufficiently washed with water. The crystals were dried over phosphorus pentoxide at 50° C. under a reduced pressure, to give 0.96 g (67%) of the captioned compound.

Example 4

Production of Ethyl 4-(1-methylpiperidin-4-ylidene)-9,10-dihydro-4H-1-thiabenzo[f]azulene-2-carboxylate [Compound 3]

Ethanol (10 mL) was chilled to 0° C., and thionyl chloride (0.24 mL, 0.32 mmol) was added dropwise. Compound 4 (100 mg, 0.29 mmol) was added to the solution, and the mixture was stirred for 30 minutes, and then refluxed while heating for 2 hours. After allowing the refluxed mixture to cool in the air, the solvents were distilled off under a reduced pressure, and the precipitated crystals were separated by filtration and dried, to give 107 mg (100%) of the captioned compound in the form of white crystals.

Example 5

Production of Ethyl[4-(1-ethoxycarbonylpiperidin-4-ylidene)-9,10-dihydro-4H-1-thiabenzo[f]azulen-2-yl]carboxylate [Compound 61]

Ethyl chlorocarbonate (57 mL, 599 mmol) was added to a dichloroethane (140 mL) solution of Compound 3 (22.0 g, 59.9 mmol), and the mixture was stirred overnight while refluxing and heating. The solvent was distilled off under a reduced pressure, and the resulting residue was purified by silica gel column chromatography (chloroform), to give 26.3 g (100%) of the captioned compound.

Example 6

Production of Ethyl[4-piperidin-4-ylidene)-9,10-dihydro-4H-1-thiabenzo[f]azulen-2-yl]carboxylate [Compound 62]

A 33% hydrogen bromide-acetic acid solution (23 mL, 133.2 mmol) was added to an acetic acid (90 mL) solution of Compound 61 (10.5 g, 24.7 mmol), and the mixture was refluxed with heating for 5 hours. After allowing the mixture to cool in the air, the solvents were distilled off under a reduced pressure, and the precipitated crystals were separated by filtration and dried to give 8.8 g (82%) of the captioned compound.

Example 7

Production of Ethyl {4-{1-[4-(4-t-butylphenyl)-4-oxobutyl]piperidin-4-ylidene}-9,10-dihydro-4H-1-thiabenzo[f]azulen-2-yl}carboxylate [Compound 109]

Triethylamine (2.1 mL, 15.1 mmol) and 1-(4-tert-butylphenyl)-4-chlorobutan-1-one (1.98 g, 8.3 mmol) were added to a DMF (75 mL) solution of Compound 62 (3.0 g, 6.9 mmol), and the mixture was stirred at 80° C. for 21 hours. The solvents were distilled off under a reduced pressure, water was then added to the residue, and the product was extracted with ethyl acetate. The organic layer was washed with a saturated sodium chloride solution, and then dried over anhydrous sodium sulfate. The solvents were distilled off under a reduced pressure, and the residue was then purified by silica gel column chromatography (hexane-ethyl acetate), to give 0.9 g (23%) of the captioned compound.

Example 8

Production of 2-Bromo-4-(1-methylpiperidin-4-ylidene)-9,10-dihydro-4H-3-thiabenzo[f]azulene hydrobromide [Compound 2]

Bromine (0.52 mL, 10.2 mmol) was added dropwise to a chloroform (30 mL) solution of 4-(1-methylpiperidin-4-ylidene)-9,10-dihydro-4H-3-thiabenzo[f]azulene (3.0 g, 10.2 mmol) at 0° C. The mixture was stirred at room temperature for 2 days, and a saturated aqueous sodium bicarbonate solution was then added thereto to allow separation of an organic layer. The organic layer was washed with a saturated sodium chloride solution, and then dried over anhydrous sodium sulfate. The solvents were distilled off under a reduced pressure, and the residue was then purified by column chromatography (chloroform-methanol=9:1), to give 3.8 g (100%) of the captioned compound in the form of white crystals.

Example 9

Production of Ethyl 3-[4-(1-methylpiperidin-4-ylidene)-9,10-dihydro-4H-3-thiabenzo[f]azulen-2-yl]acrylate [Compound 22]

Triethylamine (35.5 mL, 255 mmol), ethyl acrylate (26.8 mL, 246 mmol), palladium acetate (0.4 g, 1.8 mmol), and tri(o-toluoyl)phosphine (1.5 g, 5.0 mmol) were added to a DMF (160 mL) solution of Compound 2 (9.2 g, 24.5 mmol), and the mixture was stirred overnight at 80° C. in an argon atmosphere. A saturated aqueous ammonium chloride solution was added to the reaction mixture, the product was extracted with ethyl acetate, and the organic layer was then washed with a saturated sodium chloride solution and dried over anhydrous sodium sulfate. The solvents were distilled off under a reduced pressure, and the resulting residue was then purified by column chromatography (chloroform-methanol=9:1), to give 7.6 g (79%) of the captioned compound in the form of white crystals.

Example 10

Production of 4-(6-Bromo-10H-9-oxa-3-thiabenzo[f]azulen-4-ylidene)-1-methylpiperidine 6-Bromo-10H-9-oxa-3-thiabenzo[f]azulen-4-one (21.6 g, 100 mmol) was added to a Grignard reagent prepared from 4-chloro-N-methylpiperidine (20 mL, 150 mmol), a metal magnesium (3.6 g, 150 mmol), dibromoethane (0.1 mL), and THF (200 mL). The reaction mixture was stirred at room temperature for 2 hours, a saturated aqueous ammonium chloride solution was added to the solution to stop the reaction, and a product was then extracted with ethyl acetate. The organic layer was washed with a saturated sodium chloride solution, and dried over anhydrous sodium sulfate. The solvents were distilled off under a reduced pressure, the resulting residue was dissolved in dichloromethane (300 mL), trifluoroacetic acid (77 mL, 1.0 mol) was added thereto, and the mixture was stirred overnight. The solvents were distilled off under a reduced pressure, and a saturated aqueous sodium bicarbonate solution was added to the residue. The product was extracted with ethyl acetate, and the extract was washed with a saturated sodium chloride solution, and dried over anhydrous sodium sulfate. The solvents were distilled off under a reduced pressure, and the resulting residue was then purified by column chromatography (hexane-ethyl acetate=3:2), to give 16.2 g (81%) of the captioned compound.
MS (EI): m/z 378.0 [M$^+$+1]. $^1$H-NMR (DMSO-d$_6$) δ: 2.09-2.77 (m, 11H), 4.85 (d, J=15.5 Hz, 1H), 5.42 (d, J=15.5 Hz, 1H), 6.81-7.45 (m, 5H).

Example 11

Production of 2-[4-(1-Methylpiperidin-4-ylidene)-4,10-dihydro-9-oxa-3-thiabenzo[f]azulen-6-yl]propionic acid hydrochloride [Compound 57]

Hexamethyldisilazane (5.0 mL, 31.2 mmol) was ice-cooled in an argon atmosphere, and a 1.6 mol/L butyllithium-hexane solution (19.5 mL, 31.2 mmol) was added dropwise thereto. After stirring the mixture for 30 minutes, t-butyl propionate (2.1 g, 16.1 mmol) was added dropwise to the solution, and stirred for 30 minutes. Further, Pd(dba)$_2$ (0.45 g, 0.8 mmol) and N,N'-(2,6-diisopropylphenyl)dihydroimidazolium chloride (0.34 g, 0.8 mmol) were added thereto, the mixture was stirred for 10 minutes, and a toluene (25 mL) solution of 4-(6-bromo-10H-9-oxa-3-thiabenzo[f]azulen-4-ylidene)-1-methylpiperidine (3.0 g, 8.0 mmol) was then added dropwise thereto. The mixture was stirred overnight at room temperature, water was then added to the reaction mixture, and the product was extracted with ethyl acetate. The solvents in the organic layer were distilled off under a reduced pressure, and the residue was purified by silica gel column chromatography (hexane-ethyl acetate). The purified compound was dissolved in dioxane (10 mL), a 4 mol/L hydrogen chloride-dioxane solution (12.5 mL, 50 mmol) was added to the solution, and the mixture was stirred overnight. The solvents were distilled off under a reduced pressure, and the precipitated crystals were collected by filtration, to give 1.5 g (69%) of the captioned compound.

Example 12

Production of 2-Bromo-9,10-dihydro-1-thiabenzo[f]azulen-4-one

Bromine (8.5 mL, 165 mmol) was added dropwise to a chloroform (300 mL) solution of 9,10-dihydro-1-thiabenzo[f]azulen-4-one (23.2 g, 108 mmol), and the mixture was stirred for 4 hours. Water was added to the reaction mixture, the product was extracted with ethyl acetate, the organic layer was then washed with a saturated aqueous sodium bicarbonate solution and with a saturated sodium chloride solution, and dried over anhydrous sodium sulfate. The solvents were distilled off under a reduced pressure, and the residue was purified by silica gel chromatography (hexane-ethyl acetate), to give 22.0 g (69%) of the captioned compound.
MS (EI): m/z 294 [M$^+$+2], 292 [M]. $^1$H-NMR (DMSO-d$_6$) δ: 3.19 (s, 4H), 7.38-7.42 (m, 2H), 7.52-7.55 (m, 2H), 7.78-7.79 (m, 1H).

Example 13

Production of 2,9,10-Tribromo-9,10-dihydro-1-thiabenzo[f]azulen-4-one

NBS (65.4 g, 367 mmol) and benzoyl peroxide (0.1 g, 0.5 mmol) were added to a dichloroethane (500 mL) solution of the compound obtained in Example 12 (53.9 g, 184 mmol), and the mixture was refluxed while heating for 4 hours. The reaction mixture was allowed to cool in the air, and a saturated potassium carbonate was then added thereto to allow an organic layer to separate. The organic layer was further washed with a saturated potassium carbonate and with a saturated sodium chloride solution, and then dried over anhydrous sodium sulfate. The solvents were distilled off under a reduced pressure, and the residue was purified by silica gel column chromatography (hexane-ethyl acetate), to give 76.8 g (93%) of the captioned compound.
$^1$H-NMR (DMSO-d$_6$) δ: 5.96 (d, J=5.3 Hz, 1H), 6.22 (d, J=5.3 Hz, 1H), 7.67-7.74 (m, 4H), 8.03-8.05 (m, 1H).

Example 14

Production of 2-Bromo-10-methoxy-1-thiabenzo[f]azulen-4-one

A methanol (1100 mL) solution of the compound obtained in Example 13 (90.2 g, 200 mmol) was refluxed while heating overnight. After allowing the mixture to cool in the air, DBU (63.4 g, 417 mmol) was further added thereto, and the mixture was refluxed while heating for another overnight. The reaction mixture was allowed to cool in the air, and the precipitated crystals were separated by filtration and dried, to give the captioned compound in an amount of 55.7 g, 173 mmol (2 steps, 87%).

MS (EI): m/z 322 [$M^++2$], 320 [$M^+$]. $^1$H-NMR (DMSO-$d_6$) δ: 4.02 (s, 3H), 6.98 (s, 1H), 7.61-7.62 (m, 1H), 7.77-7.80 (m, 1H), 7.90-7.96 (m, 2H), 8.46-8.47 (m, 1H).

Example 15

Production of 2-Bromo-10-methoxy-4-(1-methylpiperidin-4-yl)-4H-1-thiazobenzo[f]azulen-4-ol The compound obtained in Example 14 (4.27 g, 13.3 mmol) was added to a Grignard reagent prepared from 4-chloro-N-methylpiperidine (2.7 mL, 20 mmol), a metal magnesium (0.49 g, 21 mmol), dibromoethane (0.2 mL), and THF (20 mL). The reaction mixture was stirred at room temperature for 2 hours, and a saturated aqueous ammonium chloride solution was added to the solution to stop the reaction, and a formed product was then extracted with ethyl acetate. The organic layer was washed with an aqueous sodium chloride solution, and dried over anhydrous sodium sulfate. The solvent was distilled off under a reduced pressure, and the resulting residue was purified by silica gel column chromatography (hexane-ethyl acetate), to give 2.8 g (50%) of the captioned compound.

MS (EI): m/z 422 [$M^++3$], 420 [$M^++1$]. $^1$H-NMR (DMSO-$d_6$) δ: 0.41-0.43 (m, 1H), 0.77-0.87 (m, 2H), 1.18-1.52 (m, 3H), 1.83-1.92 (m, 1H), 1.99 (s, 3H), 2.50-2.55 (m, 1H), 2.64-2.66 (m, 1H), 5.83 (s, 1H), 6.40 (s, 1H), 7.22-7.26 (m, 2H), 7.31-7.34 (m, 1H), 7.38-7.39 (m, 1H), 7.72-7.73 (m, 1H).

Example 16

Production of Ethyl[4-hydroxy-10-methoxy-4-(1-methylpiperidin-4-yl)-4H-1-thiabenzo[f]azulen-2-yl]acetate Hexamethyldisilazane (16.8 g, 104 mmol) was ice-cooled in an argon atmosphere, and a 1.6 mol/L butyllithium-hexane solution (65 mL, 104 mmol) was added dropwise thereto. After stirring the mixture for 30 minutes, ethyl acetate (5 mL, 51 mmol) was added dropwise to the solution, and the mixture was stirred 30 minutes. Further, Pd(dba)$_2$ (1.5 g, 2.6 mmol) and N,N'-(2,6-diisopropylphenyl)dihydroimidazolium chloride (1.1 g, 2.6 mmol) were added to the mixture, the mixture was stirred for 10 minutes, and a toluene (100 mL) solution of the compound obtained in Example 15 (5.0 g, 12 mmol) was then added dropwise thereto. After the mixture was stirred at room temperature overnight, water was added to the reaction mixture, and the product was extracted with ethyl acetate. The solvents in the organic layer were distilled off under a reduced pressure, and the residue was purified by silica gel column chromatography (hexane-ethyl acetate), to give 3.1 g (60%) of the captioned compound.

MS (EI): m/z 428 [$M^++1$]. $^1$H-NMR (DMSO-$d_6$) δ: 0.41-0.78 (m, 2H), 1.18 (t, J=7.1 Hz, 3H), 1.30-1.83 (m, 5H), 1.99 (s, 3H), 2.50-2.63 (m, 2H), 3.84-3.92 (m, 5H), 4.08 (q, J=7.1 Hz, 2H), 5.68 (s, 1H), 6.33 (s, 1H), 7.10 (s, 1H), 7.20-7.74 (m, 4H).

Example 17

Production of [4-(1-Methylpiperidin-4-ylidene)-10-oxo-9,10-dihydro-4H-1-thiabenzo[f]azulen-2-yl] acetic acid [Compound 87]

Hydrochloric acid (8 mL) was added to an ethanol (24 mL) solution of the compound obtained in Example 16 (2.0 g, 4.7 mmol), and the mixture was refluxed while heating overnight. The solvents were distilled off, water (20 mL) and sodium hydroxide (0.8 g, 20 mmol) were then added to the residue, and the mixture was stirred at room temperature overnight. The property of the solution is adjusted to a pH of 6.5 with hydrochloric acid, and the precipitated crystals were separated by filtration and dried, to give 0.68 g (39%) of the captioned compound.

Example 18

Production of Ethyl (4-Hydroxyphenylsulfanyl)acetate

Ethyl bromoacetate (21.5 mL, 194 mmol) and potassium carbonate (50.7 g, 367 mmol) were added to a DMF (450 mL) solution of 4-mercaptophenol (23.1 g, 183 mmol), and the mixture was stirred at room temperature overnight. The solvents were distilled off under a reduced pressure, water was added to the residue, and the product was extracted with ethyl acetate. The organic layer was washed with a saturated sodium chloride solution, and then dried over anhydrous sodium sulfate, and solvents were distilled off under a reduced pressure. The residue was purified by silica gel column chromatography (hexane:ethyl acetate=5:1), to give 30.3 g (78%) of the captioned compound.

MS (EI): m/z 212 [$M^+$]. $^1$H-NMR (DMSO-$d_6$) δ: 1.11 (t, J=7.1 Hz, 3H), 3.60 (s, 2H), 4.03 (q, J=7.1 Hz, 2H), 6.72-6.74 (m, 2H), 7.25-7.27 (m, 2H), 9.64 (s, 1H).

Example 19

Production of Methyl 3-(4-ethoxycarbonylmethylsulfanylphenoxymethyl)thiophene-2-carboxylate Methyl 3-bromomethylthiophene-2-carboxylate (28.2 ml, 120 mmol) and potassium carbonate (36.6 g, 264 mmol) were added to a DMF (300 mL) solution of the compound obtained in Example 18 (28.1 g, 132 mmol), and the mixture was stirred overnight at room temperature. The solvents were distilled off under a reduced pressure, water was added to the residue, and the product was extracted with ethyl acetate. The organic layer was washed with a saturated sodium chloride solution, and then dried over anhydrous sodium sulfate, and the solvents were distilled off under a reduced pressure. The residue was purified by silica gel column chromatography (hexane:ethyl acetate=5:1), to give 35.1 g (80%) of the captioned compound.

$^1$H-NMR (DMSO-$d_6$) δ: 1.11 (t, J=7.1 Hz, 3H), 3.70 (s, 2H), 3.83 (s, 3H), 4.04 (q, J=7.1 Hz, 2H), 5.41 (s, 2H), 6.96-7.38 (m, 5H), 7.89-7.90 (m, 1H).

Example 20

Production of 3-(4-Carboxymethylsulfanylphenoxymethyl)thiophene-2-carboxylic acid An aqueous sodium hydroxide (19.2 g, 480 mmol) solution was added to a methanol (250 mL) solution of the compound obtained in Example 19 (35.1 g, 96 mmol), and the mixture was refluxed while heating for 2 hours. After allowing the mixture to cool in the air, the solvents were distilled off under a reduced pressure, and water was added to the residue. The solution was neutralized with hydrochloric acid, and the precipitated crystals were separated by filtration and dried, to give 30.0 g (97%) of the captioned compound.

$^1$H-NMR (DMSO-d$_6$) δ: 3.64 (s, 2H), 5.41 (s, 2H), 6.94-7.36 (m, 5H), 7.79-7.80 (m, 1H), 13.04 (brs, 2H).

Example 21

Production of (4-oxo-4,10-dihydro-9-oxa-3-thiabenzo[f]azulen-6-ylsulfanyl)acetic acid Trifluoroacetic acid anhydride (28.0 mL, 201 mmol) was added to a dichloroethane (300 mL) solution of the compound obtained in Example 20 (29.0 g, 89 mmol), and the mixture was stirred overnight at 60° C. The solvents were distilled off under a reduced pressure, and water was added to the residue. The precipitated crystals were separated by filtration and dried, to give 26.7 g (98%) of the captioned compound.

MS (EI): m/z 307 [M$^+$+1]. $^1$H-NMR (DMSO-d$_6$) δ: 3.81 (s, 2H), 5.31 (s, 2H), 7.20-8.10 (m, 5H), 12.78 (brs, 1H).

Example 22

Production of Methyl (4-oxo-4,10-dihydro-9-oxa-3-thiabenzo[f]azulen-6-ylsulfanyl)acetate Methyl iodide (6.5 mL, 104 mmol) and potassium hydrogencarbonate (17.0 g, 170 mmol) were added to a DMF (200 mL) solution of the compound obtained in Example 21 (26.1 g, 85 mmol), and the mixture was stirred at room temperature overnight. The solvents were distilled off under a reduced pressure, water was added to the residue, and the product was extracted with ethyl acetate. The organic layer was washed with a saturated sodium chloride solution and then dried over anhydrous sodium sulfate, and the solvents were distilled off under a reduced pressure. The residue was purified by silica gel column chromatography (hexane:ethyl acetate=5:1), to give 24.0 g (88%) of the captioned compound.

MS (EI): m/z 320 [M$^+$]. $^1$H-NMR (DMSO-d$_6$) δ: 3.64 (s, 3H), 3.91 (s, 2H), 5.31 (s, 2H), 7.20-7.27 (m, 2H), 7.63-7.66 (m, 1H), 7.97-8.10 (m, 2H).

Example 23

Production of Methyl[4-hydroxy-4-(1-methylpiperidin-4-yl)-4,10-dihydro-9-oxa-3-thiabenzo[f]azulen-6-ylsulfanyl]acetate A Grignard reagent prepared from magnesium (2.8 g, 116 mmol), 4-chloro-1-methylpiperidine (15.5 mL, 116 mmol), and THF (180 mL) was ice-cooled, and a THF (120 mL) solution of the compound obtained in Example 22 (18.5 g, 58 mmol) was added dropwise thereto. After allowing the mixture to react for 30 minutes, a saturated ammonium chloride was added thereto, and a product was extracted with ethyl acetate. The organic layer was sequentially washed with a saturated ammonium chloride and with a saturated sodium chloride solution, and then dried over anhydrous sodium sulfate, and the solvents were distilled off under a reduced pressure. The residue was purified by silica gel column chromatography (hexane:ethyl acetate=3:2), to give 4.4 g (18%) of the captioned compound.

$^1$H-NMR (DMSO-d$_6$) δ: 0.78-0.80 (m, 1H), 1.34-1.64 (m, 5H), 2.05 (s, 3H), 2.26-2.29 (m, 1H), 2.63-2.75 (m, 2H), 3.61 (s, 3H), 3.80-3.87 (m, 2H), 4.74 (d, =15.5 Hz, 1H), 5.38 (d, =15.5 Hz, 1H), 6.06 (s, 1H), 6.70-6.71 (m, 1H), 7.09-7.48 (m, 4H).

Example 24

Production of Methyl[4-(1-methylpiperidin-4-yl)-4,10-dihydro-9-oxa-3-thiabenzo[f]azulen-6-ylsulfanyl]acetate Trifluoroacetic acid (10 mL) was added to a dichloromethane solution of the compound obtained in Example 23 (5.7 g, 14 mmol), and the mixture was stirred at room temperature overnight. The solvents were distilled off, and the residue was purified by silica gel column chromatography (hexane:ethyl acetate=3:2), to give a free compound. Thereafter, 4 mol/L hydrogen chloride-dioxane (8.0 mL, 32 mmol) was added thereto, and the mixture was stirred for 1 hour. The solvents were distilled off under a reduced pressure, and ether was added to the residue to allow crystallization. The precipitated crystals were separated by filtration and dried, to give 4.1 g (69%) of the captioned compound.

Mp. 210°-212° C. $^1$H-NMR (DMSO-d$_6$) δ: 2.36-3.60 (m, 11H), 3.60 (s, 3H), 3.81-3.93 (m, 2H), 4.87 (d, J=15.3 Hz, 1H), 5.45 (d, J=15.3 Hz, 1H), 6.85-7.53 (m, 5H), 10.67 (brs, 1H).

Example 25

Production of [4-(1-Methylpiperidin-4-ylidene)-4,10-dihydro-9-oxa-3-thiabenzo[f]azulen-6-ylsulfanyl] acetic acid [Compound 172]

An aqueous sodium hydroxide (1.4 g, 680 mmol) solution was added to an ethanol (40 mL) solution of the compound obtained in Example 24 (2.9 g, 6.7 mmol), and the mixture was refluxed while heating for 2 hours. After allowing the mixture to cool in the air, the solvents were distilled off under a reduced pressure, water was added to the residue, and the mixture was neutralized with hydrochloric acid. The precipitated crystals were separated by filtration and dried, to give 1.3 g (50%) of the captioned compound.

Example 26

Production of 1-Cyclohexyloxycarbonyloxyethyl 4-(1-methylpiperidin-4-ylidene)-9,10-dihydro-4H-1-thiabenzo[f]azulene-2-carboxylate hydrochloride [Compound 176]

Triethylamine (6.2 mL, 44.2 mmol), potassium iodide (4.4 g, 26.5 mmol), and 1-chloroethyl cyclohexyl carbonate (2.2 g, 10.6 mmol) were added to a DMF (50 mL) solution of the compound 4 (3.0 g, 8.84 mmol), and the mixture was stirred at 80° C. overnight. The solvents were distilled off under a reduced pressure, water was added to the residue, and the product was extracted with ethyl acetate. The organic layer was washed with a saturated sodium chloride solution and then dried over anhydrous sodium sulfate, and the solvents were distilled off under a reduce pressure. The residue was purified by silica gel column chromatography (hexane:ethyl acetate=5:1). The resulting free amino acids were dissolved in dioxane (20 mL), 4 mol/L hydrogen chloride-dioxane was added thereto, and the mixture was stirred for 1 hour. The solvents were distilled off under a reduced pressure, and ether was added thereto to allow crystallization of a hydrochloride. The crystals were separated by filtration and dried, to give 1.8 g (2 steps, 37%) of the captioned compound.

Example 27

Production of 4-(2-Bromo-10H-9-oxa-3-thiabenzo[f]azulen-4-ylidene)-1-methyl-piperidine Bromine (5 mL, 98 mmol) was added dropwise to a chloroform (300 mL) solution of 1-methyl-4-(10H-9-oxa-3-thiabenzo[f]azulen-4-ylidene)piperidine (19.3 g, 65.0 mmol) at 0° C. The mixture was stirred at 0° C. for 2 hours, and a saturated aqueous sodium hydrogencarbonate solution was then added thereto to allow the separation of an organic layer. The organic layer was washed with a saturated sodium chloride solution and dried over anhydrous sodium sulfate, the solvents were then distilled off under a reduced pressure, and the residue was purified by column chromatography (chloroform:methanol=9:1). The crystals were formed from a petroleum ether, to give 11.2 g (46%) of the captioned compound.
Mp. 101°-103° C. $^1$H-NMR (CDCl$_3$) 2.10-2.71 (m, 11H), 4.76 (d, J=15.4 Hz, 1H), 5.36 (d, J=15.4 Hz, 1H), 6.93 (s, 1H), 7.08-7.12 (m, 3H), 7.26-7.29 (m, 1H).

Example 28

Production of t-Butyl [4-(1-methylpiperidin-4-ylidene)-4,10-dihydro-9-oxa-3-thiabenzo[f]azulen-2-yl]acetate Hexamethyldisilazane (11.97 g, 74.2 mmol) was ice-cooled in an argon atmosphere, and a 1.6 mol/L n-butyllithium-hexane solution (46.6 mL, 74.6 mmol) was added dropwise thereto. t-Butyl acetate (4.9 mL, 36.7 mmol) was added dropwise to the solution, and the mixture was stirred for 30 minutes. Pd(dba)$_2$ (1.05 g, 1.8 mmol), N,N'-(2,6-diisopropylphenyl)dihydroimidazolium chloride (0.80 g, 1.9 mmol), and the compound obtained in Example 27 (7.0 g, 18.6 mmol) were added thereto, and the mixture was heated to room temperature, and stirred overnight. Water was added to the reaction mixture, and the product was extracted with ethyl acetate and dried over anhydrous sodium sulfate. The organic layer was distilled off under a reduced pressure, and the residue was purified by column chromatography (hexane:ethyl acetate=9:1), to give 3.30 g (43%) of the captioned compound in the form of an oily product.
MS (EI): m/z 412 [M$^+$+1]. $^1$H-NMR (DMSO-d$_6$) δ: 1.40 (s, 9H), 2.11-2.28 (m, 6H), 2.39-2.57 (m, 3H), 2.68-2.74 (m, 2H), 3.70 (s, 2H), 4.76 (d, J=15.4 Hz, 1H), 5.36 (d, J=15.4 Hz, 1H), 6.58 (s, 1H), 7.05-7.10 (m, 3H), 7.25 (dd, J=2.3, 8.5 Hz, 1H).

Example 29

Production of [4-(1-Methylpiperidin-4-ylidene)-4,10-dihydro-9-oxa-3-thiabenzo[f]azulen-2-yl]acetic acid hydrochloride [Compound 58]

A 4 mol/L hydrogen chloride-dioxane solution (10 mL, equivalent to 40 mmol hydrogen chloride) was added to a dioxane (30 mL) solution of the compound obtained in Example 28 (2.21 g, 5.4 mmol), and the mixture was stirred at 40° C. for 8 hours. The solvents were distilled off under a reduced pressure, and the precipitated crystals were collected by filtration, to give 1.70 g (81%) of the caption compound in the form of crystals containing 0.5 equivalents of dioxane.

Example 30

Production of Methyl {4-[1-(4-oxopentyl)piperidin-4-ylidene]-4,10-dihydro-9-oxa-3-thiabenzo[f]azulen-6-yl}acetate 5-Chloro-2-pentanone (2.4 mL, 20.9 mmol) was added to a DMF (50 mL) solution of methyl (4-piperidin-4-ylidene-4,10-dihydro-9-oxa-3-thiabenzo[f]azulen-6-yl)acetate (2.50 g, 7.0 mmol), anhydrous potassium carbonate (2.15 g, 15.6 mmol), and potassium iodide (1.41 g, 8.5 mmol), and the mixture was stirred overnight at 80° C. The solvents were distilled off under a reduced pressure, water was added to the residue, and the product was extracted with ethyl acetate. The organic layer was dried over anhydrous sodium sulfate, and the solvents were then distilled off under a reduced pressure. The residue was purified by column chromatography (chloroform:methanol=19:1), to give 2.40 g (78%) of the captioned compound in the form of an oily product.
MS (EI): m/z 439 [M$^+$]. $^1$H-NMR (DMSO-d$_6$) δ: 1.63 (tt, J=7.1, 7.1 Hz, 2H), 2.09 (s, 3H), 2.17-2.33 (m, 5H), 2.36-2.47 (m, 3H), 2.49-2.61 (m, 2H), 2.65-2.72 (m, 2H), 3.59 (s, 3H), 3.61 and 3.65 (ABq, J=15.7 Hz, 2H), 4.82 (d, J=15.3 Hz, 1H), 5.40 (d, J=15.3 Hz, 1H), 6.79 (d, J=5.2 Hz, 1H), 7.00 (d, J=2.0 Hz, 1H), 7.03 (d, J=8.2 Hz, 1H), 7.13 (dd, J=2.0, 8.2 Hz, 1H), 7.42 (d, J=5.2 Hz, 1H).

Example 31

Production of {4-[1-(4-Oxopentyl)piperidin-4-ylidene]-4,10-dihydro-9-oxa-3-thiabenzo[f]azulen-6-yl}acetic acid [Compound 170]

A 2 mol/L aqueous sodium hydroxide solution (5 mL, equivalent to 10 mmol sodium hydroxide) was added to an ethanol (20 mL) solution of the compound obtained in Example 30 (2.40 g, 5.5 mmol), and the mixture was stirred at room temperature for 2 hours. The solvents were distilled off, water was then added to the residue, and the aqueous solution was adjusted to a pH of 7 with a diluted hydrochloric acid. The precipitated crystals were separated by filtration and dried, to give 1.30 g (56%) of the captioned compound.

Example 32

Production of 2-Methyl-2-[4-(1-methylpiperidin-4-ylidene)-4,10-dihydro-9-oxa-3-thiabenzo[f]azulen-6-ylsulfanyl]propionic acid hydrochloride [Compound 190]

An aqueous solution (10 mL) of sodium hydroxide (0.82 g, 20.6 mol) was added to an ethanol (20 mL) solution of methyl 2-methyl-2-[4-(1-methylpiperidin-4-ylidene)-4,10-dihydro-9-oxa-3-thiabenzo[f]azulen-6-ylsulfanyl]propionate hydrochloride [Compound 189] (0.88 g, 1.8 mmol), and the mixture was refluxed while heating for 6 hours. The solvents were distilled off under a reduced pressure, the residue was then dissolved in water, the solution was neutralized with a diluted hydrochloric acid, and the precipitated crystals were separated by filtration and dried, to give 0.67 g (72%) of the captioned compound in the form of crystals.

Example 33

Production of Ethyl 4-(2-bromo-9,10-dihydro-1-thiabenzo[f]azulen-4-ylidene)piperidine-1-carboxylate Ethyl chlorocarbonate (32 mL, 336 mmol) was added to a toluene (200 mL) solution of the compound obtained in Example 1 (21.0 g, 56 mmol), and the mixture was refluxed while heating for 6 hours. The mixture was allowed to cool in the air, and the reaction mixture was added to a saturated aqueous sodium hydrogencarbonate solution to allow the separation of an organic layer. The organic layer was washed with a saturated sodium chloride solution and dried over anhydrous sodium sulfate, the solvents were then distilled off under a reduced pressure, and the residue was purified by column chromatography (hexane:ethyl acetate=19:1), to give 15.0 g (62%) of the captioned compound in the form of an oily product.

MS (EI): m/z 433 [M$^+$+2], 431 [M$^+$]. $^1$H-NMR (DMSO-d$_6$) δ: 1.17 (t, J=7.1 Hz, 3H), 2.10-2.23 (m, 2H), 2.38-2.48 (m, 2H), 2.68-2.83 (m, 2H), 2.92-3.26 (m, 4H), 3.52-3.78 (m, 2H), 4.04 (q, J=7.1 Hz, 2H), 6.90 (s, 1H), 7.02-7.13 (m, 1H), 7.16-7.36 (m, 3H).

Example 34

Production of Ethyl 442-(2-ethoxycarbonylvinyl)-9,10-dihydro-1-thiabenzo[f]azulen-4-ylidene)piperidine-1-carboxylate Ethyl acrylate (18.5 mL, 170 mmol), triethylamine (24 mL, 170 mmol), palladium acetate (0.3 g, 1.3 mmol), and tri(o-toluyl) phosphine (2.0 g, 6.6 mmol) were added to a DMF (50 mL) solution of the compound obtained in Example 33 (8.80 g, 17.0 mmol) in an argon gas stream, and the mixture was stirred overnight at 80° C. The mixture was allowed to cool in the air, water was then added to the reaction mixture, the product was extracted with ethyl acetate, and the organic layer was washed with a saturated sodium chloride solution and then dried over anhydrous sodium sulfate. The solvents were distilled off under a reduced pressure, and the residue was purified by column chromatography (hexane-ethyl acetate=9:1), to give 6.1 g (79%) of the captioned compound in the form of an oily product.

$^1$H-NMR (DMSO-d$_6$) δ: 1.18 (t, J=7.0 Hz, 3H), 1.23 (t, J=7.0 Hz, 3H), 2.11-2.16 (m, 1H), 2.20-2.28 (m, 1H), 2.38-2.48 (m, 2H), 2.78-2.86 (m, 2H), 2.96-3.14 (m, 1H), 3.20-3.32 (m, 3H), 3.55-3.61 (m, 1H), 3.68-3.74 (m, 1H), 4.04 (q, J=7.0 Hz, 2H), 4.15 (m, 2H), 6.06 (d, J=15.7 Hz, 1H), 7.03 (d, J=7.2 Hz, 1H), 7.16-7.24 (m, 2H), 7.27 (s, 1H), 7.31 (d, J=8.0 Hz, 1H), 7.72 (d, J=15.7 Hz, 1H).

Example 35

Production of t-Butyl 4-[2-(2-ethoxycarbonylethyl)-1-thiabenzo[f]azulen-4-ylidene]piperidine-1-carboxylate A 30% hydrogen bromide-acetic acid solution (3.8 mL, equivalent to 67.5 mmol of hydrogen bromide) was added to an acetic acid (50 mL) solution of the compound obtained in Example 34 (6.10 g, 13.5 mmol), and the mixture was stirred at 120° C. for 4 hours. The reaction mixture was allowed to cool in the air to room temperature, the residue obtained by distilling the mixture off the solvents under a reduced pressure was dissolved in ethanol (50 mL), a 2 mol/L aqueous sodium hydroxide solution (14 mL, equivalent to 28 mmol sodium hydroxide) was added to the solution, and the mixture was stirred at room temperature for 3 hours. The solvents were distilled off, water was then added to the residue, the aqueous solution was adjusted to a pH of 7 with a diluted hydrochloric acid, and the product was extracted with chloroform. The organic layer was washed with a saturated sodium chloride solution, the solvents were distilled off under a reduced pressure, di-t-butyl dicarbonate (3.0 g, 13.7 mmol) was then added to a dichloromethane (50 mL) solution of the residue, and the mixture was stirred at room temperature for 3 hours. Water was added to the mixture, the organic layer was allowed to separate out and dried with anhydrous sodium sulfate, and the solvents were then distilled off under a reduced pressure. Potassium hydrogencarbonate (4.0 g, 40.5 mmol) and ethyl iodide (1.1 mL, 13.5 mmol) were added to a DMF (50 mL) solution of the residue, and the mixture was stirred overnight at room temperature. Water was added to the reaction mixture, the product was extracted with ethyl acetate, the organic layer was washed with a saturated sodium chloride solution and then dried over anhydrous sodium sulfate, and the solvents were distilled off under a reduced pressure. The residue was purified by column chromatography (hexane:ethyl acetate=19:1), to give 2.9 g (45%) of the captioned compound in the form of an oily product.

$^1$H-NMR (CDCl$_3$) δ: 1.24 (t, J=7.1 Hz, 3H), 1.45 (s, 9H), 2.08-2.14 (m, 1H), 2.20-28 (m, 1H), 2.30-2.36 (m, 2H), 2.65 (t, J=7.6 Hz, 2H), 2.84-3.01 (m, 1H), 3.02 (m, 1H), 3.12 (t, J=7.6 Hz, 1H), 3.56-3.70 (m, 2H), 4.14 (q, J=7.1 Hz, 1H), 6.59 (s, 1H), 6.76 (d, J=11.5 Hz, 1H), 6.84 (d, J=11.5 Hz, 1H), 7.10 (d, J=7.6 Hz, 1H), 7.23-7.28 (m, 1H), 7.31-7.36 (m, 2H).

Example 36

Production of Ethyl 3-(4-piperidin-4-ylidene-4H-1-thiabenzo[f]azulen-2-yl)propionate Hydrogen chloride-dioxane (7.5 mL, equivalent to 30 mmol of hydrogen chloride) was added to a dioxane (30 mL) solution of the compound obtained in Example 35 (2.9 g, 6.0 mmol), and the mixture was stirred at room temperature for 5 hours. The solvents were distilled off under a reduced pressure, and the residue was purified by column chromatography (chloroform-methanol=19:1), to give 2.0 g (88%) of the captioned compound in the form of an oily product.

$^1$H-NMR (DMSO-d$_6$) δ: 1.15 (t, J=7.1 Hz, 3H), 1.82-1.89 (m, 1H), 2.03-2.10 (m, 1H), 2.11-2.18 (m, 1H), 2.26-2.32 (m, 1H), 2.44-2.58 (m, 1H), 2.60-2.68 (m, 2H), 2.70-2.82 (m, 1H), 3.02 (t, J=7.3 Hz, 2H), 3.44-3.52 (m, 1H), 3.65-3.74 (m, 1H), 4.04 (q, J=7.1 Hz, 2H), 6.67 (s, 1H), 6.85 (d, J=11.5 Hz, 1H), 6.89 (d, J=11.5 Hz, 1H), 7.09 (d, J=7.5 Hz, 1H), 7.25-7.30 (m, 1H), 7.34-7.38 (m, 2H).

Example 37

Production of 3-(4-Piperidin-4-ylidene-4H-1-thiabenzo[f]azulen-2-yl)propionic acid [Compound 209]

A 2 mol/L aqueous sodium hydroxide solution (10 mL, equivalent to 20 mmol of sodium hydroxide) was added to an ethanol (30 mL) solution of the compound obtained in Example 36 (2.0 g, 5.3 mmol), and the mixture was stirred at room temperature for 2 hours. The solvents were distilled off, water was then added to the residue, and the mixture was adjusted to a pH of 7 with a diluted hydrochloric acid. The precipitated crystals were separated by filtration and dried, to give 1.1 g (59%) of the captioned compound.

Compounds of the present invention other than those mentioned above were produced in the same manner in accordance with the general production methods mentioned above and the methods described in Examples, using an appropriate starting raw material in place of the starting raw material in Examples. The data of the properties for the compounds of the present invention thus obtained are shown in Tables 1 through 17.

TABLE 1

| Compound No. | Properties |
|---|---|
| Compound 1 | Mp. 138° C. (dec.). MS (EI): m/z 321 [M$^+$]. $^1$H-NMR (DMSO-d$_6$) δ: 1.92-2.85 (m, 13H), 3.18-3.21 (m, 1H), 3.35-3.37 (m, 1H), 7.02-7.58 (m, 5H). |
| Compound 2 | Mp. 164°-168° C. MS (EI): m/z 375 [M$^+$ + 2], 373 [M$^+$]. $^1$H-NMR (DMSO-d$_6$) δ: 1.99-3.17 (m, 15H), 6.85 (s, 1H), 7.00-7.31 (m, 4H). |
| Compound 3 | Mp. 135°-137° C. $^1$H-NMR (DMSO-d$_6$) δ: 1.24-1.27 (m, 3H), 1.91-2.85 (m, 13H), 3.23-3.38 (m, 2H), 4.20-4.28 (m, 2H), 7.03-7.41 (m, 5H). |
| Compound 4 | Mp. 212° C. (dec.). MS (EI): m/z 340 [M$^+$]. $^1$H-NMR (DMSO-d$_6$) δ: 2.21-2.85 (m, 12H), 3.17-3.39 (m, 3H), 7.03-7.31 (m, 5H). |
| Compound 5 | Mp. 243° C. (dec.). MS (EI): m/z 339 [M$^+$]. $^1$H-NMR (DMSO-d$_6$) δ: 2.61-3.40 (m, 15H), 7.09-7.40 (m, 5H), 10.42-10.98 (br, 1H), 12.78-13.08 (br, 1H). |
| Compound 6 | Mp. 229° C. (dec.). $^1$H-NMR (DMSO-d$_6$) δ: 1.22 (t, J = 7.1 Hz, 3H), 1.99-3.19 (m, 15H), 4.14 (q, J = 7.1 Hz, 2H), 6.01 (d, J = 16.1 Hz, 1H), 7.01-7.31 (m, 5H), 7.63 (d, J = 16.1 Hz, 1H). |
| Compound 7 | Mp. 252° C. (dec.). $^1$H-NMR (DMSO-d$_6$) δ: 2.38-2.85 (m, 13H), 3.20-3.45 (m, 2H), 6.01 (d, J = 15.7 Hz, 1H), 7.04-7.34 (m, 5H), 7.65 (d, J = 15.7 Hz, 1H), 11.00 (brs, 1H), 12.33 (brs, 1H). |
| Compound 8 | Mp. 153° C. (dec.). MS (EI): m/z 373 [M$^+$ + 1]. $^1$H-NMR (DMSO-d$_6$) δ: 1.89-2.55 (m, 11H), 6.87 (d, J = 11.6 Hz, 1H), 6.98 (d, J = 11.6 Hz, 1H), 7.06 (s, 1H), 7.12-7.13 (m, 1H), 7.30-7.33 (m, 1H), 7.41-7.44 (m, 2H). |
| Compound 9 | Mp. 190°-193° C. MS (EI): m/z 320 [M$^+$]. $^1$H-NMR (DMSO-d$_6$) δ: 2.00-2.89 (m, 13H), 3.16-3.19 (m, 2H), 7.04-7.33 (m, 4H), 7.61 (s, 1H). |
| Compound 10 | Mp. 230° C. (dec.). MS (EI): m/z 410 [M$^+$]. $^1$H-NMR (DMSO-d$_6$) δ: 1.44 (s, 9H), 2.01-3.17 (m, 15H), 6.10 (s, 1H), 6.96-7.26 (m, 4H), 10.20-10.23 (m, 1H). |
| Compound 11 | Mp. 223° C. (dec.). $^1$H-NMR (DMSO-d$_6$) δ: 2.00-3.17 (m, 18H), 6.21 (s, 1H), 6.97-7.27 (m, 4H), 10.94 (s, 1H). |
| Compound 12 | Mp. 239° C. (dec.). MS (EI): m/z 324 [M$^+$]. $^1$H-NMR (DMSO-d$_6$) δ: 2.33-3.61 (m, 15H), 4.01-4.21 (m, 2H), 6.89 (s, 1H), 7.05-7.33 (m, 4H), 8.29-8.34 (m, 3H), 11.01-11.12 (m, 1H). |
| Compound 13 | Mp. 185° C. (dec.). MS (EI): m/z 366 [M$^+$]. $^1$H-NMR (DMSO-d$_6$) δ: 2.04-3.28 (m, 18H), 4.40-4.53 (m, 2H), 5.74 (brs, 1H), 6.60 (s, 1H), 7.01-7.26 (m, 4H). |
| Compound 14 | Mp. 156° C. (dec.). MS (EI): m/z 353 [M$^+$]. $^1$H-NMR (DMSO-d$_6$) δ: 1.98-3.18 (m, 15H), 5.94-6.00 (m, 3H), 6.95-7.26 (m, 4H), 9.30 (brs, 1H). |

TABLE 2

| Compound No. | Properties |
|---|---|
| Compound 15 | Mp. 225° C. (dec.). $^1$H-NMR (DMSO-d$_6$) δ: 2.08-3.37 (m, 15H), 6.00 (d, J = 16.1 Hz, 1H), 6.95-7.31 (m, 5H), 7.58 (d, J = 16.1 Hz, 1H), 11.85-12.47 (br, 1H). |
| Compound 16 | Mp. 215° C. (dec.). $^1$H-NMR (DMSO-d$_6$) δ: 1.43 (s, 9H), 1.95-3.20 (m, 15H), 6.20 (s, 1H), 6.97-7.27 (m, 4H), 10.13 (brs, 1H). |
| Compound 17 | Mp. 225° C. (dec.). $^1$H-NMR (DMSO-d$_6$) δ: 1.98-2.80 (m, 16H), 3.12-3.21 (m, 2H), 6.29 (s, 1H), 6.98-7.28 (m, 4H), 10.89 (s, 1H). |
| Compound 18 | Mp. 115° C. (dec.). MS (EI): m/z 353 [M$^+$]. $^1$H-NMR (DMSO-d$_6$) δ: 1.93-3.21 (m, 15H), 5.96 (brs, 2H), 6.06 (s, 1H), 6.96-7.27 (m, 4H), 9.45 (brs, 1H). |
| Compound 19 | Mp. 230° C. (dec.). $^1$H-NMR (DMSO-d$_6$) δ: 2.27-3.38 (m, 15H), 4.09-4.10 (m, 2H), 6.97-7.33 (m, 5H), 8.40-8.51 (m, 3H), 10.92-11.12 (m, 1H). |
| Compound 20 | Mp. 118° C. (dec.) $^1$H-NMR (DMSO-d$_6$) δ: 1.79-2.80 (m, 16H), 3.18-3.22 (m, 2H), 4.22-4.30 (m, 2H), 6.60 (s, 1H), 6.97-7.28 (m, 4H), 8.32-8.33 (m, 1H). |
| Compound 21 | Mp. 134°-136° C. $^1$H-NMR (DMSO-d$_6$) δ: 1.25 (t, J = 7.1 Hz, 3H), 2.01-2.79 (m, 13H), 3.15-3.18 (m, 2H), 4.23 (q, J = 7.1 Hz, 2H), 7.02-7.32 (m, 4H), 7.44 (s, 1H). |
| Compound 22 | Mp. 93°-96° C. MS (EI): m/z 393[M$^+$]. $^1$H-NMR (DMSO-d$_6$) δ: 1.22 (t, J = 7.1 Hz, 3H), 1.99-3.19 (m, 15H), 4.14 (q, J = 7.1 Hz, 2H), 6.09 (d, J = 16.1 Hz, 1H), 7.01-7.31 (m, 5H), 7.63 (d, J = 16.1 Hz, 1H). |
| Compound 23 | Mp. 138° C. (dec.). MS (EI): m/z 380 [M$^+$]. $^1$H-NMR (DMSO-d$_6$) δ: 1.17 (t, J = 7.1 Hz, 3H), 2.00-2.75 (m, 13H), 3.04-3.18 (m, 2H), 3.75 (s, 2H), 4.06 (q, J = 7.1 Hz, 2H), 6.56 (s, 1H), 6.98-7.29 (m, 4H). |

TABLE 2-continued

| Compound No. | Properties |
|---|---|
| Compound 24 | Mp. 174° C. (dec.). $^1$H-NMR (DMSO-$d_6$) δ: 2.08-2.79 (m, 13H), 3.04-3.17 (m, 2H), 3.62 (s, 2H), 6.52 (s, 1H), 6.98-7.29 (m, 4H). |
| Compound 25 | Mp. 154°-156° C. MS (EI): m/z 323 [M$^+$ + 1]. $^1$H-NMR (DMSO-$d_6$) δ: 2.06-2.73 (m, 11H), 4.99 (d, J = 15.5 Hz, 1H), 5.49 (d, J = 15.5 Hz, 1H), 6.94-7.70 (m, 5H). |
| Compound 26 | Mp. 208° C. (dec.). MS (EI): m/z 342 [M$^+$ + 1]. $^1$H-NMR (DMSO-$d_6$) δ: 1.32-2.37 (m, 11H), 4.36 (d, J = 15.5 Hz, 1H), 5.97 (d, J = 15.5 Hz, 1H), 6.14-6.16 (m, 1H), 6.66-6.69 (m, 2H), 7.39-7.50 (m, 2H). |
| Compound 27 | Mp. 111° C. (dec.). MS (EI): m/z 382 [M$^+$]. $^1$H-NMR (DMSO-$d_6$) δ: 1.97-2.83 (m, 13H), 3.19-3.48 (m, 6H), 4.69-4.71 (m, 1H), 6.98-6.99 (m, 1H), 7.16-7.21 (m, 2H), 7.29-7.30 (m, 1H), 7.47 (s, 1H), 8.36-8.39 (m, 1H). |
| Compound 28 | Mp. 120° C. (dec.). MS (EI): m/z 426 [M$^+$]. $^1$H-NMR (DMSO-$d_6$) δ: 1.97-3.58 (m, 23H), 4.79-4.92 (br, 2H), 7.02-7.03 (m, 1H), 7.16-7.21 (m, 2H), 7.24 (s, 1H), 7.29-7.31 (m, 1H). |

TABLE 3

| Compound No. | Properties |
|---|---|
| Compound 29 | Mp. 111° C. (dec). MS (EI): m/z 426 [M$^+$]. $^1$H-NMR (DMSO-$d_6$) δ: 1.82-2.85 (m, 18H), 3.25-3.44 (m, 4H), 4.20-4.26 (m, 2H), 4.44-4.46 (m, 1H), 7.03-7.04 (m, 1H), 7.16-7.22 (m, 2H), 7.30-7.31 (m, 1H), 7.43 (s, 1H). |
| Compound 30 | Mp. 106° C. (dec.). MS (EI): m/z 396 [M$^+$]. $^1$H-NMR (DMSO-$d_6$) δ: 1.62-1.64 (m, 2H), 1.96-2.83 (m, 13H), 3.19-3.45 (m, 6H), 4.43-4.45 (m, 1H), 6.99-7.00 (m, 1H), 7.16-7.21 (m, 2H), 7.29-7.30 (m, 1H), 7.44 (s, 1H), 8.33-8.35 (m, 1H). |
| Compound 31 | Mp. 220° C. (dec.). $^1$H-NMR (DMSO-$d_6$) δ: 1.97-2.83 (m, 13H), 3.22-3.29 (m, 2H), 6.99-7.00 (m, 1H), 7.16-7.31 (m, 4H), 7.45 (s, 1H), 7.87 (brs, 1H). |
| Compound 32 | Mp. 244° C. (dec.). MS (EI): m/z 353 [M$^+$]. $^1$H-NMR (DMSO-$d_6$) δ: 1.94-2.84 (m, 13H), 3.19-3.42 (m, 4H), 6.59 (s, 1H), 6.98-6.99 (m, 1H), 7.14-7.19 (m, 2H), 7.27-7.29 (m, 1H). |
| Compound 33 | Mp. 195° C. (dec.) MS (EI): m/z 450 [M$^+$ + 1]. $^1$H-NMR (DMSO-$d_6$) δ: 1.33-1.37 (m, 2H), 1.46-1.47 (m, 4H), 1.96-2.83 (m, 17H), 3.19-3.44 (m, 4H), 6.89-7.00 (m, 1H), 7.16-7.21 (m, 2H), 7.29-7.30 (m, 1H), 7.43 (s, 1H), 8.29-8.31 (m, 1H). |
| Compound 34 | Mp. 176° C. (dec.). $^1$H-NMR (DMSO-$d_6$) δ: 1.25 (t, J = 7.1 Hz, 3H), 2.08-2.71 (m, 11H), 4.16 (q, J = 7.1 Hz, 2H), 4.90 (d, J = 12.1 Hz, 1H), 5.45 (d, J = 12.1 Hz, 1H), 6.52 (d, J = 16.1 Hz, 1H), 6.86-7.63 (m, 6H). |
| Compound 35 | Mp. 193° C. (dec.). MS (EI): m/z 368 [M$^+$ + 1]. $^1$H-NMR (DMSO-$d_6$) δ: 1.28-2.71 (m, 11H), 4.25 (d, J = 12.1 Hz, 1H), 4.85 (d, J = 12.1 Hz, 1H), 6.05 (d, J = 16.1 Hz, 1H), 6.47-6.99 (m, 6H). |
| Compound 36 | Mp. 179° C. (dec.). $^1$H-NMR (DMSO-$d_6$) δ: 1.23 (t, J = 7.1 Hz, 3H), 2.12-2.74 (m, 11H), 4.15 (q, J = 7.1 Hz, 2H), 4.80 (d, J = 12.1 Hz, 1H), 5.40 (d, J = 12.1 Hz, 1H), 6.16 (d, J = 16.1 Hz, 1H), 7.09-7.29 (m, 5H), 7.66 (d, J = 16.1 Hz, 1H). |
| Compound 37 | Mp. 229° C. (dec.). $^1$H-NMR (DMSO-$d_6$) δ: 2.12-2.74 (m, 11H), 4.80 (d, J = 12.1 Hz, 1H), 5.40 (d, J = 12.1 Hz, 1H), 6.07 (d, J = 16.1 Hz, 1H), 7.09-7.29 (m, 5H), 7.60 (d, J = 16.1 Hz, 1H), 12.14 (br, 1H). |
| Compound 38 | Mp. 113° C. (dec.). MS (EI): m/z 396 [M$^+$]. $^1$H-NMR (DMSO-$d_6$) δ: 1.94-2.83 (m, 15H), 3.23-3.40 (m, 7H), 6.89-7.00 (m, 1H), 7.23-7.30 (m, 3H), 7.47 (s, 1H), 8.45-8.46 (m, 1H). |
| Compound 39 | Mp. 140° C. (dec.). $^1$H-NMR (DMSO-$d_6$) δ: 2.28-3.71 (m, 19H), 7.01-7.11 (m, 1H), 7.19-7.25 (m, 2H), 7.33-7.34 (m, 1H), 7.66-7.77 (m, 1H), 8.07-8.21 (m, 3H), 8.84-9.15 (m, 1H), 11.12 (brs, 1H). |

TABLE 4

| Compound No. | Properties |
|---|---|
| Compound 40 | Mp. 194° C. (dec.). MS (EI): m/z 368 [M$^+$]. $^1$H-NMR (DMSO-$d_6$) δ: 2.03-2.85 (m, 13H), 3.20-3.44 (m, 2H), 3.67 (s, 3H), 6.99-7.01 (m, 1H), 7.16-7.25 (m, 2H), 7.29-7.33 (m, 2H), 11.63 (brs, 1H). |
| Compound 41 | Mp. 136° C. (dec.). MS (EI): m/z 395 [M$^+$]. $^1$H-NMR (DMSO-$d_6$) δ: 2.00-2.84 (m, 13H), 3.21-3.26 (m, 2H), 3.75 (dq, J = 16.4, 6.0 Hz, 2H), 7.00-7.01 (m, 2H), 7.16-7.21 (m, 2H), 7.29-7.33 (m, 2H), 7.50 (s, 1H), 8.60-8.63 (m, 1H). |
| Compound 42 | Mp. 167° C. (dec.). MS (EI): m/z 410 [M$^+$]. $^1$H-NMR (DMSO-$d_6$) δ: 2.05-2.86 (m, 13H), 3.22-3.34 (m, 2H), 3.64 (s, 3H), 3.90-4.01 (m, 2H), 7.00-7.02 (m, 1H), 7.21-7.24 (m, 2H), 7.29-7.30 (m, 1H), 7.50 (s, 1H), 8.86-8.88 (m, 1H). |

TABLE 4-continued

| Compound No. | Properties |
|---|---|
| Compound 43 | Mp. 138° C. (dec.). MS (EI): m/z 408 [M$^+$]. $^1$H-NMR (DMSO-d$_6$) δ: 1.89-2.84 (m, 13H), 3.24-3.64 (m, 10H), 7.01-7.04 (m, 2H), 7.14-7.31 (m, 3H). |
| Compound 44 | Mp. 246° C. (dec.). $^1$H-NMR (DMSO-d$_6$) δ: 1.25-1.28 (m, 3H), 2.42-3.63 (m, 11H), 4.24-4.28 (m, 2H), 4.88-4.91 (m, 1H), 5.45-5.48 (m, 1H), 7.12-7.57 (m, 5H), 10.99 (brs, 1H). |
| Compound 45 | Mp. 209°-212° C. $^1$H-NMR (DMSO-d$_6$) δ: 2.28-2.78 (m, 11H), 4.84 (d, J = 15.5 Hz, 1H), 5.41 (d, J = 15.5 Hz, 1H), 7.07-7.29 (m, 4H), 7.34 (s, 1H). |
| Compound 46 | Mp. 180°-184° C. $^1$H-NMR (DMSO-d$_6$) δ: 2.08-2.57 (m, 11H), 6.38 (d, J = 15.9 Hz, 1H), 7.02-7.43 (m, 6H), 7.57 (d, J = 15.9 Hz, 1H), 8.07 (s, 1H), 12.19 (br, 1H). |
| Compound 47 | Mp. 139°-141° C. MS (EI): m/z 407 [M$^+$]. $^1$H-NMR (DMSO-d$_6$) δ: 1.25 (t, J = 7.1 Hz, 3H), 2.06-2.70 (m, 11H), 3.73 (d, J = 13.6 Hz, 1H), 4.16-4.23 (m, 3H), 6.51 (d, J = 15.9 Hz, 1H), 7.17-7.27 (m, 3H), 7.37-7.39 (m, 1H), 7.62 (s, 1H), 7.79 (d, 3 = 15.9 Hz, 1H). |
| Compound 48 | Mp. 207° C. (dec.). MS (EI): m/z 379 [M$^+$]. $^1$H-NMR (DMSO-d$_6$) δ: 2.12-2.75 (m, 11H), 3.72 (d, J = 13.6 Hz, 1H), 4.23 (d, J = 13.6 Hz, 1H), 6.41 (d, J = 15.8 Hz, 1H), 7.18-7.39 (m, 4H), 7.57 (s, 1H), 7.70 (d, J = 15.8 Hz, 1H). |
| Compound 49 | Mp. 138° C. (dec.). MS (EI): m/z 368 [M$^+$ + 1]. $^1$H-NMR (DMSO-d$_6$) δ: 2.02-2.80 (m, 13H), 3.19-3.23 (m, 2H), 4.19 (d, J = 5.9 Hz, 2H), 5.49 (s, 2H), 6.36 (t, J = 5.9 Hz, 1H), 6.58 (s, 1H), 6.97-6.99 (m, 1H), 7.14-7.19 (m, 2H), 7.27-7.28 (m, 1H). |
| Compound 50 | Mp. 138°-139° C. MS (EI): m/z 381 [M$^+$]. $^1$H-NMR (DMSO-d$_6$) δ: 1.29 (t, J = 7.1 Hz, 3H), 2.00-2.71 (m, 11H), 3.77 (d, J = 13.7 Hz, 1H), 4.24-4.36 (m, 3H), 7.21-7.40 (m, 4H), 7.89 (s, 1H). |
| Compound 51 | Mp. 280°-283° C. MS (EI): m/z 353 [M$^+$]. $^1$H-NMR (DMSO-d$_6$) δ: 2.36-3.07 (m, 11H), 3.70 (d, J = 13.7 Hz, 1H), 4.30 (d, J = 13.7 Hz, 1H), 7.21-7.40 (m, 5H). |

TABLE 5

| Compound No. | Properties |
|---|---|
| Compound 52 | Mp. 111°-113° C. $^1$H-NMR (DMSO-d$_6$) δ: 2.02-3.43 (m, 19H), 4.69 (t, J = 5.4 Hz, 1H), 6.29 (d, J = 15.5 Hz, 1H), 6.97 (s, 1H), 7.01-7.31 (m, 4H), 7.34 (d, J = 15.5 Hz, 1H), 8.07 (t, J = 5.7 Hz, 1H). |
| Compound 53 | Mp. 114° C. (dec.). MS (EI): m/z 385 [M$^+$ + 1]. $^1$H-NMR (DMSO-d$_6$) δ: 2.13-2.72 (m, 11H), 3.23-3.45 (m, 4H), 4.70-4.74 (m, 1H), 4.82 (d, J = 15.4 Hz, 1H), 5.42 (d, J = 15.4 Hz, 1H), 7.07-7.29 (m, 4H), 7.44 (s, 1H), 8.39 (t, J = 5.7 Hz, 1H). |
| Compound 54 | Mp. 264° C. (dec.). MS (EI): m/z 355 [M$^+$ + 1]. $^1$H-NMR (DMSO-d$_6$) δ: 2.36-3.63 (m, 11H), 4.86 (d, J = 15.3 Hz, 1H), 5.44 (d, J = 15.3 Hz, 1H), 6.83-7.51 (m, 5H), 10.83-10.91 (br 1H), 12.32 (s, 1H). |
| Compound 55 | Mp. 105° C. (dec.). MS (EI): m/z 384 [M$^+$]. $^1$H-NMR (DMSO-d$_6$) δ: 2.10-2.72 (m, 11H), 3.26-3.50 (m, 4H), 4.68 (t, J = 5.7 Hz, 1H), 4.90 (d, J = 14.9 Hz, 1H), 5.46 (d, J = 14.9 Hz, 1H), 6.86-7.76 (m, 5H), 8.34 (t, J = 5.5 Hz, 1H). |
| Compound 56 | Mp. 206° C. (dec.). MS (EI): m/z 367 [M$^+$]. $^1$H-NMR (DMSO-d$_6$) δ: 1.04-1.07 (m, 3H), 2.48-3.43 (m, 15H), 3.85-3.87 (m, 1H), 6.66-6.67 (m, 1H), 7.02-7.32 (m, 4H), 10.78 (br, 1H), 12.55 (brs, 1H). |
| Compound 57 | Mp. 179° C. (dec.). MS (EI): m/z 370 [M$^+$ + 1]. $^1$H-NMR (DMSO-d$_6$) δ: 1.32-1.36 (m, 3H), 2.36-3.67 (m, 12H), 4.84-4.88 (m, 1H), 5.40-5.45 (m, 1H), 6.84-7.51 (m, 5H), 10.63-10.76 (m, 1H ), 12.31 (brs, 1H). |
| Compound 58 | Mp. 149° C. (dec.). MS (EI): m/z 356 [M$^+$ + 1]. $^1$H-NMR (DMSO-d$_6$) δ: 2.36-3.87 (m, 13H), 4.78-4.81 (m, 1H), 5.37-5.40 (m, 1H), 6.65-7.31 (m, 5H), 10.69 (brs, 1H ),12.60 (brs, 1H). |
| Compound 59 | Mp. 244° C. (dec.). MS (EI): m/z 352 [M$^+$ + 1]. $^1$H-NMR (DMSO-d$_6$) δ: 2.18-3.10 (m, 13H), 6.96-7.66 (m, 7H), 10.70 (br, 1H), 12.44 (brs, 1H). |
| Compound 60 | Mp. 212° C. (dec.). MS (EI): m/z 367 [M$^+$]. $^1$H-NMR (DMSO-d$_6$) δ: 1.36 (t, J = 6.4 Hz, 3H), 2.50-3.45 (m, 15H), 3.82-3.85 (m, 1H), 6.61 (s, 1H), 7.03-7.32 (m, 4H), 10.74-11.01 (br, 1H), 12.56 (brs, 1H). |
| Compound 61 | MS (EI): m/z 425 [M$^+$]. $^1$H-NMR (DMSO-d$_6$) δ: 1.18 (t, J = 6.7 Hz, 3H), 1.26 (t, J = 7.1 Hz, 3H), 2.17-2.23 (m, 2H), 2.42-2.45 (m, 1H), 2.82-3.36 (m, 7H), 3.61-3.63 (m, 1H), 3.74-3.77 (m, 1H), 4.04 (q, J = 7.1 Hz, 2H), 4.24 (q, J = 6.7 Hz, 2H), 7.04-7.05 (m, 1H), 7.18-7.23 (m, 2H), 7.31-7.32 (m, 1H), 7.45 (s, 1H). |
| Compound 62 | Mp. 155°-159° C. MS (EI): m/z 353 [M$^+$]. $^1$H-NMR (DMSO-d$_6$) δ: 1.26 (t, J = 6.8 Hz, 3H), 2.09-2.92 (m, 11H), 3.26-3.37 (m, 2H), 4.26 (q, J = 6.8 Hz, 2H), 7.02-7.04 (m, 1H), 7.16-7.21 (m, 2H), 7.29-7.31 (m, 1H), 7.40 (s, 1H). |

TABLE 6

| Compound No. | Properties |
| --- | --- |
| Compound 63 | MS (EI): m/z 396 [M$^+$]. $^1$H-NMR (DMSO-d$_6$) δ: 1.95-3.39 (m, 19H), 3.49 (s, 2H), 4.66 (t, J = 5.3 Hz, 1H), 6.55 (s, 1H), 6.97-6.99 (m, 1H), 7.14-7.19 (m, 2H), 7.27-7.28 (m, 1H), 8.02-8.04 (m, 1H). |
| Compound 64 | Mp. 86° C. (dec.). MS (EI): m/z 413 [M$^+$ + 1]. $^1$H-NMR (DMSO-d$_6$) δ: 1.25-1.28 (m, 3H), 2.18-3.58 (m, 16H), 4.61-4.64 (m, 1H), 4.81 (d, J = 15.3 Hz, 1H), 5.39 (d, J = 15.3 Hz, 1H), 6.78-7.42 (m, 5H), 7.88-7.97 (m, 1H). |
| Compound 65 | Mp. 251° C. (dec.). MS (EI): m/z 381 [M$^+$]. $^1$H-NMR (DMSO-d$_6$) δ: 1.45-1.46 (m, 6H), 1.99-3.23 (m, 15H), 6.58 (s, 1H), 6.99-7.29 (m, 4H). |
| Compound 66 | Mp. 122° C. (dec.). MS (EI): m/z 411 [M$^+$ + 1]. $^1$H-NMR (DMSO-d$_6$) δ: 2.16-2.71 (m, 11H), 3.22-3.24 (m, 2H), 3.43-3.47 (m, 2H), 4.74 (t, J = 5.5 Hz, 1H), 4.89 (d, J = 15.0 Hz, 1H), 5.44 (d, J = 15.0 Hz, 1H), 6.59 (d, J = 15.8 Hz, 1H), 6.85-7.09 (m, 2H), 7.34 (s, 1H), 7.35 (d, J = 15.8 Hz, 1H), 7.42-7.45 (m, 2H), 8.03 (t, J = 5.5 Hz, 1H). |
| Compound 67 | Mp. 198°-200° C. MS (EI): m/z 382 [M$^+$]. $^1$H-NMR (DMSO-d$_6$) δ: 2.01-3.45 (m, 19H), 4.70 (t, J = 5.6 Hz, 1H), 7.01-7.03 (m, 1H), 7.16-7.23 (m, 2H), 7.30-7.31 (m, 1H), 7.38 (s, 1H), 8.30-8.32 (m, 1H). |
| Compound 68 | Mp. 247°-250° C. $^1$H-NMR (DMSO-d$_6$) δ: 1.42 (s, 3H), 1.43 (s, 3H), 2.20-2.73 (m, 11H), 4.84 (d, J = 15.3 Hz, 1H), 5.40 (d, J = 15.3 Hz, 1H), 6.80-7.43 (m, 5H). |
| Compound 69 | Mp. 151° C. (dec.). MS (EI): m/z 396 [M$^+$]. $^1$H-NMR (DMSO-d$_6$) δ: 2.45-3.70 (m, 22H), 4.43-4.48 (br, 1H), 7.05-7.33 (m, 5H), 10.75-11.04 (br, 1H). |
| Compound 70 | Mp. 186°-188° C. MS (EI): m/z 396 [M$^+$]. $^1$H-NMR (DMSO-d$_6$) δ: 1.03 (d, J = 6.1 Hz, 3H), 1.96-3.74 (m, 18H), 4.71 (d, J = 4.7 Hz, 1H), 6.98-7.49 (m, 5H), 8.35-8.36 (m, 1H). |
| Compound 71 | Mp. 226°-229° C. $^1$H-NMR (DMSO-d$_6$) δ: 1.07-1.11 (m, 3H), 1.91-3.42 (m, 17H), 3.89-3.93 (m, 1H), 4.70 (dt, J = 21.9, 5.8 Hz, 1H), 6.97-7.52 (m, 5H), 8.02 (d, J = 7.9 Hz, 1H). |
| Compound 72 | Mp. 115° C. (dec.). $^1$H-NMR (DMSO-d$_6$) δ: 1.97-3.60 (m, 20H), 4.51-4.56 (m, 1H), 4.74-4.78 (m, 1H), 6.99-7.50 (m, 5H), 8.24-8.37 (m, 1H). |
| Compound 73 | $^1$H-NMR (DMSO-d$_6$) δ: 1.91-3.50 (m, 19H), 3.85-3.87 (m, 1H), 4.60-4.67 (m, 2H), 6.97-7.53 (m, 5H), 7.94 (d, J = 8.1 Hz, 1H). |
| Compound 74 | Mp. 112° C. (dec.). MS (EI): m/z 368 [M$^+$]. $^1$H-NMR (DMSO-d$_6$) δ: 1.98-3.23 (m, 18H), 7.03-7.48 (m, 5H), 10.46 (brs, 1H). |

TABLE 7

| Compound No. | Properties |
| --- | --- |
| Compound 75 | Mp. 228° C. (dec.). MS (EI): m/z 382 [M$^+$]. $^1$H-NMR (DMSO-d$_6$) δ: 1.21 (t, J = 7.1 Hz, 3H), 1.95-3.20 (m, 15H), 4.10 (q, J = 7.1 Hz, 2H), 6.23 (s, 1H), 6.97-7.28 (m, 4H), 10.35 (brs, 1H). |
| Compound 76 | Mp. 143°-146° C. MS (EI): m/z 396 [M$^+$]. $^1$H-NMR (DMSO-d$_6$) δ: 1.21-1.23 (m, 6H), 1.95-3.20 (m, 15H), 4.82-4.87 (m, 1H), 6.22 (s, 1H), 6.97-7.28 (m, 4H), 10.31 (brs, 1H). |
| Compound 77 | Mp. 191°-192° C. MS (EI): m/z 384 [M$^+$]. $^1$H-NMR (DMSO-d$_6$) δ: 1.97-3.50 (m, 17H), 4.44-4.56 (m, 2H), 6.99-7.50 (m, 5H), 8.63 (t, J = 5.6 Hz, 1H). |
| Compound 78 | Mp. 166° C. (dec.). MS (EI): m/z 354 [M$^+$]. $^1$H-NMR (DMSO-d$_6$) δ: 2.02-3.33 (m, 15H), 7.00-7.30 (m, 5H), 9.06 (br, 1H), 11.11 (br, 1H). |
| Compound 79 | Mp. 195°-197° C. MS (EI): m/z 420 [M$^+$]. $^1$H-NMR (DMSO-d$_6$) δ: 1.97-3.33 (m, 15H), 3.97-4.08 (m, 2H), 7.00-7.31 (m, 4H), 7.59 (s, 1H), 8.99-9.01 (m, 1H). |
| Compound 80 | Mp. 220°-222° C. $^1$H-NMR (DMSO-d$_6$) δ: 1.24-1.26 (m, 6H), 1.87-3.31 (m, 15H), 3.46 (d, J = 5.9 Hz, 2H), 4.84 (t, J = 5.9 Hz, 1H), 6.97-7.31 (m, 4H), 7.45 (s, 1H), 7.52 (s, 1H). |
| Compound 81 | Mp. 188°-191° C. MS (EI): m/z 470 [M$^+$]. $^1$H-NMR (DMSO-d$_6$) δ: 1.97-3.33 (m, 15H), 3.99-4.18 (m, 2H), 7.00-7.31 (m, 4H), 7.59 (s, 1H), 8.98 (t, J = 6.2 Hz, 1H). |
| Compound 82 | Mp. 175° C. (dec.). MS (EI): m/z 398 [M$^+$]. $^1$H-NMR (DMSO-d$_6$) δ: 1.96-3.51 (m, 20H), 6.96-7.48 (m, 5H), 8.51-8.61 (m, 1H). |
| Compound 83 | Mp. 110° C. (dec.). MS (EI): m/z 397 [M$^+$]. $^1$H-NMR (DMSO-d$_6$) δ: 1.98-3.66 (m, 19H), 4.77 (brs, 1H), 4.96-5.02 (m, 2H), 7.02-7.53 (m, 5H). |
| Compound 84 | Mp. 144°-146° C. MS (EI): m/z 382 [M$^+$]. $^1$H-NMR (DMSO-d$_6$) δ: 2.00-3.39 (m, 18H), 3.72 (s, 3H), 7.03-7.31 (m, 4H), 7.48 (s, 1H). |
| Compound 85 | Mp. 180°-183° C. $^1$H-NMR (DMSO-d$_6$) δ: 0.86 (d, J = 7.4 Hz, 3H), 1.47-1.51 (m, 2H), 1.95-3.35 (m, 17H), 6.99-7.30 (m, 4H), 7.45 (s, 1H), 8.36 (t, J = 5.6 Hz, 1H). |

TABLE 7-continued

| Compound No. | Properties |
|---|---|
| Compound 86 | Mp. 185°-187° C. ¹H-NMR (DMSO-d₆) δ: 1.98-3.33 (m, 15H), 3.79-3.87 (m, 2H), 5.08 (d, J = 10.2 Hz, 1H), 5.15 (d, J = 17.3 Hz, 1H), 5.81-5.89 (m, 1H), 6.99-7.30 (m, 4H), 7.50 (s, 1H), 8.58 (t, J = 5.6 Hz, 1H). |
| Compound 87 | Mp. 194°-197° C. MS (EI): m/z 367 [M⁺]. ¹H-NMR (DMSO-d₆) δ: 2.12-2.76 (m, 11H), 3.65 (d, J = 13.5 Hz, 1H), 3.81 (s, 2H), 4.19 (d, J = 13.5 Hz, 1H), 7.00 (s, 1H), 7.16-7.37 (m, 4H). |
| Compound 88 | Mp. 160° C. (dec.). MS (EI): m/z 397 [M⁺]. ¹H-NMR (DMSO-d₆) δ: 1.18 (m, 3H), 2.23-4.05 (m, 14H), 7.04-7.32 (m, 5H). |

TABLE 8

| Compound No. | Properties |
|---|---|
| Compound 89 | Mp. >280° C. MS (EI): m/z 337 [M⁺]. ¹H-NMR (DMSO-d₆) δ: 2.10-2.59 (m, 11H), 7.02 (d, J = 11.9 Hz, 1H), 7.15-7.41 (m, 4H), 7.48 (d, J = 11.9 Hz, 1H), 8.23 (s, 1H). |
| Compound 90 | MS (EI): m/z 395 [M⁺]. ¹H-NMR (DMSO-d₆) δ: 1.24-1.28 (m, 3H), 2.00-4.26 (m, 17H), 7.05-7.45 (m, 5H). |
| Compound 91 | Mp. 176° C. (dec.). MS (EI): m/z 367 [M⁺]. ¹H-NMR (DMSO-d₆) δ: 1.94-3.93 (m, 15H), 7.05-7.45 (m, 5H). |
| Compound 92 | Mp. 169°-173° C. MS (EI): m/z 425 [M⁺]. ¹H-NMR (DMSO-d₆) δ: 1.23-1.27 (m, 3H), 2.10-3.38 (m, 16H), 4.21-4.28 (m, 2H), 7.03-7.44 (m, 5H). |
| Compound 93 | Mp. 136°-140° C. MS (EI): m/z 367 [M⁺]. ¹H-NMR (DMSO-d₆) δ: 1.99-3.17 (m, 19H), 6.45 (s, 1H), 6.97-7.27 (m, 4H). |
| Compound 94 | Mp. 119° C. (dec.). MS (EI): m/z 378 [M⁺]. ¹H-NMR (DMSO-d₆) δ: 2.14-3.46 (m, 16H), 7.03-7.35 (m, 5H). |
| Compound 95 | Mp. 109°-111° C. ¹H-NMR (DMSO-d₆) δ: 1.18 (t, J = 7.1 Hz, 3H), 1.94-2.95 (m, 13H), 3.27-3.36 (m, 2H), 4.29 (q, J = 7.1 Hz, 2H), 6.81-6.82 (m, 1H), 7.29-7.30 (m, 1H), 7.45-7.47 (m, 1H), 7.56-7.57 (m, 1H), 7.78-7.81 (m, 1H). |
| Compound 96 | Mp. >280° C. ¹H-NMR (DMSO-d₆) δ: 2.16-2.93 (m, 13H), 3.28-3.35 (m, 2H), 6.81-6.82 (m, 1H), 7.30-7.31 (m, 1H), 7.42-7.43 (m, 1H), 7.57-7.58 (m, 1H), 7.77-7.79 (m, 1H). |
| Compound 97 | Mp. 88°-92° C. MS (EI): m/z 395 [M⁺]. ¹H-NMR (DMSO-d₆) δ: 1.15 (t, J = 7.1 Hz, 3H), 1.94-3.21 (m, 19H), 4.04 (q, J = 7.1 Hz, 2H), 6.50 (s, 1H), 6.96-7.28 (m, 4H). |
| Compound 98 | Mp. 207°-212° C. MS (EI): m/z 367 [M⁺]. ¹H-NMR (DMSO-d₆) δ: 1.95-3.22 (m, 19H), 6.45 (s, 1H), 6.97-7.28 (m, 4H). |
| Compound 99 | Mp. 109° C. (dec.). ¹H-NMR (DMSO-d₆) δ: 1.26-1.47 (m, 6H), 2.37-5.43 (m, 27H), 6.81-7.50 (m, 5H), 10.84-10.92 (m, 1H). |
| Compound 100 | Mp. 98° C. (dec.). MS (EI): m/z 370 [M⁺ + 1]. ¹H-NMR (DMSO-d₆) δ: 2.30-3.33 (m, 15H), 4.82 (d, J = 15.5 Hz, 1H), 5.40 (d, J = 15.5 Hz, 1H), 6.80-6.81 (m, 1H), 6.99 (s, 1H), 7.02-7.14 (m, 2H), 7.46-7.47 (m, 1H). |
| Compound 101 | Mp. >280° C. MS (EI): m/z 464 [M⁺]. ¹H-NMR (DMSO-d₆) δ: 1.24-1.28 (m, 3H), 1.87-3.57 (m, 26H), 4.23-4.29 (m, 2H), 7.07-7.52 (m, 5H), 10.94-11.34 (m, 2H). |
| Compound 102 | Mp. 161° C. (dec.). MS (EI): m/z 436 [M⁺]. ¹H-NMR (DMSO-d₆) δ: 1.83-3.25 (m, 26H), 6.99-7.30 (m, 5H). |
| Compound 103 | Mp. 185° C. (dec.). MS (EI): m/z 381 [M⁺]. ¹H-NMR (DMSO-d₆) δ: 1.21 (t, J = 7.3 Hz, 3H), 1.25-1.31 (m, 3H), 2.25-3.65 (m, 14H), 4.22-4.27 (m, 2H), 7.07-7.52 (m, 5H), 10.42 (br, 1H). |

TABLE 9

| Compound No. | Properties |
|---|---|
| Compound 104 | Mp. 197°-200° C. ¹H-NMR (DMSO-d₆) δ: 1.93-2.81 (m, 13H), 3.19-3.32 (m, 2H), 4.42-4.43 (m, 2H), 5.06 (br, 1H), 6.76-6.77 (m, 1H), 6.96-6.97 (m, 1H), 7.10-7.11 (m, 1H), 7.22-7.26 (m, 2H). |
| Compound 105 | Mp. 123°-125° C. MS (EI): m/z 398 [M⁺ + 1]. ¹H-NMR (DMSO-d₆) δ: 1.26 (t, J = 7.1 Hz, 3H), 2.07-3.50 (m, 16H), 4.22-4.26 (m, 2H), 4.37 (t, J = 5.4 Hz, 1H), 7.02-7.31 (m, 4H), 7.41 (s, 1H). |
| Compound 106 | Mp. 123° C. MS (des.). (EI): m/z 381 [M⁺]. ¹H-NMR (DMSO-d₆) δ: 1.17 (t, J = 7.1 Hz, 3H), 2.46-3.65 (m, 17H), 4.06 (q, J = 7.1 Hz, 2H), 6.83-7.39 (m, 5H). |
| Compound 107 | Mp. 252° C. (dec.). ¹H-NMR (DMSO-d₆) δ: 2.32-3.72 (m, 16H), 5.33 (s, 1H), 7.08-7.42 (m, 5H), 10.05 (br, 1H), 13.02 (brs, 1H). |
| Compound 108 | Mp. >280° C. MS (EI): m/z 353 [M⁺]. ¹H-NMR (DMSO-d₆) δ: 1.17-1.35 (m, 3H), 2.30-3.57 (m, 14H), 7.09-7.43 (m, 5H), 10.30-10.43 (br, 1H), 13.01 (brs, 1H). |

TABLE 9-continued

| Compound No. | Properties |
| --- | --- |
| Compound 109 | Mp. 123°-124° C. MS (EI): m/z 555 [M⁺]. ¹H-NMR (DMSO-d$_6$) δ: 1.26 (t, J = 7.1 Hz, 3H), 1.31 (s, 9H), 1.77-3.37 (m, 18H), 4.21-4.28 (m, 2H), 7.00-7.30 (m, 4H), 7.38 (s, 1H), 7.53-7.91 (m, 4H). |
| Compound 110 | Mp. 85°-89° C. MS (EI): m/z 484 [M⁺ + 1]. ¹H-NMR (DMSO-d$_6$) δ: 1.18-1.23 (m, 3H), 1.27 (t, J = 7.1 Hz, 3H), 2.36-3.82 (m, 16H), 4.11-4.27 (m, 6H), 7.06-7.50 (m, 5H), 10.42 (brs, 1H). |
| Compound 111 | Mp. 135° C. (dec.). MS (EI): m/z 456 [M⁺ + 1]. ¹H-NMR (DMSO-d$_6$) δ: 1.26 (t, J = 7.1 Hz, 3H), 2.28-3.39 (m, 14H), 3.67 (t, J = 5.1 Hz, 2H), 3.86 (s, 2H), 4.22-4.26 (m, 2H), 7.07-732 (m, 4H), 7.46 (s, 1H). |
| Compound 112 | Mp. 157°-159° C. MS (EI): m/z 321 [M⁺]. ¹H-NMR (DMSO-d$_6$) δ: 1.97-2.86 (m, 13H), 3.26-3.30 (m, 2H), 5.09-5.11 (m, 1H), 5.36-539 (m, 1H), 6.78-6.84 (m, 2H), 7.02-7.04 (m, 2H), 7.20-7.23 (m, 2H), 7.33-7.34 (m, 1H). |
| Compound 113 | ¹H-NMR (DMSO-d$_6$) δ: 1.17 (t, J = 7.1 Hz, 3H), 2.66-2.70 (m, 1H), 2.94-3.07 (m, 4H), 3.22-3.37 (m, 3H), 3.59-3.66 (m, 2H), 4.04-4.08 (m, 2H), 4.85 (d, J = 15.4 Hz, 1H), 5.44 (d, J = 15.4 Hz, 1H), 6.83-6.85 (m, 1H), 7.05-7.08 (m, 2H), 7.15-7.17 (m, 1H), 7.48-7.50 (m, 1H), 9.10 (brs, 1H), 9.32 (brs, 1H). |
| Compound 114 | Mp. 202° C. (dec.) ¹H-NMR (DMSO-d$_6$) δ: 2.20-2.94 (m, 8H), 3.38-3.47 (m, 2H), 4.82 (d, J = 15.4 Hz, 1H), 5.40 (d, = 15.4 Hz, 1H), 6.78-6.79 (m, 1H), 6.98-7.09 (m, 3H), 7.41-7.43 (m, 1H). |
| Compound 115 | Mp. 118°-120° C. ¹H-NMR (DMSO-d$_6$) δ: 1.30 (t, J = 7.1, 3H), 1.99-3.31 (m, 15H), 4.28 (q, J = 7.1 Hz, 2H), 6.74-7.81 (m, 5H). |
| Compound 116 | Mp. 199°-203° C. MS (EI): m/z 370 [M⁺ + 1]. ¹H-NMR (DMSO-d$_6$) δ: 2.36-3.78 (m, 16H), 4.98-5.04 (m, 1H), 5.53-5.62 (m, 1H), 6.95-7.13 (m, 4H), 7.48-7.56 (m, 1H), 10.64-10.74 (m, 1H). |

TABLE 10

| Compound No. | Properties |
| --- | --- |
| Compound 117 | Mp. 240°-245° C. MS (EI): m/z 356 [M⁺ + 1]. ¹H-NMR (DMSO-d$_6$) δ: 2.13-2.58 (m, 1H), 3.46-3.52 (m, 2H), 4.97 (d, J = 15.0 Hz, 1H), 5.53 (d, J = 15.0 Hz, 1H), 6.91-6.97 (m, 3H), 7.06-7.09 (m, 1H), 7.42-7.43 (m, 1H). |
| Compound 118 | Mp. 156°-158° C. MS (EI): m/z 400 [M⁺ + 1]. ¹H-NMR (DMSO-d$_6$) δ: 2.36-3.81 (m, 17H), 4.83-4.88 (m, 1H), 5.31-5.46 (m, 2H), 6.84-7.18 (m, 4H), 7.48-7.52 (m, 1H), 10.28-10.41 (m, 1H). |
| Compound 119 | Mp. 242° C. (dec.). MS (EI): m/z 386 [M⁺ + 1]. ¹H-NMR (DMSO-d$_6$) δ: 2.28-2.71 (m, 10H), 3.49-3.51 (m, 4H), 4.82 (d, J = 15.4 Hz, 1H), 5.40 (d, J = 15.4 Hz, 1H), 6.78-6.79 (m, 1H), 6.98-7.03 (m, 2H), 7.10-7.13 (m, 1H), 7.41-7.42 (m, 1H). |
| Compound 120 | Mp. 174° C. (dec.). MS (EI): m/z 397 [M⁺]. ¹H-NMR (DMSO-d$_6$) δ: 1.41-1.48 (m, 5H), 2.16-2.83 (m, 12H), 3.30-3.40 (m, 4H), 7.02-7.04 (m, 1H), 7.16-7.22 (m, 2H), 7.29-730 (m, 2H). |
| Compound 121 | Mp. 258° C. (dec.). ¹H-NMR (DMSO-d$_6$) δ: 2.18-3.24 (m, 15H), 6.74-7.79 (m, 5H). |
| Compound 122 | MS (EI): m/z 371 [M⁺]. ¹H-NMR (DMSO-d$_6$) δ: 2.28-2.70 (m, 12H), 3.48-3.57 (m, 4H), 4.35-4.39 (m, 1H), 4.56-4.58 (m, 1H), 4.78-5.40 (m, 2H), 6.77-7.41 (m, 5H). |
| Compound 123 | Mp. 174°-177° C. MS (EI): m/z 397 [M⁺]. ¹H-NMR (DMSO-d$_6$) δ: 1.76-1.80 (m, 2H), 2.27-3.70 (m, 18H), 4.82-4.86 (m, 1H), 5.40-5.44 (m, 1H), 6.82-6.83 (m, 1H), 6.96-7.11 (m, 3H), 7.48-7.50 (m, 1H), 11.00-11.08 (m, 1H). |
| Compound 124 | Mp. 114°-118° C. MS (EI): m/z 383 [M⁺]. ¹H-NMR (DMSO-d$_6$) δ: 1.72-1.77 (m, 2H), 2.18-2.72 (m, 15H), 4.81 (d, J = 15.4 Hz, 1H), 5.39 (d, J = 15.4 Hz, 1H), 6.77-6.78 (m, 1H), 6.89-7.07 (m, 3H), 7.40-7.42 (m, 1H). |
| Compound 125 | Mp. 238° C. (dec.). ¹H-NMR (DMSO-d$_6$) δ: 2.31-2.72 (m, 12H), 3.50-3.55 (m, 2H), 4.83 (d, J = 15.1 Hz, 1H), 5.41 (d, J = 15.1 Hz, 1H), 6.79-6.80 (m, 1H), 7.00-7.14 (m, 3H), 7.42-7.44 (m, 1H). |
| Compound 126 | ¹H-NMR (DMSO-d$_6$) δ: 2.65-2.71 (m, 1H), 2.92-3.07 (m, 4H), 3.22-3.37 (m, 3H), 3.60 (s, 3H), 3.65 (s, 2H), 4.85 (d, J = 15.4 Hz, 1H), 5.44 (d, J = 15.4 Hz, 1H), 6.83-6.85 (m, 1H), 7.05-7.08 (m, 2H), 7.15-7.18 (m, 1H), 7.48-7.50 (m, 1H), 9.15 (brs, 1H), 9.39 (brs, 1H). |
| Compound 127 | Mp. 227°-231° C. ¹H-NMR (DMSO-d$_6$) δ: 1.17-1.32 (m, 3H), 2.35-3.66 (m, 15H), 4.83-4.88 (m, 1H), 5.40-5.46 (m, 1H), 6.83-6.85 (m, 1H), 7.05-7.20 (m, 3H), 7.50-7.52 (m, 1H), 10.52-10.76 (m, 1H). |
| Compound 128 | Mp. 255°-259° C. MS (EI): m/z 369 [M⁺]. ¹H-NMR (DMSO-d$_6$) δ: 1.01 (t, J = 6.9 Hz, 3H), 2.25-2.71 (m, 10H), 3.49-5.01 (m, 2H), 4.82 (d, J = 15.4 Hz, 1H), 5.41 (d, J = 15.4 Hz, 1H), 6.78-6.80 (m, 1H), 6.99-7.13 (m, 3H), 7.41-7.42 (m, 1H). |

TABLE 11

| Compound No. | Properties |
| --- | --- |
| Compound 129 | Mp. 221°-224° C. $^1$H-NMR (DMSO-$d_6$) δ: 0.87-0.96 (m, 3H), 1.67-1.72 (m, 2H), 2.35-3.66 (m, 15H), 4.83-4.88 (m, 1H), 5.40-5.46 (m, 1H), 6.82-6.85 (m, 1H), 7.05-7.19 (m, 3H), 7.49-7.52 (m, 1H), 10.51-10.73 (m, 1H). |
| Compound 130 | Mp. 203°-206° C. $^1$H-NMR (DMSO-$d_6$) δ: 0.86 (t, J = 7.4 Hz, 3H), 1.41-1.47 (m, 2H), 2.24-2.71 (m, 10H), 3.51-3.55 (m, 2H), 4.82 (d, J = 15.4 Hz, 1H), 5.41 (d, J = 15.4 Hz, 1H), 6.78-6.79 (m, 1H), 6.99-7.13 (m, 3H), 7.41-7.42 (m, 1H). |
| Compound 131 | Mp. 236° (dec.). $^1$H-NMR (DMSO-$d_6$) δ: 1.23-1.34 (m, 6H), 2.42-3.66 (m, 14H), 4.83-4.88 (m, 1H), 5.40-5.47 (m, 1H), 6.82-6.86 (m, 1H), 7.05-7.18 (m, 3H), 7.49-7.52 (m, 1H), 10.21-10.48 (m, 1H). |
| Compound 132 | Mp. 249°-253° C. $^1$H-NMR (DMSO-$d_6$) δ: 0.96-0.98 (m, 6H), 2.24-2.74 (m, 9H), 3.51-3.54 (m, 2H), 4.82 (d, J = 15.4 Hz, 1H), 5.41 (d, J = 15.4 Hz, 1H), 6.78-6.79 (m, 1H), 6.99-7.13 (m, 3H), 7.41-7.42 (m, 1H). |
| Compound 133 | Mp. 223° (dec.). $^1$H-NMR (DMSO-$d_6$) δ: 0.87-0.96 (m, 3H), 1.26 (t, J = 7.1 Hz, 3H), 1.64-1.69 (m, 2H), 2.30-3.48 (m, 14H), 4.24-4.31 (m, 2H), 7.06-7.12 (m, 1H), 7.19-7.35 (m, 3H), 7.48-7.51 (m, 1H), 10.43-10.49 (m, 1H). |
| Compound 134 | Mp. > 280° C. $^1$H-NMR (DMSO-$d_6$) δ: 0.88-0.94 (m, 3H), 1.66-1.76 (m, 2H), 230-4.02 (m, 14H), 7.07-7.41 (m, 5H), 10.47-10.58 (m, 1H), 13.03 (brs, 1H). |
| Compound 135 | Mp. 208°-210° C. $^1$H-NMR (DMSO-$d_6$) δ: 1.77-1.81 (m, 2H), 2.27-2.31 (m, 2H), 2.50-2.67 (m, 4H), 2.94-3.32 (m, 6H), 3.56 (s, 3H), 4.83 (d, J = 15.5 Hz, 1H), 5.42 (d, J = 15.5 Hz, 1H), 6.81-6.83 (m, 1H), 6.98-7.11 (m, 3H), 7.48-7.49 (m, 1H), 9.05-9.37 (m, 2H). |
| Compound 136 | Mp. 243° C. (dec.). $^1$H-NMR (DMSO-$d_6$) δ: 1.75-1.78 (m, 2H), 2.18-2.22 (m, 2H), 2.49-2.67 (m, 4H), 2.93-3.32 (m, 6H), 4.83 (d, J = 15.5 Hz, 1H), 5.42 (d, J = 15.5 Hz, 1H), 6.81-6.83 (m, 1H), 6.98-7.12 (m, 3H), 7.48-7.49 (m, 1H), 8.97-9.13 (m, 2H), 12.01-12.12 (m, 1H). |
| Compound 137 | $^1$H-NMR (DMSO-$d_6$) δ: 0.82-0.90 (m, 3H), 1.52-1.61 (m, 2H), 2.68-3.23 (m, 8H), 3.64 (s, 2H), 3.92-4.02 (m, 2H), 4.84 (d, J = 15.5 Hz, 1H), 5.43 (d, J = 15.5 Hz, 1H), 6.83-7.50 (m, 5H), 9.07-9.36 (m, 2H). |
| Compound 138 | Mp. 148°-151° C. $^1$H-NMR (DMSO-$d_6$) δ: 1.82-1.99 (m, 2H), 2.36-3.75 (m, 19H), 4.76-4.88 (m, 2H), 5.40-5.46 (m, 1H), 6.84-6.86 (m, 1H), 7.05-7.18 (m, 3H), 7.50-7.52 (m, 1H), 10.21-10.43 (m, 1H). |
| Compound 139 | Mp. 229° C. (dec.). MS (EI): m/z 399 [M$^+$]. $^1$H-NMR (DMSO-$d_6$) δ: 1.57-1.60 (m, 2H), 2.22-2.70 (m, 10H), 3.42-3.51 (m, 4H), 4.82 (d, J = 15.4 Hz, 1H), 5.40 (d, J = 15.4 Hz, 1H), 6.78-6.79 (m, 1H), 6.99-7.12 (m, 3H), 7.41-7.42 (m, 1H). |

TABLE 12

| Compound No. | Properties |
| --- | --- |
| Compound 140 | Mp. 144°-145° C. $^1$H-NMR (DMSO-$d_6$) δ: 1.16-1.19 (m, 3H), 2.36-3.63 (m, 13H), 4.02-4.4.08 (m, 2H), 4.85-4.88 (m, 1H), 5.42-5.46 (m, 1H), 6.84-6.85 (m, 1H), 7.08-7.18 (m, 3H), 7.50-7.52 (m, 1H), 10.56-10.21 (m, 1H). |
| Compound 141 | Mp. 214°-216° C. $^1$H-NMR (DMSO-$d_6$) δ: 1.15-1.32 (m, 3H), 1.77-1.81 (m, 2H), 2.28-3.70 (m, 17H), 4.81-4.86 (m, 1H), 5.38-4.55 (m, 1H), 6.81-7.11 (m, 4H), 7.49-7.50 (m, 1H), 10.51-10.69 (m, 1H). |
| Compound 142 | $^1$H-NMR (DMSO-$d_6$) δ: 1.00-1.04 (m, 3H), 1.73-1.77 (m, 2H), 2.17-2.73 (m, 14H), 4.81 (d, J = 15.4 Hz, 1H), 5.39 (d, J = 15.4 Hz, 1H), 6.77-6.78 (m, 1H), 6.90-7.07 (m, 3H), 7.41-7.42 (m, 1H). |
| Compound 143 | $^1$H-NMR (DMSO-$d_6$) δ: 1.09 (t, J = 7.1 Hz, 3H), 2.51-3.31 (m, 8H), 4.17 (q, J = 7.1 Hz, 2H), 4.93 (d, J = 14.9 Hz, 1H), 5.49 (d, J = 14.9 Hz, 1H), 6.57 (d, J = 16.0 Hz, 1H), 6.90-6.91 (m, 1H), 7.08-7.10 (m, 1H), 7.49-7.65 (m, 4H), 9.07-9.24 (m, 2H). |
| Compound 144 | Mp. 217° C. (dec.). MS (EI): m/z 353 [M$^+$]. $^1$H-NMR (DMSO-$d_6$) δ: 2.26-2.94 (m, 9H), 4.90 (d, J = 14.8 Hz, 1H), 5.45 (d, J = 14.8 Hz, 1H), 6.39-6.43 (m, 1H), 6.85-6.86 (m, 1H), 7.04-7.06 (m, 1H), 7.36-7.55 (m, 4H). |
| Compound 145 | $^1$H-NMR (DMSO-$d_6$) δ: 1.23 (t, J = 7.1 Hz, 3H), 2.42-3.27 (m, 12H), 4.16 (q, J = 7.1 Hz, 2H), 6.09 (d, J = 15.6 Hz, 1H), 7.07-7.33 (m, 5H), 7.71 (d, J = 15.6 Hz, 1H), 9.03-9.08 (br, 1H). |
| Compound 146 | Mp. 264° C. (dec.). $^1$H-NMR (MSO-$d_6$) δ: 2.07-2.44 (m, 5H), 2.57-2.92 (m, 5H), 3.21-3.47 (m, 2H), 5.94-5.97 (m, 1H), 6.83-7.30 (m, 6H). |
| Compound 147 | Mp. 191°-193° C. $^1$H-NMR (DMSO-$d_6$) δ: 1.15 (t, J = 7.1 Hz, 3H), 1.99-3.31 (m, 17H), 4.08 (q, J = 7.1 Hz, 2H), 6.74-7.40 (m, 5H), 10.83 (brs, 1H). |
| Compound 148 | Mp. 171°-174° C. $^1$H-NMR (DMSO-$d_6$) δ: 2.64-3.49 (m, 17H), 6.77-7.40 (m, 5H), 10.74 (brs, 1H), 12.27 (brs, 1H). |
| Compound 149 | Mp. 250° C. (dec.). MS (EI): m/z 395 [M$^+$]. $^1$H-NMR (DMSO-$d_6$) δ: 1.22-1.34 (m, 9H), 2.30-3.57 (m, 13H), 4.22-4.27 (m, 2H), 7.06-7.61 (m, 5H), 10.36 (m, 1H). |
| Compound 150 | Mp. > 280° C. $^1$H-NMR (DMSO-$d_6$) δ: 0.94-0.96 (m, 6H), 2.13-3.23 (m, 13H), 6.95-7.28 (m, 5H). |

TABLE 12-continued

| Compound No. | Properties |
| --- | --- |
| Compound 151 | Mp. 149° C. (dec.). ¹H-NMR (DMSO-d₆) δ: 1.99-3.29 (m, 15H), 3.48 (s, 2H), 6.76-7.27 (m, 5H). |
| Compound 152 | Mp. 186° C. (dec.). ¹H-NMR (DMSO-d₆) δ: 1.14 (t, J = 7.1 Hz, 3H), 1.49-1.51 (m, 6H), 2.30-3.30 (m, 13H), 4.05 (q, J = 7.1 Hz, 2H), 6.61-6.64 (m, 1H), 7.04-7.31 (m, 4H), 8.87-9.02 (m, 2H). |

TABLE 13

| Compound No. | Properties |
| --- | --- |
| Compound 153 | Mp. > 280° C. ¹H-NMR (DMSO-d₆) δ: 1.48 (s, 6H), 2.31-3.30 (m, 12H), 6.61-6.64 (m, 1H), 7.04-7.31 (m, 4H), 8.95-9.06 (m, 2H), 12.52 (brs, 1H). |
| Compound 154 | Mp. 247° C. (dec.). ¹H-NMR (DMSO-d₆) δ: 1.13-1.31 (m, 6H), 1.50 (s, 6H), 2.26-3.58 (m, 14H), 4.03-4.07 (m, 2H), 6.64-6.65 (m, 1H), 7.02-7.32 (m, 4H), 10.32-10.86 (m, 1H). |
| Compound 155 | Mp. 255° C. (dec.). ¹H-NMR (DMSO-d₆) δ: 0.95-1.01 (m, 3H), 1.45-1.51 (m, 6H), 2.08-3.23 (m, 14H), 6.58-7.24 (m, 5H). |
| Compound 156 | Mp. 164°-166° C. ¹H-NMR (DMSO-d₆) δ: 1.76-1.80 (m, 2H), 2.27-3.70 (m, 18H), 4.82-4.86 (m, 1H), 5.40-5.44 (m, 1H), 6.82-6.83 (m, 1H), 6.96-7.11 (m, 3H), 7.48-7.50 (m, 1H), 11.00-11.08 (m, 1H). |
| Compound 157 | Mp. 121°-123° C. MS (EI): m/z 397 [M⁺]. ¹H-NMR (DMSO-d₆) δ: 1.47-1.53 (m, 4H), 2.14-2.55 (m, 15H), 4.80 (d, J = 15.4 Hz, 1H), 5.39 (d, J = 15.4 Hz, 1H), 6.77-6.78 (m, 1H), 6.89-7.07 (m, 3H), 7.40-7.42 (m, 1H). |
| Compound 158 | Mp. 114°-117° C. MS (EI): m/z 407 [M⁺]. ¹H-NMR (DMSO-d₆) δ: 0.99 (t, J = 7.2 Hz, 3H), 1.23 (t, J = 7.1 Hz, 3H), 1.99-3.29 (m, 14H), 4.12-4.16 (m, 2H), 6.05 (d, J = 15.7 Hz, 1H), 7.01-7.02 (m, 1H), 7.15-7.20 (m, 2H), 7.25 (s, 1H), 7.29-7.31 (m, 1H), 7.72 (d, J = 15.7 Hz, 1H). |
| Compound 159 | Mp. 223° C. (dec.). MS (EI): m/z 379 [M⁺]. ¹H-NMR (DMSO-d₆) δ: 1.92-1.30 (m, 3H), 2.20-3.62 (m, 14H), 6.01 (d, J = 15.7 Hz, 1H), 7.04-7.68 (m, 6H), 9.99-10.41 (m, 1H), 12.35 (brs, 1H). |
| Compound 160 | Mp. 123°-124° C. MS (EI): m/z 381 [M⁺]. ¹H-NMR (DMSO-d₆) δ: 0.99 (t, J = 7.1 Hz, 3H), 1.30 (t, J = 7.1 Hz, 3H), 2.05-3.33 (m, 14H), 4.25-4.32 (m, 2H), 6.73-6.75 (m, 1H), 7.34-7.55 (m, 3H), 7.79-7.81 (m, 1H). |
| Compound 161 | Mp. 219°-222° C. MS (EI): m/z 353 [M⁺]. ¹H-NMR (DMSO-d₆) δ: 1.02 (t, J = 7.1 Hz, 3H), 2.18-3.32 (m, 14H), 6.74-6.75 (m, 1H), 7.35-7.55 (m, 3H), 7.77-7.79 (m, 1H). |
| Compound 162 | Mp. 156°-158° C. ¹H-NMR (DMSO-d₆) δ: 1.47-1.53 (m, 3H), 2.16-2.87 (m, 17H), 4.80 (d, J = 15.4 Hz, 1H), 5.39 (d, J = 15.4 Hz, 1H), 6.76-6.78 (m, 1H), 6.89-7.06 (m, 3H), 7.39-7.40 (m, 1H). |
| Compound 163 | Mp. 233° C. (dec.). MS (EI): m/z 480 [M⁺]. ¹H-NMR (DMSO-d₆) δ: 1.39-2.23 (m, 8H), 2.50-3.66 (m, 21H), 4.83-4.89 (m, 1H), 5.41-5.46 (m, 1H), 6.83-6.86 (m, 1H), 7.07-7.20 (m, 3H), 7.50-7.52 (m, 1H), 10.27-10.50 (m, 1H), 11.06-11.26 (m, 1H). |
| Compound 164 | Mp. 123° C. (dec.). MS (EI): m/z 466 [M⁺]. ¹H-NMR (DMSO-d₆) δ: 1.40-1.69 (m, 8H), 2.31-2.72 (m, 16H), 3.44-3.52 (m, 2H), 4.82 (d, J = 15.4 Hz, 1H), 5.40 (d, J = 15.4 Hz, 1H), 6.78-6.79 (m, 1H), 6.98-7.02 (m, 2H), 7.10-7.12 (m, 1H), 7.41-7.42 (m, 1H). |

TABLE 14

| Compound No. | Properties |
| --- | --- |
| Compound 165 | Mp. 200°-203° C. ¹H-NMR (DMSO-d₆) δ: 2.31-3.69 (m, 14H), 4.73-4.83 (m, 3H), 5.36-5.41 (m, 1H), 6.72-6.88 (m, 3H), 7.07-7.10 (m, 1H), 7.50-7.52 (m, 1H), 10.60-10.80 (m, 1H). |
| Compound 166 | Mp. 262° C. (dec.). MS (EI): m/z 372 [M⁺ + 1]. ¹H-NMR (DMSO-d₆) δ: 2.29-2.81 (m, 11H), 4.53 (s, 2H), 4.77 (d, J = 15.7 Hz, 1H), 5.37 (d, J = 15.7 Hz, 1H), 6.57-6.58 (m, 1H), 6.75-6.78 (m, 2H), 7.02-7.05 (m, 1H), 7.42-7.44 (m, 1H). |
| Compound 167 | MS (EI): m/z 412 [M⁺ + 1]. ¹H-NMR (DMSO-d₆) δ: 2.17-2.23 (m, 3H), 2.68-3.65 (m, 11H), 4.32-4.46 (m, 2H), 4.85-4.88 (m, 1H), 5.42-5.45 (m, 1H), 6.84-7.51 (m, 5H), 10.27-10.38 (m, 2H). |
| Compound 168 | Mp. 183° C. (dec.). MS (EI): m/z 398 [M⁺ + 1]. ¹H-NMR (DMSO-d₆) δ: 2.09 (s, 3H), 2.28-2.74 (m, 8H), 3.19 (s, 2H), 3.47-3.54 (m, 2H), 4.82 (d, J = 15.4 Hz, 1H), 5.41 (d, J = 15.4 Hz, 1H), 6.78-6.80 (m, 1H), 6.98-7.03 (m, 2H), 7.10-7.12 (m, 1H), 7.41-7.43 (m, 1H). |
| Compound 169 | Mp. 183°-187° C. ¹H-NMR (DMSO-d₆) δ: 1.17-1.90 (m, 5H), 2.22-3.73 (m, 17H), 4.83-4.88 (m, 1H), 5.40-5.46 (m, 1H), 6.82-7.50 (m, 5H), 10.33-10.50 (m, 1H). |

TABLE 14-continued

| Compound No. | Properties |
|---|---|
| Compound 170 | Mp. 108° C. (dec.). MS (EI): m/z 425 [M+]. 1H-NMR (DMSO-d6) δ: 1.61-1.64 (m, 2H), 2.09 (s, 3H), 2.23-2.70 (m, 14H), 3.50-3.51 (m, 2H), 4.82 (d, J = 15.4 Hz, 1H), 5.40 (d, J = 15.4 Hz, 1H), 6.78-6.79 (m, 1H), 6.98-7.03 (m, 2H), 7.10-7.13 (m, 1H), 7.41-7.42 (m, 1H). |
| Compound 171 | Mp. 210°-212° C. 1H-NMR (DMSO-d6) δ: 2.36-3.60 (m, 11H), 3.60 (s, 3H), 3.81-3.93 (m, 2H), 4.87 (d, J = 15.3 Hz, 1H), 5.45 (d, J = 15.3 Hz, 1H), 6.85-7.53 (m, 5H), 10.67 (brs, 1H). |
| Compound 172 | Mp. 143°-146° C. 1H-NMR (DMSO-d6) δ: 2.09-2.70 (m, 11H), 3.64-3.73 (m, 2H), 4.83 (d, J = 14.9 Hz, 1H), 5.41 (d, J = 14.9 Hz, 1H), 6.81-7.44 (m, 5H). |
| Compound 173 | Mp. 216° C. (dec.). 1H-NMR (DMSO-d6) δ: 1.18 (m, 3H), 2.25-3.75 (m, 17H), 4.07-4.15 (m, 2H), 4.83-4.88 (m, 1H), 5.40-5.46 (m, 1H), 6.85-7.51 (m, 5H), 10.70-10.95 (m, 1H). |
| Compound 174 | MS (EI): m/z 441 [M+ + 1]. 1H-NMR (DMSO-d6) δ: 2.28-2.73 (m, 10H), 3.06-3.11 (m, 2H), 3.59-3.67 (m, 5H), 4.83 (d, J = 15.4 Hz, 1H), 5.41 (d, J = 15.4 Hz, 1H), 5.46 (s, 2H), 5.82 (s, 1H), 6.78-6.80 (m, 1H), 7.00-7.14 (m, 3H), 7.42-7.43 (m, 1H) |
| Compound 175 | Mp. 161°-164° C. MS (EI): m/z 429 [M+ + 2]. 1H-NMR (DMSO-d6) δ: 2.28-3.52 (m, 14H), 4.82 (d, J = 15.4 Hz, 1H), 5.41 (d, J = 15.4 Hz, 1H), 5.47 (s, 2H), 5.84 (s, 1H), 6.78-6.79 (m, 1H), 6.99-7.13 (m, 3H), 7.41-7.43 (m, 1H), 12.26 (br, 1H). |
| Compound 176 | Mp. 116° C. (dec.). MS (EI): m/z 509 [M+]. 1H-NMR (DMSO-d6) δ: 1.24-1.81 (m, 12H), 2.68-2.88 (m, 8H), 3.34-3.41 (m, 8H), 4.53-4.57 (m, 1H), 6.77-7.57 (m, 6H), 10.91 (brs, 1H). |

TABLE 15

| Compound No. | Properties |
|---|---|
| Compound 177 | MS (EI): m/z 477 [M+ + 1]. 1H-NMR (DMSO-d6) δ: 2.41-3.81 (m, 20H), 4.83-4.89 (m, 1H), 5.40-5.46 (m, 1H), 6.83-6.86 (m, 1H), 7.06-7.18 (m, 3H), 7.50-7.52 (m, 2H), 10.50-10.67 (m, 1H). |
| Compound 178 | Mp. 163°-165° C. MS (EI): m/z 462 [M+ + 1]. 1H-NMR (DMSO-d6) δ: 2.28-3.55 (m, 17H), 4.82 (d, J = 15.3 Hz, 1H), 5.41 (d, J = 15.3 Hz, 1H), 6.78-6.80 (m, 1H), 6.87 (s, 1H), 6.99-7.03 (m, 2H), 7.11-7.13 (m, 1H), 7.41-7.43 (m, 1H). |
| Compound 179 | Mp. 149° C. (dec.). 1H-NMR (DMSO-d6) δ: 1.41 (s, 9H), 2.24-3.53 (m, 10H), 4.82-5.43 (m, 2H), 6.80-7.45 (m, 5H), 12.36 (brs, 1H). |
| Compound 180 | 1H-NMR (DMSO-d6) δ: 1.24-1.79 (m, 13H), 2.49-3.21 (m, 8H), 3.69-3.75 (m, 2H), 4.83-5.46 (m, 2H), 6.62-7.50 (m, 6H), 9.28 (brs, 1H), 9.54 (brs, 1H). |
| Compound 181 | Mp. 237° C. (dec.). 1H-NMR (DMSO-d6) δ: 1.10-1.28 (m, 6H), 2.41-3.80 (m, 18H), 4.23-4.27 (m, 2H), 7.06-7.10 (m, 1H), 7.21-7.35 (m, 3H), 7.47-7.50 (m, 1H), 10.58-10.59 (m, 1H). |
| Compound 182 | Mp. >280° C. MS (EI): m/z 397 [M+]. 1H-NMR (DMSO-d6) δ: 1.13 (t, J = 6.7 Hz, 3H), 2.39-3.72 (m, 18H), 7.07-7.09 (m, 1H), 7.19-7.26 (m, 2H), 7.32-7.34 (m, 1H), 7.42 (s, 1H). |
| Compound 183 | Mp. 126° C. (dec.). 1H-NMR (DMSO-d6) δ: 1.38-1.78 (m, 6H), 2.50-3.62 (m, 19H), 4.85 (d, J = 15.2 Hz, 1H), 5.44 (d, J = 15.2 Hz, 1H), 6.84-7.51 (m, 5H), 10.35-10.67 (m, 1H), 10.99-11.20 (m, 1H). |
| Compound 184 | Mp. 131° C. (dec.). 1H-NMR (DMSO-d6) δ: 1.77-1.81 (m, 2H), 2.28-3.93 (m, 20H), 4.80-4.96 (m, 2H), 5.38-5.54 (m, 2H), 6.80-7.11 (m, 4H), 7.48-7.50 (m, 1H), 9.75-9.89 (m, 1H). |
| Compound 185 | Mp. 130°-133° C. MS (EI): m/z 443 [M+]. 1H-NMR (DMSO-d6) δ: 1.74-1.75 (m, 2H), 2.17-2.70 (m, 17H), 3.61-6.62 (m, 1H), 4.30-4.38 (m, 1H), 4.81 (d, J = 15.4 Hz, 1H), 5.39 (d, J = 15.4 Hz, 1H), 6.77-6.78 (m, 1H), 6.90-7.07 (m, 3H), 7.40-7.41 (m, 1H). |
| Compound 186 | Mp. 124° C. (dec.). MS (EI): m/z 467 [M+ − 1]. 1H-NMR (DMSO-d6) δ: 1.37-1.47 (m, 6H), 2.27-2.70 (m, 20H), 4.79 (d, J = 15.4 Hz, 1H), 5.39 (d, J = 15.4 Hz, 1H), 6.77-7.09 (m, 4H), 7.41-7.42 (m, 1H). |
| Compound 187 | Mp. 152°-154° C. 1H-NMR (DMSO-d6) δ: 1.77-1.84 (m, 4H), 2.08-2.12 (m, 3H), 2.27-2.31 (m, 2H), 2.46-3.70 (m, 17H), 4.81-4.86 (m, 1H), 5.83-5.44 (m, 1H), 6.81-6.84 (m, 1H), 6.96-7.11 (m, 3H), 7.48-7.50 (m, 1H), 10.45-10.62 (m, 1H). |
| Compound 188 | MS (EI): m/z 453 [M+]. 1H-NMR (DMSO-d6) δ: 1.62-1.65 (m, 2H), 1.74-1.76 (m, 2H), 2.09 (s, 3H), 2.17-2.70 (m, 16H), 4.80 (d, J = 15.4 Hz, 1H), 5.39 (d, J = 15.4 Hz, 1H), 6.77-6.78 (m, 1H), 6.90-7.07 (m, 3H), 7.41-7.45 (m, 1H), 11.95-12.05 (br, 1H). |

TABLE 16

| Compound No. | Properties |
| --- | --- |
| Compound 189 | Mp. 242° C. (dec.). $^1$H-NMR (DMSO-$d_6$) δ: 1.38-1.42 (m, 6H), 2.43-3.56 (m, 14H), 4.93-4.96 (m, 1H), 5.48-5.51 (m, 1H), 6.91-7.52 (m, 5H), 10.72 (brs, 1H). |
| Compound 190 | Mp. 182°-185° C. $^1$H-NMR (DMSO-$d_6$) δ: 1.35-1.39 (m, 6H), 2.37-3.55 (m, 11H), 4.92 (d, J = 14.8 Hz, 1H), 5.48 (d, J = 14.8 Hz, 1H), 6.90-7.52 (m, 5H), 10.88 (br, 1H), 12.59 (br, 1H). |
| Compound 191 | Mp. 162° C. (dec.). $^1$H-NMR (DMSO-$d_6$) δ: 2.06-3.79 (m, 20H), 4.83-4.88 (m, 1H), 5.40-5.46 (m, 1H), 6.82-6.86 (m, 1H), 7.05-7.18 (m, 3H), 7.50-7.52 (m, 1H), 10.17-10.48 (m, 1H). |
| Compound 192 | Mp. 166° C. (dec.). MS (EI): m/z 411 [M$^+$]. $^1$H-NMR (DMSO-$d_6$) δ: 2.09-3.50 (m, 17H), 4.82 (d, J = 15.4 Hz, 1H), 5.40 (d, J = 15.4 Hz, 1H), 6.78-6.79 (m, 1H), 6.98-7.12 (m, 3H), 7.41-7.42 (m, 1H). |
| Compound 193 | Mp. 113°-115° C. $^1$H-NMR (DMSO-$d_6$) δ: 1.79-1.99 (m, 2H), 2.36-3.66 (m, 22H), 4.83-4.89 (m, 1H), 5.40-5.46 (m, 1H), 6.83-6.86 (m, 1H), 7.05-7.20 (m, 4H), 7.50-7.52 (m, 1H), 10.06-10.43 (m, 1H). |
| Compound 194 | Mp. 181°-183° C. $^1$H-NMR (DMSO-$d_6$) δ: 1.60-1.64 (m, 2H), 2.22-3.11 (m, 15H), 3.48-3.55 (m, 2H), 4.82 (d, J = 15.4 Hz, 1H), 5.41 (d, J = 15.4 Hz, 1H), 6.787-6.79 (m, 1H), 6.99-7.03 (m, 3H), 7.11-7.13 (m, 1H), 7.41-7.43 (m, 1H). |
| Compound 195 | Mp. 102°-105° C. $^1$H-NMR (DMSO-$d_6$) δ: 2.36-3.57 (m, 22H), 4.80-4.86 (m, 1H), 5.40-5.44 (m, 1H), 6.81-6.84 (m, 1H), 7.01-7.15 (m, 3H), 7.37-7.51 (m, 2H), 9.88-10.51 (m, 1H). |
| Compound 196 | Mp. 121° C. (dec.). MS (EI): m/z 477 [M$^+$ + 1]. $^1$H-NMR (DMSO-$d_6$) δ: 2.27-3.39 (m, 19H), 4.79 (d, J = 15.4 Hz, 1H), 5.38 (d, J = 15.41 Hz, 1H), 6.76-6.77 (m, 1H), 6.89-7.09 (m, 4H), 7.40-7.42 (m, 1H). |
| Compound 197 | Mp. 208°-210° C. $^1$H-NMR (DMSO-$d_6$) δ: 2.46-2.69 (m, 2H), 2.91-3.09 (m, 4H), 3.21-3.27 (m, 2H), 3.60 (s, 3H), 3.82 (d, J = 15.7 Hz, 1H), 3.91 (d, J = 15.7 Hz, 1H), 4.86 (d, J = 15.3 Hz, 1H), 5.45 (d, J = 15.3 Hz, 1H), 6.85-7.51 (m, 5H), 9.12-9.30 (m, 2H). |
| Compound 198 | Mp. 221° C. (dec.). $^1$H-NMR (DMSO-$d_6$) δ: 1.93-3.66 (m, 22H), 4.83-4.89 (m, 1H), 5.40-5.46 (m, 1H), 6.83-6.86 (m, 1H), 7.05-7.20 (m, 3H), 7.50-7.52 (m, 1H), 10.14-10.32 (m, 1H). |
| Compound 199 | Mp. 127° C. (dec.). MS (EI): m/z 429 [M$^+$]. $^1$H-NMR (DMSO-$d_6$) δ: 1.67-1.71 (m, 2H), 2.03 (s, 3H), 2.22-2.70 (m, 14H), 3.48-3.55 (m, 2H), 4.82 (d, J = 15.4 Hz, 1H), 5.41 (d, J = 15.4 Hz, 1H), 6.78-6.79 (m, 1H), 6.98-7.13 (m, 3H), 7.41-7.42 (m, 1H). |
| Compound 200 | Mp. 257° C. (dec.). $^1$H-NMR (DMSO-$d_6$) δ: 2.10-2.16 (m, 3H), 2.36-3.74 (m, 17H), 4.83-4.89 (m, 1H), 5.40-5.46 (m, 1H), 6.83-6.86 (m, 1H), 7.06-7.19 (m, 3H), 7.50-7.42 (m, 1H), 10.42-10.61 (m, 1H). |

TABLE 17

| Compound No. | Properties |
| --- | --- |
| Compound 201 | Mp. 204°-206° C. $^1$H-NMR (DMSO-$d_6$) δ: 2.07 (s, 3H), 2.28-2.70 (m, 12H), 3.51-3.55 (m, 2H), 4.82 (d, J = 15.4 Hz, 1H), 5.41 (d, J = 15.4 Hz, 1H), 6.78-6.79 (m, 1H), 6.99-7.13 (m, 3H), 7.41-7.43 (m, 1H). |
| Compound 202 | Mp. 193° C. (dec.). $^1$H-NMR (DMSO-$d_6$) δ: 0.90 (m, 3H), 1.35-1.39 (m, 6H), 1.66 (m, 2H), 2.50-3.39 (m, 10H), 4.92 (d, J = 15.0 Hz, 1H), 5.47 (d, J = 15.0 Hz, 1H), 6.89-7.51 (m, 5H), 10.45 (m, 1H), 12.51 (m, 1H). |
| Compound 203 | Mp. 279° C. (dec.). $^1$H-NMR (DMSO-$d_6$) δ: 2.19-3.22 (m, 13H), 6.02 (d, J = 15.6 Hz, 1H), 7.04-7.32 (m, 5H), 7.52 (d, J = 15.6 Hz, 1H). |
| Compound 204 | Mp. 265° C. (dec.). MS (EI): m/z 373 [M$^+$]. $^1$H-NMR (DMSO-$d_6$) δ: 2.13-2.79 (m, 11H), 3.69 (s, 2H), 4.75 (d, J = 15.6 Hz, 1H), 5.34 (d, J = 15.6 Hz, 1H), 6.57 (s, 1H), 6.89-7.16 (m, 3H). |
| Compound 205 | Mp. 248° C. (dec.). MS (EI): m/z 389 [M$^+$]. $^1$H-NMR (DMSO-$d_6$) δ: 2.13-2.79 (m, 11H), 3.70 (s, 2H), 4.78 (d, J = 15.6 Hz, 1H), 5.36 (d, J = 15.6 Hz, 1H), 6.60 (s, 1H), 7.09-7.31 (m, 3H). |
| Compound 206 | Mp. 245° C. (dec.). MS (EI): m/z 417 [M$^+$]. $^1$H-NMR (DMSO-$d_6$) δ: 1.06-1.48 (m, 6H), 2.12-3.38 (m, 11H), 4.74-4.79 (m, 1H), 5.33-5.38 (m, 1H), 6.52-6.65 (m, 1H), 7.08-7.13 (m, 2H), 7.28-7.31 (m, 1H). |
| Compound 207 | Mp. 260°-262° C. MS (EI): m/z 385 [M$^+$]. $^1$H-NMR (DMSO-$d_6$) δ: 2.19-2.97 (m, 11H), 3.60-3.81 (m, 5H), 4.69 (d, J = 15.6 Hz, 1H), 5.29 (d, J = 15.6 Hz, 1H), 6.54-6.59 (m, 2H), 6.79-6.80 (m, 1H), 7.03-7.05 (m, 1H). |
| Compound 208 | Mp. 274°-275° C. $^1$H-NMR (DMSO-$d_6$) δ: 2.20-2.79 (m, 14H), 3.67 (s, 2H), 4.70 (d, J = 15.6 Hz, 1H), 5.32 (d, J = 15.6 Hz, 1H), 6.56 (s, 1H), 6.85 (s, 1H), 6.97-7.05 (m, 2H). |
| Compound 209 | Mp. 244° C. (dec.). $^1$H-NMR (DMSO-$d_6$) δ: 1.92-2.99 (m, 12H), 6.69 (s, 1H), 6.83 (d, J = 11.5 Hz, 1H), 6.88 (d, J = 11.5 Hz, 1H), 7.10-7.39 (m, 4H). |

TABLE 17-continued

| Compound No. | Properties |
|---|---|
| Compound 210 | Mp. >280° C. $^1$H-NMR (DMSO-$d_6$) δ: 1.92-2.86 (m, 13H), 6.84 (d, J = 11.5 Hz, 1H), 6.97 (d, J = 11.5 Hz, 1H), 7.10-7.40 (m, 5H). |
| Compound 211 | Mp. 245° C. (dec.). $^1$H-NMR (DMSO-$d_6$) δ: 2.18-3.26 (m, 13H), 6.73-6.75 (m, 1H), 7.34-7.35 (m, 2H), 7.54 (s, 1H), 7.73-7.75 (m, 1H). |
| Compound 212 | Mp. 141°-142° C. MS (EI): m/z 375 [M$^+$ + 2], 373 [M$^+$]. $^1$H-NMR (DMSO-$d_6$) δ: 1.90-2.79 (m, 13H), 3.18-3.22 (m, 2H), 6.85 (s, 1H), 6.98-7.30 (m, 4H). |

Example 38

In Vitro Human Histamine H1 Receptor Binding Experiment

Recombinant human histamine H1 receptor plasmid (prepared by Invitrogen) was transfected to HEK293A cells with Lipofectamine 2000 (manufactured by Invitrogen). Cells stably expressing human histamine H1 receptor were screened with Geneticin (manufactured by Invitrogen). The cells were continued to be cultured using a Dulbecco's Modified Eagle Medium containing 10% fetal bovine serum, 0.1 mmol/L MEM Non-Essential Amino Acids Solution, 2 mmol/L L-glutamine and 0.7 mg/mL Geneticin in a 5% $CO_2$ incubator at 37° C. The cells stably expressing human histamine H1 receptor were prepared using 50 mmol/L Tris-HCl (pH 7.5) (hereinafter referred to as buffer) containing 0.1% bovine serum albumin, so as to have a concentration of 3×10$^6$ cells/mL, to give a cell sample preparation. Fifty microliters of the buffer, 50 μl of a test substance solution at various concentrations, and 50 μL of [$^3$H]pyrilamine solution (final concentration: 3 nmol/L) were added to each of the wells on the 96-well plate, and stirred, and 100 μL of the cell sample preparation was then added thereto (at a concentration of 3×10$^5$ cells/well) to initiate the reaction.

The cells were incubated at room temperature for 60 minutes, and then filtered on UniFilter GF/C plate (manufactured by Packard) immersed in 0.5% polyethyleneimine using a cell harvester (IH-110, manufactured by INNOTECH CORPORATION), to stop the reaction, and the plate was washed with the buffer. The plate after washing was sufficiently dried, and 20 μL of a scintillator (MaxiLight, manufactured by Hidex) was added thereto, and count per minute (cpm) was measured with a multi-labeled microplate reader (Plate Chameleo II, manufactured by Hidex). The nonspecific binding was cpm in a case where 30 μmol/L pyrilamine was added. The experiments were carried out at n=3, and at least repeated 3 times.

One example of the results are shown in Table 18. The compounds of the present invention showed very high potent activity in in vitro human histamine H1 receptor binding experiment.

TABLE 18

| Compound No. | IC$_{50}$ (nmol/L) |
|---|---|
| Compound 10 | 88.5 |
| Compound 15 | 26.8 |
| Compound 20 | 15.2 |
| Compound 23 | 3.5 |
| Compound 27 | 52.8 |
| Compound 31 | 16.4 |
| Compound 38 | 70.8 |
| Compound 40 | 52.1 |
| Compound 44 | 19.2 |
| Compound 47 | 29.3 |
| Compound 49 | 32.5 |
| Compound 50 | 16.9 |
| Compound 57 | 70.1 |
| Compound 58 | 69.3 |
| Compound 60 | 59.1 |
| Compound 63 | 42.0 |
| Compound 64 | 48.6 |
| Compound 70 | 93.3 |
| Compound 71 | 62.0 |
| Compound 74 | 70.9 |
| Compound 75 | 74.8 |
| Compound 77 | 37.8 |
| Compound 78 | 65.1 |
| Compound 79 | 28.2 |
| Compound 80 | 69.9 |
| Compound 84 | 38.4 |
| Compound 85 | 27.5 |
| Compound 86 | 21.2 |
| Compound 94 | 69.0 |
| Compound 95 | 14.9 |
| Compound 97 | 16.9 |
| Compound 103 | 35.4 |
| Compound 104 | 4.8 |
| Compound 105 | 50.2 |
| Compound 106 | 7.04 |
| Compound 110 | 23.4 |
| Compound 112 | 1.94 |
| Compound 115 | 16.6 |
| Compound 116 | 3.95 |
| Compound 118 | 23.6 |
| Compound 121 | 94.7 |
| Compound 122 | 13.4 |
| Compound 123 | 3.12 |
| Compound 124 | 46.7 |
| Compound 127 | 8.20 |
| Compound 129 | 22.7 |
| Compound 130 | 78.4 |
| Compound 131 | 32.3 |
| Compound 133 | 17.0 |
| Compound 138 | 26.0 |
| Compound 140 | 10.1 |
| Compound 141 | 6.77 |
| Compound 142 | 90.9 |
| Compound 145 | 68.6 |
| Compound 147 | 4.04 |
| Compound 151 | 93.6 |
| Compound 154 | 25.6 |
| Compound 156 | 9.66 |
| Compound 157 | 90.5 |
| Compound 158 | 47.0 |
| Compound 160 | 5.58 |
| Compound 163 | 90.8 |
| Compound 165 | 11.8 |
| Compound 169 | 8.32 |
| Compound 171 | 4.16 |
| Compound 172 | 22.2 |
| Compound 173 | 1.26 |
| Compound 174 | 11.0 |
| Compound 176 | 72.7 |
| Compound 177 | 7.12 |
| Compound 181 | 13.0 |

TABLE 18-continued

| Compound No. | IC$_{50}$ (nmol/L) |
| --- | --- |
| Compound 187 | 8.76 |
| Compound 191 | 4.72 |
| Compound 193 | 13.1 |
| Compound 195 | 11.7 |
| Compound 197 | 80.9 |
| Compound 198 | 0.59 |
| Compound 200 | 7.83 |

Example 39

Rat Histamine-Induced Vascular Hyperpermeability Reaction

In Vivo Antihistamine Action

An SD male rat (SPF) of 180 g in weight was previously fed for one week or more by allowing the rat to take a solid feed and tap water ad libitum, under the environment setting of a temperature of 22° C., humidity of 55% and an artificial illumination of 12 hours a day (light phase 8 am to 8 pm), and the rat was fasted overnight to be used for the experiment. Histamine•dihydrochloride (hereinafter referred to as histamine) and Evans Blue were used by dissolving each in physiological saline upon use. A substance to be tested was dissolved in water for injection or suspended in 0.5% carboxymethyl cellulose sodium, and the rat was orally administered with the solution or suspension (dose volume: 5 mL/kg body weight). After 1 hour from the administration, the physiological saline and the histamine solution were each intracutaneously injected to two locations (20 µg/0.05 ml/location) each on a back part of the rat of which hair was sheared with an electric clipper while anesthetizing with an ether. A 0.5% Evans Blue-containing physiological saline was injected intravenously to the tail of the rat (1 mL/200 g body weight) immediately before the intracutaneous injection of the histamine.

After 30 minutes, the animal was decapitated, and allowed to bleed lethally, and the skin was removed to measure an amount of leaked pigment in the blue-stained portion. The measurement of the amount of leaked pigment was carried out as follows. Skins of the pigment leaking site were cut out at two locations, 1 mL of a 2 mol/L aqueous potassium hydroxide solution was added thereto in a test tube, and the test tube was allowed to stand overnight at 37° C. to dissolve. Thereafter, 6 mL of a 1:3 mixed solution of 0.67 mol/L phosphoric acid and acetone was added to the solution, and the mixture was vigorously shaken for 10 minutes. Thereafter, the mixture was filtered, and the absorbance of the filtrate at 620 nm was measured. The absorbance obtained from the two locations of the sites injected with physiological saline, as blank value, was used for a compensation. The amount of leaked pigment was calculated from the calibration curve of Evans Blue at 620 nm.

One example of the results is shown in Table 19. The compound of the present invention showed a very potent antagonistic activity in the rat histamine-induced vascular hyperpermeability reaction.

TABLE 19

| Compound No. | ED$_{50}$ (mg/kg) |
| --- | --- |
| Compound 4 | 0.69 |
| Compound 15 | 0.18 |
| Compound 26 | 0.059 |
| Compound 27 | 1.63 |
| Compound 35 | 0.28 |
| Compound 48 | 0.68 |
| Compound 49 | Ca. 1 |
| Compound 54 | 0.027 |
| Compound 58 | 0.78 |
| Compound 65 | 0.14 |
| Compound 68 | 0.13 |
| Compound 108 | 1.16 |
| Compound 113 | 0.072 |
| Compound 117 | 0.027 |
| Compound 118 | 0.48 |
| Compound 119 | 1.10 |
| Compound 124 | 0.009 |
| Compound 126 | 0.446 |
| Compound 127 | Ca. 0.1 |
| Compound 128 | Ca. 0.1 |
| Compound 129 | 0.088 |
| Compound 130 | 0.044 |
| Compound 131 | Ca. 0.1 |
| Compound 132 | 0.17 |
| Compound 135 | 2.33 |
| Compound 137 | 0.24 |
| Compound 138 | 0.47 |
| Compound 139 | 2.24 |
| Compound 140 | Ca. 0.01 |
| Compound 142 | Ca. 0.3 |
| Compound 145 | 0.29 |
| Compound 151 | <0.1 |
| Compound 152 | 1.49 |
| Compound 153 | 2.61 |
| Compound 155 | 0.334 |
| Compound 165 | 0.107 |
| Compound 167 | 0.194 |
| Compound 168 | 0.264 |
| Compound 169 | 0.241 |
| Compound 170 | 0.614 |
| Compound 171 | 0.073 |
| Compound 172 | 0.117 |
| Compound 173 | 1.430 |
| Compound 177 | 0.302 |
| Compound 180 | 1.55 |
| Compound 188 | Ca. 0.3 |
| Compound 190 | 0.419 |
| Compound 191 | 0.597 |
| Compound 192 | 0.312 |
| Compound 197 | 0.190 |
| Compound 198 | Ca. 0.3 |
| Compound 199 | Ca. 0.01 |
| Compound 200 | Ca. 0.3 |
| Compound 209 | 0.42 |
| Ketotifen | 0.54 |

Example 40

Murine Cerebral H1 Receptor Occupying Content (Ex Vivo)

A 6-week-old ICR male mouse was previously fed for one week or more by allowing the mouse to take a solid feed and tap water ad libitum, under the environment setting of a temperature of 22° C., humidity of 55% and an artificial illumination of 12 hours a day, and the mouse was fasted overnight to be used for the experiment. A substance to be tested was dissolved with water for injection or suspended in 0.5% carboxymethyl cellulose solution, and the solution or suspension was orally administered to the mouse (dose volume: 0.1 mL/10 g body weight). After 1 hour from the oral administration, the mouse was decapitated, and the entire brain, except for cerebellum and medulla oblongatae, was rapidly excised. The excised brain tissue was homogenized with Polytron (manufactured by Kinematica) in an ice-cooled 50 mmol/L phosphate buffered saline (pH 7.4, 100 mg/1.9 mL).

To a test tube for reaction (TPX-Tube) were added 180 μL of the brain homogenate, and 10 μL of $^3$H-pyrilamine solution (final concentration: 2 nmol/L) and 10 μL of a non-labeled pyrilamine solution (final concentration: 200 μmol/L) or a 50 mmol/L phosphate buffered saline, and the mixture was incubated at room temperature for 45 minutes, and 2.0 mL of an ice-cooled, 50 mmol/L phosphate buffered saline was then added thereto to stop the reaction. The reaction mixture was filtered with a GF/B filter (manufactured by ADVANTEC), and the filtrate was placed in a vial and dried overnight at 60 degrees. After drying, 10 mL of a scintillator (AL-1, toluene-based, manufactured by DOJINDO LABORATORIES) was added to the product, and the disintegration per minute (dpm) was measured with a liquid scintillation counter (manufactured by Packard, U.S.A., TRI-CARB 2700TR) (5 minutes/vial).

One example of the results is shown in Table 20. In this experiment, the compound of the present invention require a high concentration for occupying the receptor in the brain, showing that the brain transfer is low. It was evident from the results that the compounds of the present invention show peripheral-selective anti-histamine action without undergoing brain transfer, so that the compounds can alleviate side effects on the central nervous system, such as drowsiness.

TABLE 20

| Compound No. | $ID_{50}$ (mg/kg) |
|---|---|
| Compound 4 | 43.1 |
| Compound 15 | 5.6 |
| Compound 26 | 4.8 |
| Compound 27 | 55.1 |
| Compound 35 | 28.4 |
| Compound 48 | 95.5 |
| Compound 49 | 33.9 |
| Compound 54 | 9.3 |
| Compound 58 | 205.2 |
| Compound 65 | 19.5 |
| Compound 68 | 14.6 |
| Compound 108 | 110.5 |
| Compound 113 | 98.7 |
| Compound 117 | 4.2 |
| Compound 118 | 24.3 |
| Compound 119 | 74.5 |
| Compound 124 | 3.2 |
| Compound 126 | 236.7 |
| Compound 127 | 9.84 |
| Compound 128 | 7.45 |
| Compound 129 | 40.5 |
| Compound 130 | 8.0 |
| Compound 131 | 9.20 |
| Compound 132 | 37.5 |
| Compound 135 | >200 |
| Compound 137 | >200 |
| Compound 138 | 65.4 |
| Compound 139 | >200 |
| Compound 140 | 3.50 |
| Compound 142 | 11.9 |
| Compound 145 | >200 |
| Compound 151 | 6.36 |
| Compound 152 | 199.34 |
| Compound 153 | >200 |
| Compound 155 | 66.6 |
| Compound 165 | 23.0 |
| Compound 167 | 35.1 |
| Compound 168 | 10.4 |
| Compound 169 | 12.5 |
| Compound 170 | 70.3 |
| Compound 171 | 29.6 |
| Compound 172 | 28.0 |
| Compound 173 | 87.1 |

TABLE 20-continued

| Compound No. | $ID_{50}$ (mg/kg) |
|---|---|
| Compound 177 | 124.6 |
| Compound 180 | >200 |
| Compound 188 | 23.0 |
| Compound 190 | 73.2 |
| Compound 191 | 79.2 |
| Compound 192 | 63.8 |
| Compound 197 | >200 |
| Compound 198 | 22.1 |
| Compound 199 | 4.5 |
| Compound 200 | 53.4 |
| Compound 209 | >200 |
| Ketotifen | 0.51 |

From the results of Examples 39 and 40 mentioned above, the values obtained by dividing the $ID_{50}$ (Table 20) of the cerebral receptor binding test by the $ED_{50}$ (Table 19) of the histamine-induced vascular hyperpermeability reaction test are shown in Table 21. The larger the $ID_{50}$ (Table 20) of the cerebral receptor binding test, the lower the brain transfer, i.e. the smaller the side effects on the central nervous system, such as drowsiness; and the smaller the $ED_{50}$ (Table 19) of the histamine-induced vascular hyperpermeability reaction test, the more potent the antihistamine action. Therefore, the value calculated by $ID_{50} \div ED_{50}$ can serve as an index showing that the larger the calculated value, the more potent the antihistamine action and the smaller the side effects on the central nervous system, such as drowsiness. As shown in Table 21, the compound of the present invention shows a large value for a value calculated by $ID_{50} \div ED_{50}$, as compared to an already existing antihistamine Ketotifen. Therefore, it can be said that the compound of the present invention has desired properties as a pharmaceutical composition, especially as an active ingredient for antihistamine, that has a potent antihistamine action and smaller side effects on the central nervous system, such as drowsiness.

TABLE 21

| Compound No. | $ID_{50}$ (mg/kg)/ $ED_{50}$ (mg/kg) |
|---|---|
| Compound 4 | 62.5 |
| Compound 15 | 31.1 |
| Compound 26 | 81.4 |
| Compound 27 | 33.8 |
| Compound 35 | 101.4 |
| Compound 48 | 140.4 |
| Compound 49 | 33.9 |
| Compound 54 | 344.4 |
| Compound 58 | 263.1 |
| Compound 65 | 139.3 |
| Compound 68 | 112.3 |
| Compound 108 | 95.3 |
| Compound 113 | 1370.8 |
| Compound 117 | 155.6 |
| Compound 118 | 50.6 |
| Compound 119 | 67.7 |
| Compound 124 | 355.6 |
| Compound 126 | 530.7 |
| Compound 127 | 98.4 |
| Compound 128 | 74.5 |
| Compound 129 | 460.2 |
| Compound 130 | 181.8 |
| Compound 131 | 92.0 |
| Compound 132 | 220.6 |
| Compound 135 | >85.8 |

TABLE 21-continued

| Compound No. | ID$_{50}$ (mg/kg)/ ED$_{50}$ (mg/kg) |
|---|---|
| Compound 137 | >833.3 |
| Compound 138 | 139.1 |
| Compound 139 | >89.3 |
| Compound 140 | 350.0 |
| Compound 142 | 39.7 |
| Compound 145 | >689.7 |
| Compound 151 | >63.6 |
| Compound 152 | 133.8 |
| Compound 153 | >76.6 |
| Compound 155 | 199.4 |
| Compound 165 | 215.0 |
| Compound 167 | 180.9 |
| Compound 168 | 39.4 |
| Compound 169 | 51.9 |
| Compound 170 | 114.5 |
| Compound 171 | 405.5 |
| Compound 172 | 239.3 |
| Compound 173 | 60.9 |
| Compound 177 | 412.6 |
| Compound 180 | >129.0 |
| Compound 188 | 76.7 |
| Compound 190 | 174.7 |
| Compound 191 | 132.7 |
| Compound 192 | 204.5 |
| Compound 197 | >1052.6 |
| Compound 198 | 73.7 |
| Compound 199 | 450.0 |
| Compound 200 | 178.0 |
| Compound 209 | >476.2 |
| Ketotifen | 0.9 |

INDUSTRIAL APPLICABILITY

The piperidine derivative of the present invention had a potent histamine H1 receptor binding ability as shown in Table 18, and showed a potent histamine receptor antagonistic activity in the rat histamine-induced vascular hyperpermeability reaction, as shown in Table 19. Further, as is clear from Table 20, the piperidine derivative shows a low brain transfer even in a cerebral receptor binding test where a mouse is orally administered, so that the piperidine derivative of the present invention is preferable from the aspect of alleviating side effects on the central nervous system, such as drowsiness. As is clear from the values of Table 21 for together evaluating both of these histamine receptor antagonistic activity and brain transfer, the piperidine derivative of the present invention is a potent histamine receptor antagonistic substance, and has smaller side effects on the central nervous system, such as drowsiness; therefore, the piperidine derivative has properties suitable for an active ingredient of a pharmaceutical composition, such as a desired antihistamine, so that the piperidine derivative is highly useful.

The invention claimed is:
1. A piperidine derivative, or salt or hydrate thereof that is pharmaceutically acceptable, wherein the piperidine derivative is represented by the following general formula (I):

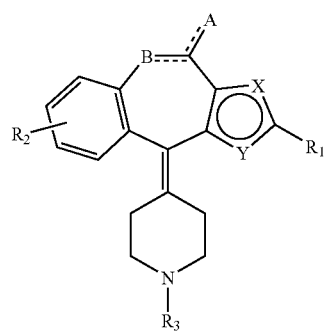

(1)

wherein R$_1$ stands for a hydrogen or a substituent selected from the following (a) to (i):
(a) a cyano,
(b) acrylic acid, an alkyl ester of acrylic acid, or a hydroxyalkylamide of acrylic acid,
(c) a ureido,
(d) an alkenyl,
(e) an aminoalkyl which may be substituted with an alkylcarbonyl or an aminocarbonyl,
(f) a carbonylalkyl substituted with a hydroxy, an alkoxy or a hydroxyalkylamino,
(g) a carbonyl substituted with a hydroxy, a morpholino, an alkoxy, a hydroxyalkylaminoalkoxy or cyclohexyloxycarbonyloxyalkoxy,
(h) a carbonylamino substituted with an alkyl or an alkoxy,
(i) an aminocarbonyl which may be substituted with one or two substituents selected from an amino, a hydroxy, an alkoxy, an alkenyl, and an alkyl (which may be substituted with a halogen, a thiol, a piperidino, an amino, an alkoxy, an alkoxycarbonyl, an aminocarbonyl, or one or two hydroxys);
R$_2$ stands for a hydrogen or a substituent selected from the following (j) to (q):
(j) acrylic acid, an alkylester of acrylic acid, or a hydroxyalkylamide of acrylic acid,
(k) an alkyl substituted with a hydroxy or a piperidino,
(l) a carbonylalkyl substituted with a hydroxy, an alkoxy (which may be substituted with a cyclohexyloxycarbonyloxy), a piperidino, or a hydroxyalkylamino,
(m) a carbonyl substituted with a hydroxy, an alkoxy, or a hydroxyalkylamino,
(n) a carbonylalkoxy substituted with a hydroxy or an alkoxy,
(o) a carbonylalkylsulfanyl substituted with a hydroxy or an alkoxy,
(p) an alkoxy,
(q) a halogen; and
R$_3$ stands for a hydrogen or a substituent selected from the following (r) to (v):
(r) an alkyl which may be substituted with a carboxy, a cyano, a pyrrolidyl, a piperidino, an alkoxy, an alkylsulfanyl, or one or two hydroxys,
(s) a carbonyl substituted with an alkyl or alkoxy,
(t) a carbonylalkoxyalkyl substituted with a hydroxy or an alkoxy, (u) a carbonylalkyl substituted with an alkyl, an alkoxy, or an alkylphenyl, (v) an aminoalkyl substituted with an aminocarbonyl or an alkanesulfonyl, wherein one of the above $R_1$ and $R_2$ stands for a substituent other than a hydrogen, A stands for a hydrogen or an oxo, B stands for a carbon or an oxygen, one of X and Y stands for a carbon and the other is a sulfur, a broken line part stands for a single bond or a double bond, with the proviso that when $R_2$ stands for a halogen or an alkoxy, then A stands for a hydrogen, $R_1$ stands for a substituent other than a hydrogen, and B stands for an oxygen.

2. The piperidine derivative, or salt or hydrate thereof that is pharmaceutically acceptable according to claim 1, wherein A is stands for a hydrogen.

3. The piperidine derivative, or salt or hydrate thereof that is pharmaceutically acceptable according to claim 2, wherein one of $R_1$ and $R_2$ is a carbonylalkyl substituted with a hydroxy, and the other is a hydrogen.

4. The piperidine derivative, or salt or hydrate thereof that is pharmaceutically acceptable according to claim 3, wherein $R_1$ is a carbonylalkyl substituted with a hydroxy.

5. The piperidine derivative, or salt or hydrate thereof that is pharmaceutically acceptable according to claim 3, wherein $R_2$ is a carbonylalkyl substituted with a hydroxy.

6. The piperidine derivative, or salt or hydrate thereof that is pharmaceutically acceptable according to claim 2, wherein B is an oxygen, $R_1$ is a hydrogen, and $R_2$ is a carbonylalkylsulfanyl substituted with a hydroxy.

7. The piperidine derivative, or salt or hydrate thereof that is pharmaceutically acceptable according to claim 4, wherein B is a carbon.

8. The piperidine derivative, or salt or hydrate thereof that is pharmaceutically acceptable according to claim 3, wherein B is an oxygen.

9. The piperidine derivative, or salt or hydrate thereof that is pharmaceutically acceptable according to claim 7, wherein $R_3$ is a hydrogen.

10. The piperidine derivative, or salt or hydrate thereof that is pharmaceutically acceptable according to claim 8, wherein $R_3$ is an unsubstituted alkyl.

11. The piperidine derivative, or salt or hydrate thereof that is pharmaceutically acceptable according to claim 8, wherein $R_3$ is an alkylcarbonylalkyl.

12. The piperidine derivative, or salt or hydrate thereof that is pharmaceutically acceptable according to claim 1, wherein the piperidine derivative represented by the general formula (I) is [4-(1-methylpiperidin-4-ylidene)-4,10-dihydro-9-oxa-3-thiazobenzo[f]azulen-2-yl]acetic acid.

13. The piperidine derivative, or salt or hydrate thereof that is pharmaceutically acceptable according to claim 1, wherein the piperidine derivative represented by the general formula (I) is {4-[1-(4-oxopentyl)piperidin-4-ylidene]-4,10-dihydro-9-oxa-3-thiabenzo[f]azulen-6-yl}acetic acid.

14. The piperidine derivative, or salt or hydrate thereof that is pharmaceutically acceptable according to claim 1, wherein the piperidine derivative represented by the general formula (I) is 2-methyl-2-[4-(1-methylpiperidin-4-ylidene)-4,10-dihydro-9-oxa-3-thiabenzo[f]azulen-6-ylsulfanyl]propionic acid.

15. The piperidine derivative, or salt or hydrate thereof that is pharmaceutically acceptable according to claim 1, wherein the piperidine derivative represented by the general formula (I) is 3-(4-piperidin-4-ylidene-4H-1-thiabenzo[f]azulen-2-yl)propionic acid.

16. A pharmaceutical composition comprising at least one member selected from the piperidine derivatives, or salt or hydrate thereof that is pharmaceutically acceptable as defined in claim 1.

17. An antihistamine comprising at least one member selected from the piperidine derivatives, or salt or hydrate thereof that is pharmaceutically acceptable as defined in claim 1.

18. A method of treating a patient in need of treatment with antihistamine action, comprising administering to said patient at least one member selected from the piperidine derivatives, or salt or hydrate thereof that is pharmaceutically acceptable as defined in claim 1 in an effective dose.

* * * * *